United States Patent
Hwang et al.

(10) Patent No.: US 10,164,200 B2
(45) Date of Patent: Dec. 25, 2018

(54) ORGANOMETALLIC COMPOUND AND ORGANIC LIGHT-EMITTING DEVICE INCLUDING THE SAME

(71) Applicant: SAMSUNG ELECTRONICS CO., LTD., Suwon-si, Gyeonggi-do (KR)

(72) Inventors: Kyuyoung Hwang, Anyang-si (KR); Ohyun Kwon, Yongin-si (KR); Seungyeon Kwak, Yongin-si (KR); Kum Hee Lee, Suwon-si (KR); Aram Jeon, Suwon-si (KR); Hyeonho Choi, Seoul (KR); Byoungki Choi, Hwaseong-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 199 days.

(21) Appl. No.: 15/263,850

(22) Filed: Sep. 13, 2016

(65) Prior Publication Data

US 2017/0084850 A1 Mar. 23, 2017

(30) Foreign Application Priority Data

Sep. 22, 2015 (KR) .................. 10-2015-0134134

(51) Int. Cl.
*H01L 51/50* (2006.01)
*H01L 51/00* (2006.01)
(Continued)

(52) U.S. Cl.
CPC ...... *H01L 51/0085* (2013.01); *C07F 15/0026* (2013.01); *C07F 15/0033* (2013.01);
(Continued)

(58) Field of Classification Search
CPC . H01L 51/0085; H01L 51/5016; C09K 11/06; C09K 11/025; C09K 2211/1044;
(Continued)

(56) References Cited

U.S. PATENT DOCUMENTS

| | | | |
|---|---|---|---|
| 2004/0230061 A1* | 11/2004 | Seo | C07F 15/0033 548/402 |
| 2014/0027716 A1 | 1/2014 | Tsai et al. | |
| 2014/0158993 A1 | 6/2014 | So et al. | |

FOREIGN PATENT DOCUMENTS

| | | |
|---|---|---|
| JP | 2004-015578 A | 1/2004 |
| JP | 2007-031678 A | 2/2007 |

OTHER PUBLICATIONS

Katherine L. Garner et al. "Luminescent Platinum Complexes with Terdentate Ligands Forming 6-Membered Chelate Rings: Advantageous and Deleterious Effects in N^N^N^ and N^C^N^ -Coordinated Complexes", Inorg. Chem. 2010, 19(2), 476-487.

(Continued)

*Primary Examiner* — Gregory D Clark
(74) *Attorney, Agent, or Firm* — Cantor Colburn LLP

(57) ABSTRACT

An organometallic compound represented by Formula 1:

$$M(L_1)_{n1}(L_2)_{n2} \quad \text{Formula 1}$$

wherein in Formula 1, M in Formula 1 is selected from iridium (Ir), platinum (Pt), osmium (Os), titanium (Ti), zirconium (Zr), hafnium (Hf), europium (Eu), terbium (Tb), thulium (Tm), and rhodium (Rh), $L_1$ in Formula 1 is selected from a ligand represented by Formula 2A or 2B as they are defined in the specification, and $L_2$ in Formula 1 is selected from a mono-anionic organic ligand.

20 Claims, 1 Drawing Sheet

(51) Int. Cl.
*C09K 11/06* (2006.01)
*C09K 11/02* (2006.01)
*C07F 15/00* (2006.01)

(52) U.S. Cl.
CPC ............ *C09K 11/025* (2013.01); *C09K 11/06* (2013.01); *C09K 2211/1044* (2013.01); *C09K 2211/185* (2013.01); *H01L 51/5016* (2013.01)

(58) Field of Classification Search
CPC ........... C09K 2211/185; C07F 15/0026; C07F 15/0033; C07D 209/86; C07D 209/94; C07D 255/04
See application file for complete search history.

(56) References Cited

OTHER PUBLICATIONS

Lu Wang et al. "Novel Antitumor Agent, Trilacunary Keggin-Type Tungstobismuthate, Inhibits Proliferation and Induces Apoptosis in Human Gastric Cancer SGC-7901 Cells", Inorg. Chem. 2013, 52(9), 5119-5127.

Qingguo Wu et al. "Blue-Luminescent/Electroluminescent Zn(II) Compounds of 7-Azaindole and N-(2-Pyridyl)-7-azaindole: Zn(7-azaindole)2 (CH3COO)2, Zn(NPA) (CH3COO)2, and Zn(NPA)((S)-(+)-CH3CH2CH(CH3)COO)2 (NPA= N-(2-Pyridyl)-7azaindole)", Inorg. Chem. 2000, 39(23), 5248-5254.

Shu-Bin Zhao et al. "Intramolecular C—H Activation Directed Self-Assembly of an Organoplatinum(II) Molecular Square", J. Am. Chem. Soc. 2007, 129(11), 3092-3093.

\* cited by examiner

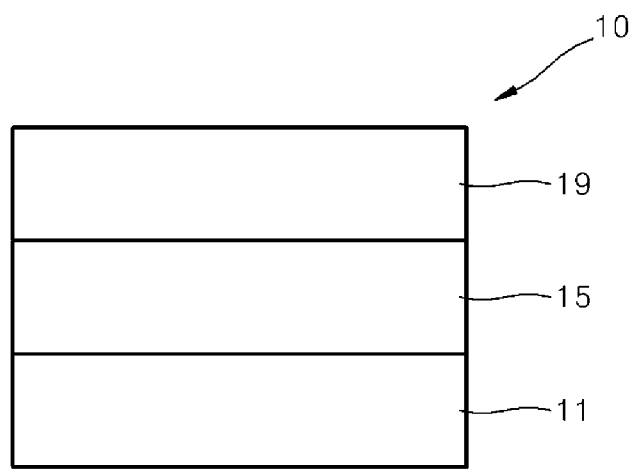

ORGANOMETALLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2015-0134134, filed on Sep. 22, 2015, in the Korean Intellectual Property Office, and all the benefits accruing therefrom under 35 U.S.C. § 119, the content of which is incorporated herein in its entirety by reference.

BACKGROUND

1. Field

One or more embodiments relate to an organometallic compound and an organic light-emitting device including the same.

2. Description of the Related Art

Organic light emitting devices (OLEDs) are self-emission devices that have wide viewing angles, high contrast ratios, and short response times. In addition, OLEDs exhibit excellent brightness, driving voltage, and response speed characteristics, and produce full-color images.

In an example, an organic light-emitting device includes an anode, a cathode, and an organic layer that is disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons change from an excited state to a ground state, thereby generating light.

Various types of organic light emitting devices are known. However, there still remains a need in OLEDs having low driving voltage, high efficiency, high brightness, and long lifespan.

SUMMARY

One or more embodiments relate to a novel organometallic compound and an organic light-emitting device including the same.

Additional aspects will be set forth in part in the description which follows and, in part, will be apparent from the description, or may be learned by practice of the presented exemplary embodiments.

An aspect provides an organometallic compound represented by Formula 1 below:

$$M(L_1)_{n1}(L_2)_{n2} \qquad \text{Formula 1}$$

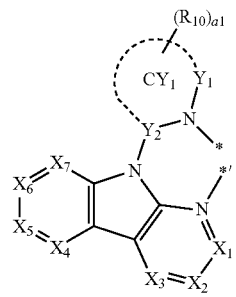

Formula 2A

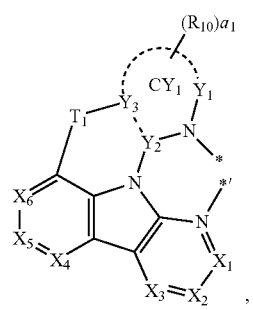

Formula 2B wherein

M in Formula 1 is selected from iridium (Ir), platinum (Pt), osmium (Os), titanium (Ti), zirconium (Zr), hafnium (Hf), europium (Eu), terbium (Tb), thulium (Tm), and rhodium (Rh), $L_1$ in Formula 1 is a ligand represented by Formula 2A or 2B, $L_2$ in Formula 1 is selected from a mono-anionic organic ligand,

* and *' in Formulae 2A and 2B each indicate a binding site to M in Formula 1, n1 in Formula 1 is 1, 2, or 3, and when n1 is 2 or more, 2 or more groups $L_1$ are identical to or different from each other, n2 in Formula 1 is 0, 1, 2, or 3, and when n2 is 2 or more, 2 or more groups $L_2$ are identical to or different from each other, $Y_1$ and $Y_3$ in Formulae 2A and 2B are each independently carbon or nitrogen, $Y_2$ in Formulae 2A and 2B is carbon, a bond between $Y_2$ and $Y_3$ in Formula 2B is a double bond, $CY_1$ in Formulae 2A and 2B is a $C_2$-$C_{30}$ heterocyclic group, in Formulae 2A and 2B, $X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, $X_7$ is N or $C(R_7)$, $T_1$ in Formula 2B is selected from a single bond, *—O—*', *—S—*', *—N($R_{31}$)—*', *—C($R_{31}$)($R_{32}$)—*', *—C($R_{31}$)=C($R_{32}$)—*', and *—Si($R_{31}$)($R_{32}$)—*', and $R_{31}$ and $R_{32}$ are optionally bound to each other to form a substituted or unsubstituted $C_5$-$C_{30}$ carbocyclic group or a substituted or unsubstituted $C_2$-$C_{30}$ heterocyclic group, $R_1$ to $R_7$, $R_{10}$, $R_{31}$, and $R_{32}$ are each independently selected from hydrogen, deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-N(Q_1)(Q_2)$, $-Si(Q_3)(Q_4)(Q_5)$, $-B(Q_6)(Q_7)$, and $-P(=O)(Q_8)(Q_9)$, a1 is an integer selected from 0 to 5, two or more among $R_1$ to $R_3$ in Formulae 2A and 2B are optionally bound to each other to form a substituted or unsubstituted $C_6$-$C_{30}$ carbocyclic group or a substituted or unsubstituted $C_2$-$C_{30}$ heterocyclic group, two or more among $R_4$ to $R_7$ in Formula 2A are optionally bound to each other to form a substituted or unsubstituted $C_5$-$C_{30}$ carbocyclic group or a substituted or unsubstituted $C_2$-$C_{30}$ heterocyclic group, two or more among $R_4$ to $R_6$ in Formula 2B are optionally bound to each other to form a substituted or unsubstituted $C_5$-$C_{30}$ carbocyclic group or a substituted or unsubstituted $C_2$-$C_{30}$ heterocyclic group, two or more among groups $R_{10}$ in the number of a1 in Formulae 2A and 2B are optionally bound to each other to form a substituted or unsubstituted $C_5$-$C_{30}$ carbocyclic group or a substituted or unsubstituted $C_2$-$C_{30}$ heterocyclic group, and at least one of substituents of the substituted $C_5$-$C_{30}$ carbocyclic group, substituted $C_2$-$C_{30}$ heterocyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:

deuterium, $-F$, $-Cl$, $-Br$, $-I$, $-CD_3$, $-CD_2H$, $-CDH_2$, $-CF_3$, $-CF_2H$, $-CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, $-F$, $-Cl$, $-Br$, $-I$, $-CD_3$, $-CD_2H$, $-CDH_2$, $-CF_3$, $-CF_2H$, $-CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-N(Q_{11})(Q_{12})$, $-Si(Q_{13})(Q_{14})(Q_{15})$, $-B(Q_{16})(Q_{17})$, and $-P(=O)(Q_{18})(Q_{19})$, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, $-F$, $-Cl$, $-Br$, $-I$, $-CD_3$, $-CD_2H$, $-CDH_2$, $-CF_3$, $-CF_2H$, $-CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-N(Q_{21})(Q_{22})$, $-Si(Q_{23})(Q_{24})(Q_{25})$, $-B(Q_{26})(Q_{27})$, and $-P(=O)(Q_{28})(Q_{29})$; and $-N(Q_{31})(Q_{32})$, $-Si(Q_{33})(Q_{34})(Q_{35})$, $-B(Q_{36})(Q_{37})$ and $-P(=O)(Q_{38})(Q_{39})$, wherein $Q_1$ to $Q_9$, $Q_{11}$ to $Q_{19}$, $Q_{21}$ to $Q_{29}$, and $Q_{31}$ to $Q_{39}$ are each independently selected from a $C_6$-$C_{60}$ aryl group, a $C_6$-$C_{60}$ aryloxy group, a $C_6$-$C_{60}$ arylthio group, a $C_1$-C60 heteroaryl group, a monovalent non-aromatic condensed polycyclic group, and a monovalent non-aromatic condensed heteropolycyclic group, each substituted with at least one selected from hydrogen, deuterium, $-F$, $-Cl$, $-Br$, $-I$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ alkyl group, and a $C_6$-$C_{60}$ aryl group.

According to another aspect of an exemplary embodiment, an organic light-emitting device includes:

a first electrode, a second electrode, and an organic layer disposed between the first electrode and the second electrode, wherein the organic layer includes an emission layer and at least one of the organometallic compounds described above.

The organometallic compounds may act as a dopant in the emission layer.

BRIEF DESCRIPTION OF THE DRAWING

These and/or other aspects will become apparent and more readily appreciated from the following description of the exemplary embodiments, taken in conjunction with FIG. 1 which is a schematic view of an organic light-emitting device according to an embodiment.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

An organometallic compound according to an embodiment is represented by Formula 1 below:

$$M(L_1)_{n1}(L_2)_{n2} \qquad \text{Formula 1}$$

M in Formula 1 may be selected from iridium (Ir), platinum (Pt), osmium (Os), titanium (Ti), zirconium (Zr), hafnium (Hf), europium (Eu), terbium (Tb), thulium (Tm), and rhodium (Rh).

For example, M in Formula 1 may be selected from iridium, platinum, and osmium, but is not limited thereto.

$L_1$ in Formula 1 may be a group represented by Formula 2A or 2B. Formulae 2A and 2B are the same as described below.

$L_2$ in Formula 1 may be selected from mono-anionic organic ligands.

* and *' in Formulae 2A and 2B may each be a binding site to M in Formula 1.

n1 in Formula 1 may be 1, 2, or 3, and when n1 is 2 or more, 2 or more groups $L_1$ may be identical to or different from each other.

n2 in Formula 1 may be 0, 1, 2, or 3, and when n2 is 2 or more, 2 or more groups $L_2$ may be identical to or different from each other.

For example, in Formula 1,

M may be Ir or Os and the sum of n1 and n2 may be 3 or 4; or

M may be Pt and the sum of n1 and n2 may be 2, but M is not limited thereto.

In an embodiment, in Formula 1,

M may be Ir, and when n1 may be 2, n2 may be 1;

M may be Os, and when n1 may be 2, and n2 may be 2; or

M may be Pt, and when n1 may be 2, and n2 may be O, but M is not limited thereto.

$Y_1$ and $Y_3$ in Formulae 2A and 2B may each independently be carbon or nitrogen.

For example, $Y_3$ in Formulae 2A and 2B may be carbon.

$Y_2$ in Formulae 2A and 2B may be carbon, and the bond between $Y_2$ and $Y_3$ in Formula 2B may be a double bond.

$CY_1$ in Formulae 2A and 2B may be a $C_2$-$C_{30}$ heterocyclic group.

For example, $CY_1$ in Formulae 2A and 2B may include a five-membered ring containing at least one nitrogen atom as a ring-forming atom.

In an embodiment, $CY_1$ in Formulae 2A and 2B may be selected from a pyrrole ring, an isoindole ring, an indole ring, an indazole ring, a pyrazole ring, an imidazole ring, a triazole ring, an oxazole ring, an isoxazole ring, an oxadiazole ring, a thiazole ring, an isothiazole ring, a thiadiazole ring, a purine ring, a benzoimidazole ring, an isobenzothiazole ring, a benzoxazole ring, an isobenzoxazole ring, an imidazopyridine ring, an imidazopyrimidine ring, and a pyrrolopyridine ring, but is not limited thereto.

In some embodiments, $CY_1$ in Formulae 2A and 2B may each independently be a pyrrole ring, an isoindole ring, an indole ring, a pyrrolopyridine ring, a pyrazole ring, or a benzoimidazole ring.

In Formulae 2A and 2B, $X_1$ may be N or $C(R_1)$, $X_2$ may be N or $C(R_2)$, $X_3$ may be N or $C(R_3)$, $X_4$ may be N or $C(R_4)$, $X_5$ may be N or $C(R_5)$, $X_6$ may be N or $C(R_6)$, and $X_7$ may be N or $C(R_7)$.

For example, in Formulae 2A and 2B, $X_1$ may be $C(R_1)$, $X_2$ may be $C(R_2)$, $X_3$ may be $C(R_3)$, $X_4$ may be $C(R_4)$, $X_5$ may be $C(R_5)$, $X_6$ may be $C(R_6)$, and $X_7$ may be $C(R_7)$, but they are not limited thereto.

In Formula 2B, $T_1$ may be selected from a single bond, *—O—*', *—S—*', *—N($R_{31}$)—*', *—C($R_{31}$)($R_{32}$)—*', *—C($R_{31}$)=C($R_{32}$)—*', and *—Si($R_{31}$)($R_{32}$)—*', and $R_{31}$ and $R_{32}$ are optionally bound to each other to form a substituted or unsubstituted $C_5$-$C_{30}$ carbocyclic group, or a substituted or unsubstituted $C_2$-$C_{30}$ heterocyclic group (for example, a substituted or unsubstituted cyclopropane, a substituted or unsubstituted cyclobutane, a substituted or unsubstituted cyclopentane, a substituted or unsubstituted cyclohexane, a substituted or unsubstituted benzene).

For example, $T_1$ in Formula 2B may be selected from *—O—*', *—S—*', *—C($R_{31}$)($R_{32}$)—*' and groups represented by Formulae 11-1 to 11-4:

Formula 11-1

Formula 11-2

Formula 11-3

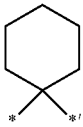

Formula 11-4

* and *' in Formulae 11-1 to 11-4 each indicate a binding site to a neighboring atom.

$R_1$ to $R_7$, $R_{10}$, $R_{31}$, and $R_{32}$ in Formula 1 may each independently be selected from hydrogen, deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-C10 heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), and —P(=O)($Q_8$)($Q_9$).

For example, $R_1$ to $R_7$, $R_{10}$, $R_{31}$, and $R_{32}$ in Formula 1 may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl (adamantyl) group, a norbornanyl (norbornyl) group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —N($Q_1$)($Q_2$), —Si($Q_3$)($Q_4$)($Q_5$), —B($Q_6$)($Q_7$), and —P(=O)($Q_8$)($Q_9$), $Q_1$ to $Q_9$ may each independently be selected from:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group.

In some embodiments, $R_1$ to $R_7$, $R_{10}$, $R_{31}$, and $R_{32}$ in Formula 1 may each independently be hydrogen, deuterium, —F, a cyano group, a nitro group, —SF$_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group;

a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group, each substituted with at least one selected from deuterium, —F, —CD$_3$, —CD$_2$H, —CDH$_2$, —CF$_3$, —CF$_2$H, —CFH$_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group; and —N($Q_1$)($Q_2$), —Si($Q_3$)($Q_4$)($Q_5$), —B($Q_5$)($Q_7$) —P(=O) ($Q_8$)($Q_9$), and $Q_1$ to $Q_9$ may each independently be selected from:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group.

In some embodiments, $R_1$ to $R_7$, $R_{10}$, $R_{31}$, and $R_{32}$ in Formula 1 may each independently be selected from hydrogen, deuterium, —F, a cyano group, a nitro group, —SF$_5$, —CH$_3$, —CD$_3$, —CD$_2$H, —CDH$_2$, —CF$_3$, —CF$_2$H, —CFH$_2$, groups represented by Formulae 9-1 to 9-19, groups represented by Formulae 10-1 to 10-36, and —Si ($Q_3$)($Q_4$)($Q_5$), and $Q_3$ to $Q_5$ may each independently be selected from:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group:

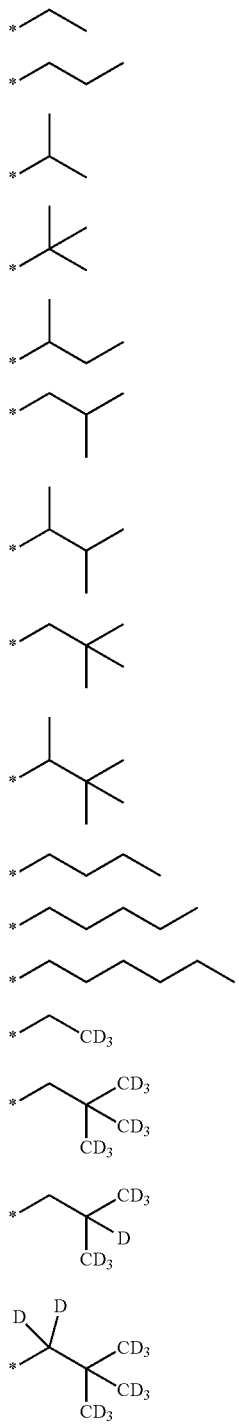
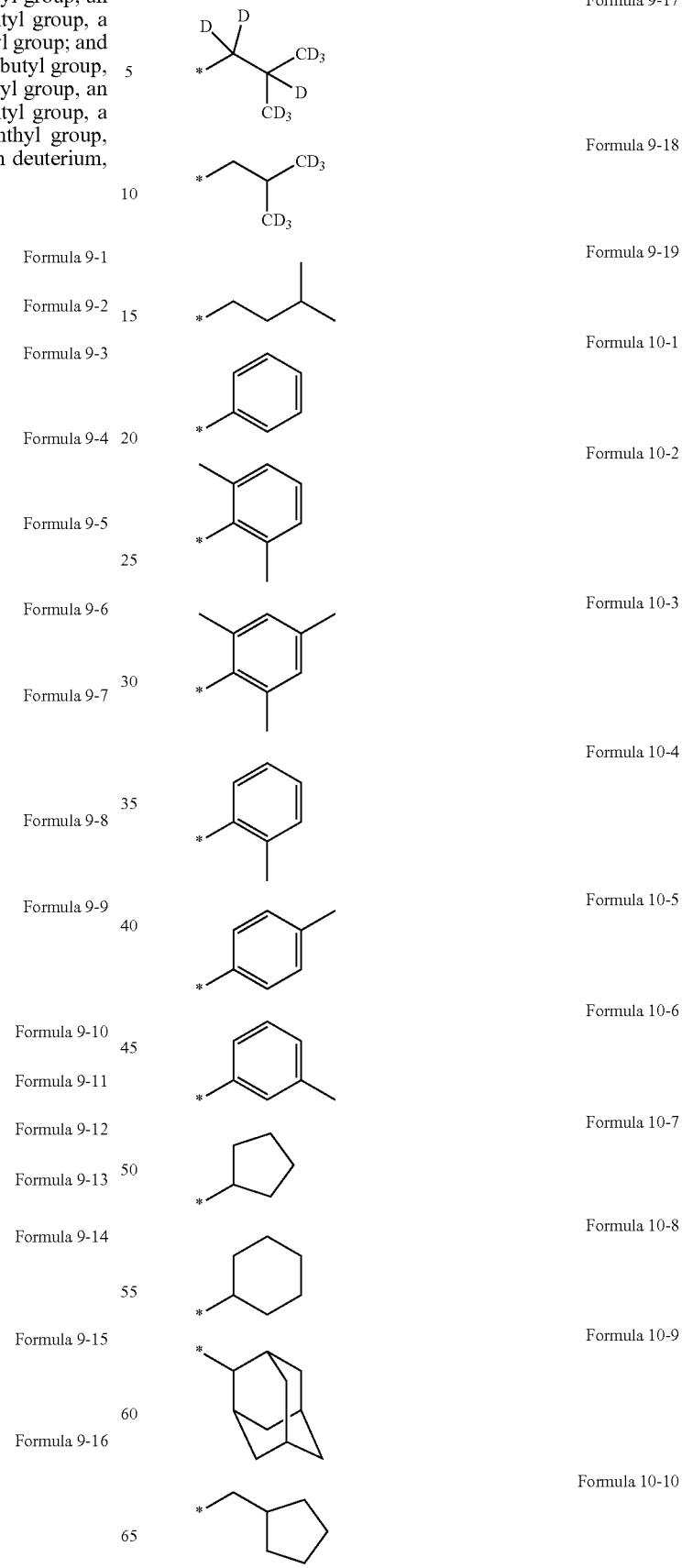

-continued
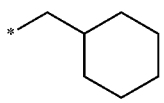
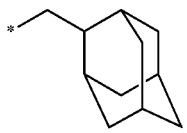
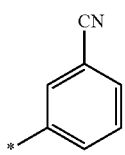
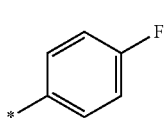
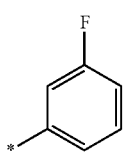
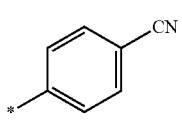
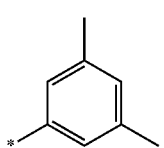
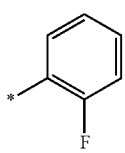
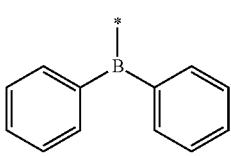
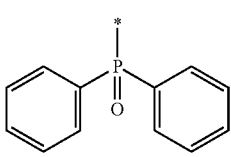
-continued
Formula 10-11
Formula 10-12
Formula 10-14
Formula 10-16
Formula 10-18
Formula 10-19
Formula 10-20
Formula 10-21
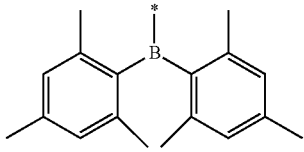
Formula 10-22
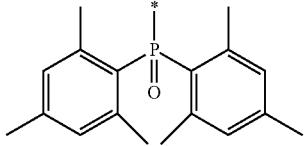
Formula 10-23
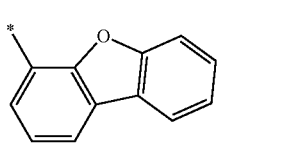
Formula 10-24
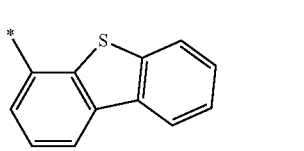
Formula 10-25
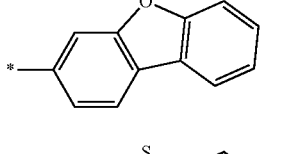
Formula 10-26
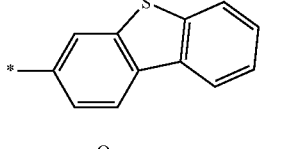
Formula 10-27
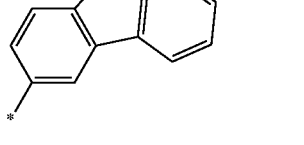
Formula 10-28
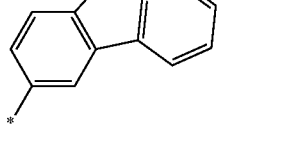
Formula 10-29
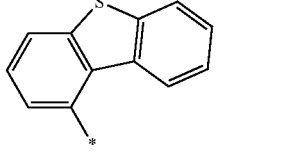
Formula 10-30

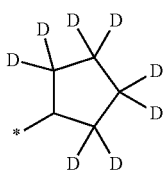
Formula 10-31

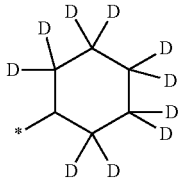
Formula 10-32

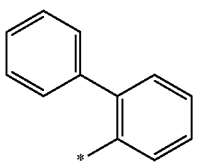
Formula 10-33

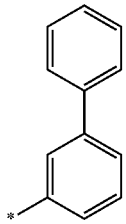
Formula 10-34

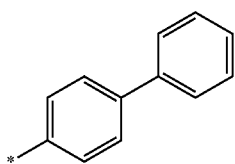
Formula 10-35

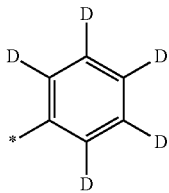
Formula 10-36

\* in Formulae 9-1 to 9-19 and 10-1 to 10-36 indicates a binding site to a neighboring atom.

a1 in Formulae 2A and 2B indicates the number of groups $R_{10}$, and may be an integer selected from 0 to 5. When a1 is 2 or more, 2 or more groups $R_1$ may be identical to or different from each other.

Two neighboring substituents among $R_1$ to $R_3$ in Formulae 2A and 2B may optionally be bound to each other to form a substituted or unsubstituted $C_5$-$C_{30}$ carbocyclic ring or a substituted or unsubstituted $C_2$-$C_{30}$ heterocyclic ring (for example, a substituted or unsubstituted cyclopentane ring, a substituted or unsubstituted cyclopentene ring, a substituted or unsubstituted cyclohexane ring, a substituted or unsubstituted cyclohexene ring, a substituted or unsubstituted adamantane ring, a substituted or unsubstituted bicycloheptane ring, a substituted or unsubstituted bicycloheptene ring, a substituted or unsubstituted benzene ring, a substituted or unsubstituted naphthalene ring, a substituted or unsubstituted pyridine ring, a substituted or unsubstituted pyrimidine ring, or the like).

Two neighboring substituents among $R_4$ to $R_7$ in Formula 2A may optionally be bound to each other to form a substituted or unsubstituted $C_5$-$C_{30}$ carbocyclic ring or a substituted or unsubstituted $C_2$-$C_{30}$ heterocyclic ring (for example, a substituted or unsubstituted cyclopentane ring, a substituted or unsubstituted cyclopentene ring, a substituted or unsubstituted cyclohexane ring, a substituted or unsubstituted cyclohexene ring, a substituted or unsubstituted adamantane ring, a substituted or unsubstituted bicycloheptane ring, a substituted or unsubstituted bicycloheptene ring, a substituted or unsubstituted benzene ring, a substituted or unsubstituted naphthalene ring, a substituted or unsubstituted pyridine ring, a substituted or unsubstituted pyrimidine ring, or the like).

Two neighboring substituents in $R_4$ to $R_6$ in Formula 2B may optionally be bound to each other to form a substituted or unsubstituted $C_5$-$C_{30}$ carbocyclic ring or a substituted or unsubstituted $C_2$-$C_{30}$ heterocyclic ring (for example, a substituted or unsubstituted cyclopentane ring, a substituted or unsubstituted cyclopentene ring, a substituted or unsubstituted cyclohexane ring, a substituted or unsubstituted cyclohexene ring, a substituted or unsubstituted adamantane ring, a substituted or unsubstituted bicycloheptane ring, a substituted or unsubstituted bicycloheptene ring, a substituted or unsubstituted benzene ring, a substituted or unsubstituted naphthalene ring, a substituted or unsubstituted pyridine ring, a substituted or unsubstituted pyrimidine ring, or the like).

Two or more of groups $R_{10}$ in the number of a1 in Formulae 2A and 2B may optionally be bound to each other to form a substituted or unsubstituted $O_5$-$O_{30}$ carbocyclic ring or a substituted or unsubstituted $C_2$-$C_{30}$ heterocyclic ring (for example, a substituted or unsubstituted cyclopentane ring, a substituted or unsubstituted cyclopentene ring, a substituted or unsubstituted cyclohexane ring, a substituted or unsubstituted cyclohexene ring, a substituted or unsubstituted adamantane ring, a substituted or unsubstituted bicycloheptane ring, a substituted or unsubstituted bicycloheptene ring, a substituted or unsubstituted benzene ring, a substituted or unsubstituted naphthalene ring, a substituted or unsubstituted pyridine ring, a substituted or unsubstituted pyrimidine ring, or the like).

At least one of $X_1$ to $X_7$ in Formulae 2A and 2B may be C(CN). Accordingly, the organometallic compound represented by Formula 1 may have high color purity and high heat resistance.

In an embodiment, $X_5$ in Formulae 2A and 2B may be C(CN), but is not limited thereto.

In an embodiment, ligand $L_1$ in Formula 1 may be selected from ligands represented by Formulae 2A-1 to 2A-4 and 2B-1 to 2B-3:

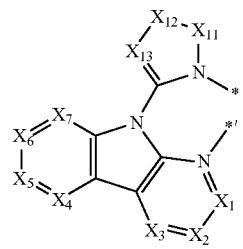
Formula 2A-1

-continued

Formula 2A-2

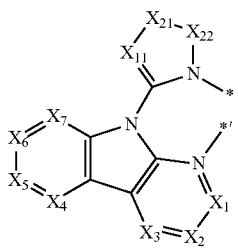

Formula 2A-3

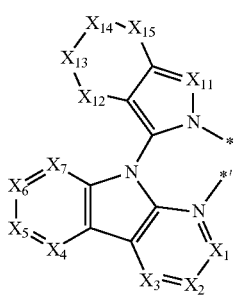

Formula 2A-4

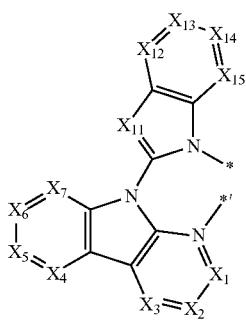

Formula 2B-1

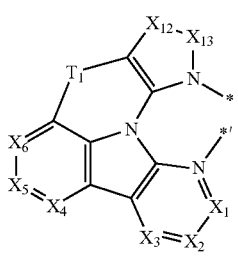

Formula 2B-2

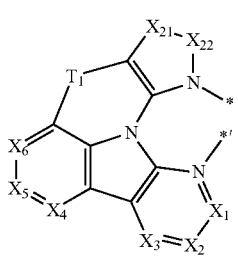

-continued

Formula 2B-3

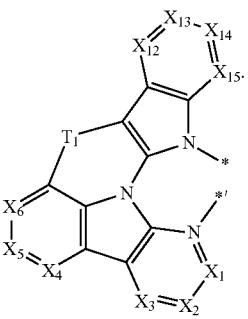

In Formulae 2A-1 to 2A-4 and 2B-1 to 2B-3,
descriptions of $X_1$ to $X_7$ and $T_1$ are the same as described herein,
$X_{11}$ is N or $C(R_{11})$, $X_{12}$ is N or $C(R_{12})$, $X_{13}$ is N or $C(R_{13})$, $X_{14}$ is N or $C(R_{14})$, and $X_{15}$ is N or $C(R_{15})$,
$X_{21}$ is O, S, $N(R_{21})$, or $C(R_{22})(R_{23})$,
$X_{21}$ is O, S, $N(R_{24})$, or $C(R_{25})(R_{26})$,
descriptions of $R_{11}$ to $R_{15}$ and $R_{21}$ to $R_{26}$ are the same as described in connection with $R_{10}$, and
* and *' each indicate a binding site to M in Formula 1.
For example, in Formulae 2A-1 to 2A-4 and 2B-1 to 2B-3,
$X_1$ is $C(R_1)$, $X_2$ is $C(R_2)$, $X_3$ is $C(R_3)$, $X_4$ is $C(R_4)$, $X_5$ is $C(R_5)$, $X_6$ is $C(R_6)$, and $X_7$ is $C(R_7)$,
$T_1$ is selected from *—O—*', *—S—*', *—$C(R_{31})(R_{32})$—*', and groups represented by Formulae 11-1 to 11-4,
$R_1$ to $R_7$, $R_{11}$ to $R_{15}$, $R_{21}$ to $R_{26}$, $R_{31}$, and $R_{32}$ are each independently selected from: hydrogen, deuterium, —F, a cyano group, a nitro group, —$SF_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group;

a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group, each substituted with at least one selected from deuterium, —F, —CD$_3$, —CD$_2$H, —CDH$_2$, —CF$_3$, —CF$_2$H, —CFH$_2$, a cyano group, a nitro group, a C$_1$-C$_{10}$ alkyl group, a C$_1$-C$_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group; and —N(Q$_1$)(Q$_2$), —Si(Q$_3$)(Q$_4$)(Q$_5$), —B(Q$_6$)(Q$_7$), —P(=O)(Q$_8$)(Q$_9$); and Q$_1$ to Q$_9$ are each independently selected from:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a C$_1$-C$_{10}$ alkyl group, and a phenyl group, two neighboring substituents among R$_1$ to R$_3$ may optionally be bound to each other to form a substituted or unsubstituted C$_5$-C$_{10}$ carbocyclic ring, two neighboring substituents among R$_4$ to R$_7$ may optionally be bound to each other to form a substituted or unsubstituted C$_5$-C$_{10}$ carbocyclic ring, and two neighboring substituents among R$_{11}$ to R$_{15}$ and R$_{21}$ to R$_{26}$ may optionally be bound to each other to form a substituted or unsubstituted C$_5$-C$_{10}$ carbocyclic ring (for example, a substituted or unsubstituted cyclopentane ring, a substituted or unsubstituted cyclopentene ring, a substituted or unsubstituted cyclohexane ring, a substituted or unsubstituted cyclohexene ring, a substituted or unsubstituted adamantane ring, a substituted or unsubstituted bicycloheptane ring, a substituted or unsubstituted bicycloheptene ring, a substituted or unsubstituted benzene ring, or a substituted or unsubstituted naphthalene ring), but is not limited thereto.

In some embodiments, in Formulae 2A-1 to 2A-4 and 2B-1 to 2B-3,

X$_1$ is C(R$_1$), X$_2$ is C(R$_2$), X$_3$ is C(R$_3$), X$_4$ is C(R$_4$), X$_5$ is C(R$_5$), X$_6$ is C(R$_6$), and X$_7$ is C(R$_7$), T$_1$ is selected from *—O—*', *—S—*', *—C(R$_{31}$)(R$_{32}$)—*', and groups represented by Formulae 11-1 to 11-4, R$_1$ to R$_7$, R$_{11}$ to R$_{15}$, R$_{21}$ to R$_{26}$, R$_{31}$, and R$_{32}$ are each independently selected from hydrogen, deuterium, —F, a cyano group, a nitro group, —SF$_5$, —CH$_3$, —CD$_3$, —CD$_2$H, —CDH$_2$, —CF$_3$, —CF$_2$H, —CFH$_2$, groups represented by Formulae 9-1 to 9-19, groups represented by Formulae 10-1 to 10-36, and —Si(Q$_3$)(Q$_4$)(Q$_5$), Q3 to Q$_5$ are each independently selected from:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a C$_1$-C$_{10}$ alkyl group, and a phenyl group, but is not limited thereto.

In an embodiment, at least one selected from X$_1$ to X$_7$ in Formulae 2A-1 to 2A-4 and 2B-1 to 2B-3 may be C(CN). In some embodiments, in Formulae 2A-1 to 2A-4, and 2B-1 to 2B-3, X$_5$ may be C(CN) or X$_{12}$ may be C(CN). Accordingly, the organometallic compound represented by Formula 1 may have a high color purity and a high heat resistance.

In some embodiments, ligand L$_1$ in Formula 1 may be selected from ligands represented by Formulae 2A-1(1) to 2A-1(6):

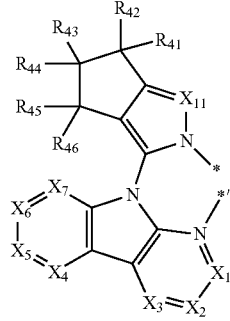

Formula 2A-1(1)

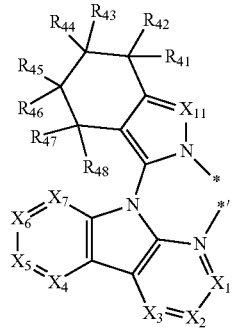

Formula 2A-1(2)

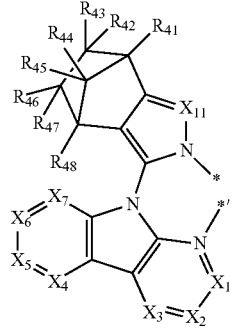

Formula 2A-1(3)

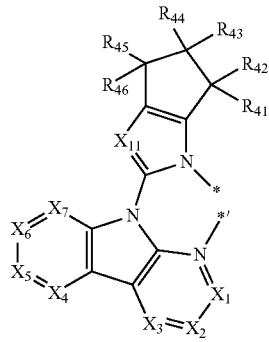

Formula 2A-1(4)

-continued

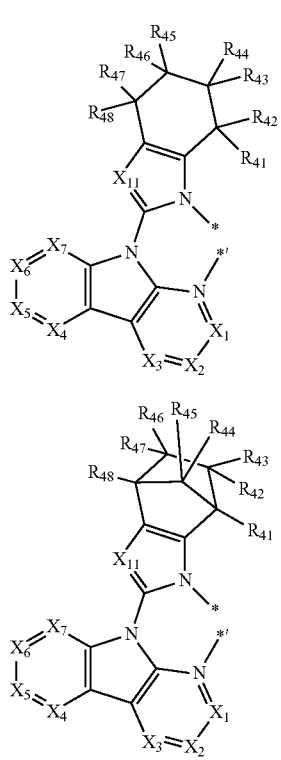

Formula 2A-1(5)

Formula 2A-1(6)

In Formulae 2A-1(1) to 2A-1(6), $X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, and $X_7$ is N or $C(R_7)$, $T_1$ is selected from *—O—*', *—S—*', *—$C(R_{31})(R_{32})$—*', and groups represented by Formulae 11-1 to 11-4, $X_{11}$ is N or $C(R_{11})$, $R_1$ to $R_7$, $R_{11}$, $R_{31}$, $R_{32}$, and $R_{41}$ to $R_{48}$ are each independently selected from:

hydrogen, deuterium, —F, a cyano group, a nitro group, —$SF_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group;

a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group, each substituted with at least one selected from deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group; and —$N(Q_1)(Q_2)$, —$Si(Q_3)(Q_4)(Q_5)$, —$B(Q_6)(Q_7)$ and —$P(=O)(Q_8)(Q_9)$, $Q_1$ to $Q_9$ are each independently selected from:

—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group;

two neighboring substituents among $R_1$ to $R_3$ may optionally be bound to each other to form a substituted or unsubstituted $C_5$-$C_{10}$ carbocyclic ring (for example, a substituted or unsubstituted benzene ring, a substituted or unsubstituted naphthalene ring, or the like), two neighboring substituents among $R_4$ to $R_7$ may optionally be bound to each other to form a substituted or unsubstituted $C_5$-$C_{10}$ carbocyclic ring (for example, a substituted or unsubstituted benzene ring, a substituted or unsubstituted naphthalene ring, or the like), and

* and *' may each be a binding site to M in Formula 1.

In some embodiments, in Formulae 2A-1(1) to 2A-1(6), $X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, and $X_7$ is N or $C(R_7)$, $T_1$ is selected from *—O—*', *—S—*', *—$C(R_{31})(R_{32})$—*', and groups represented by Formulae 11-1 to 11-4, $X_{11}$ is N or $C(R_{11})$, $R_1$ to $R_7$, $R_{11}$, $R_{31}$, $R_{32}$, and $R_{41}$ to $R_{48}$ are each independently selected from hydrogen, deuterium, —F, a cyano group, a nitro group, —$SF_5$, —$CH_3$, —$CD_3$, —$CD_2H$, —$CDH_2$, —$CF_3$, —$CF_2H$, —$CFH_2$, groups represented by Formulae 9-1 to 9-19, groups represented by Formulae 10-1 to 10-36, and —$Si(Q_3)(Q_4)(Q_5)$, $Q_3$ to $Q_5$ are each independently selected from:

—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$,

—CHDCD$_2$H, —CHDCDH$_2$, —CHDCD$_3$, —CD$_2$CD$_3$, —CD$_2$CD$_2$H and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a C$_1$-C$_{10}$ alkyl group, and a phenyl group, but they are not limited thereto.

In an embodiment, at least one selected from X$_1$ to X$_7$ in Formulae 2A-1(1) to 2A-1(6) may be C(CN). In some embodiments, X$_5$ in Formulae 2A-1(1) to 2A-1(6) may be C(CN). Accordingly, the organometallic compound represented by Formula 1 may have high color purity and high heat resistance.

In some embodiments, ligand L$_1$ in Formula 1 may be selected from ligands represented by Formulae 4-1 to 4-7, 4-11 to 4-17, 4-21 to 4-27, 4-31 to 4-37, 4-41 to 4-44, 4-51 to 4-54, 4-61 to 4-64, and 4-71 to 4-74:

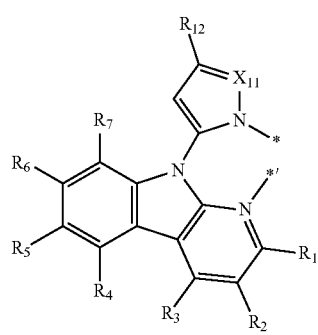

Formula 4-1

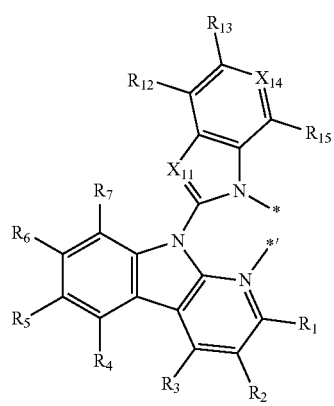

Formula 4-2

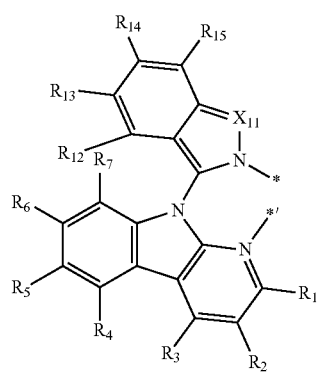

Formula 4-3

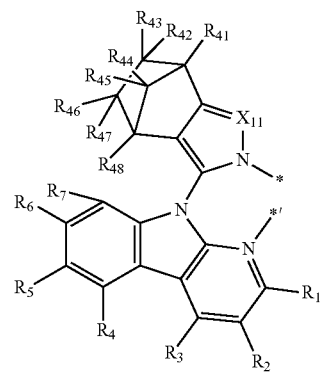

Formula 4-4

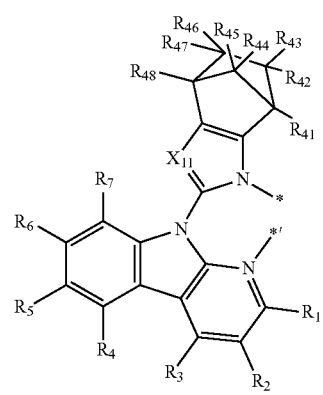

Formula 4-5

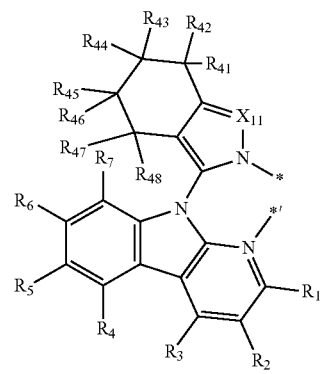

Formula 4-6

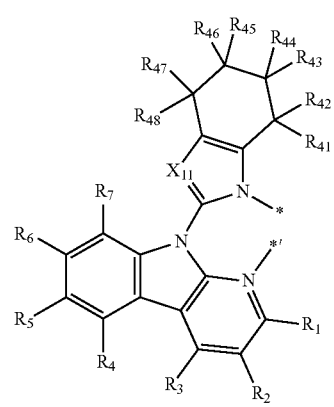

Formula 4-7

Formula 4-11
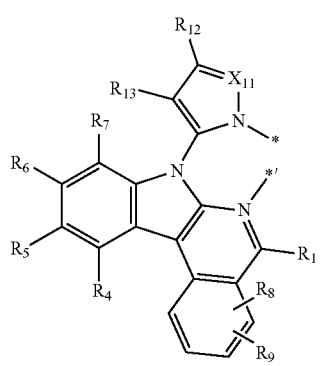
Formula 4-12
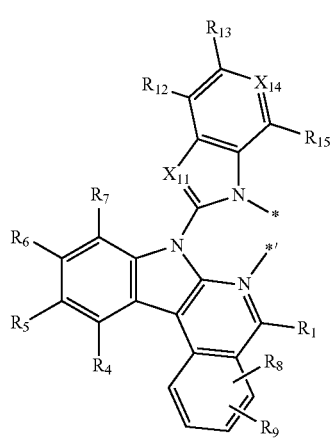
Formula 4-13
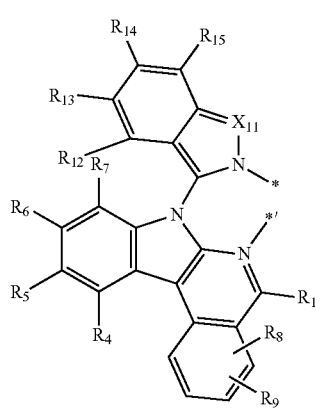
Formula 4-14
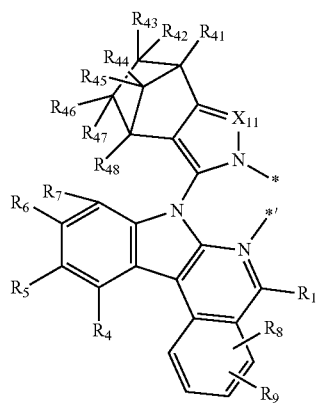
Formula 4-15
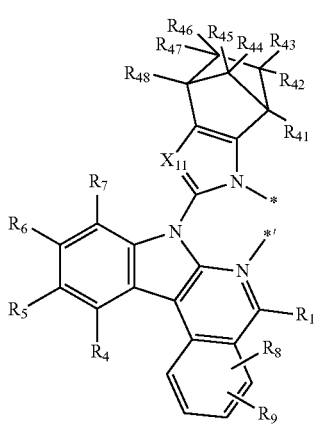
Formula 4-16
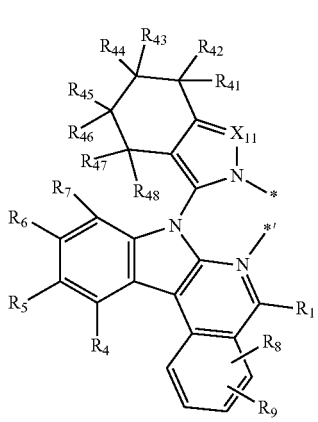
Formula 4-17
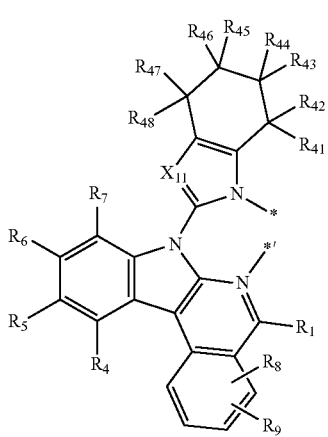
Formula 4-21
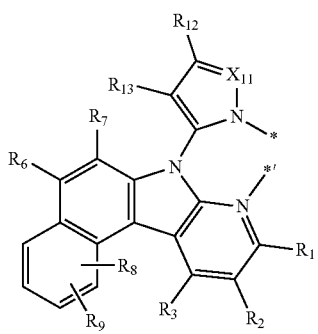

Formula 4-22
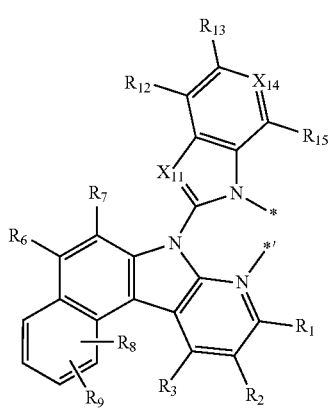
Formula 4-23
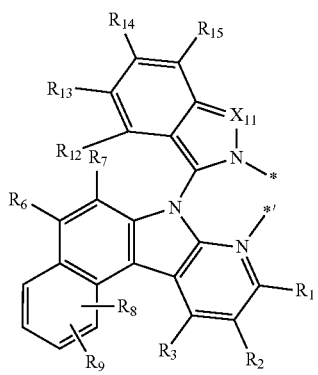
Formula 4-24
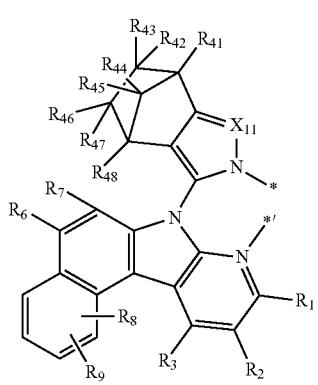
Formula 4-25
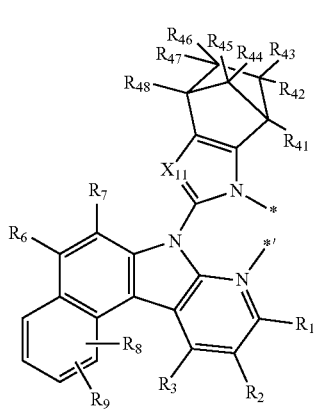
Formula 4-26
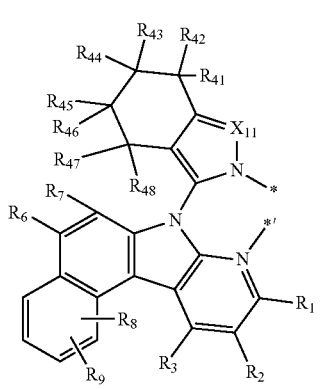
Formula 4-27
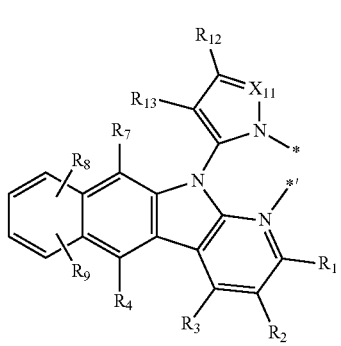
Formula 4-31
Formula 4-32
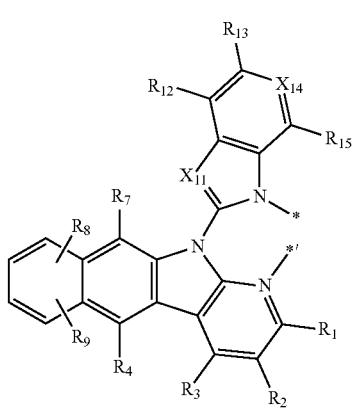

Formula 4-33
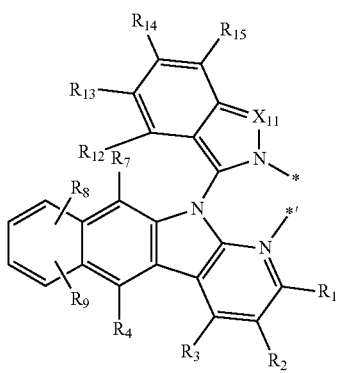
Formula 4-34
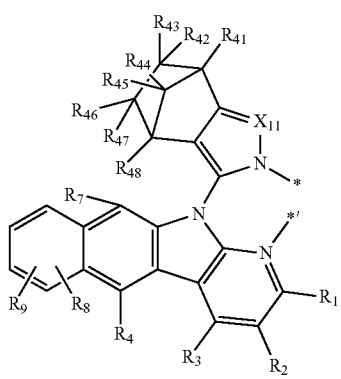
Formula 4-35
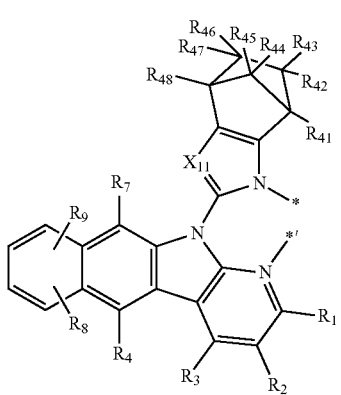
Formula 4-36
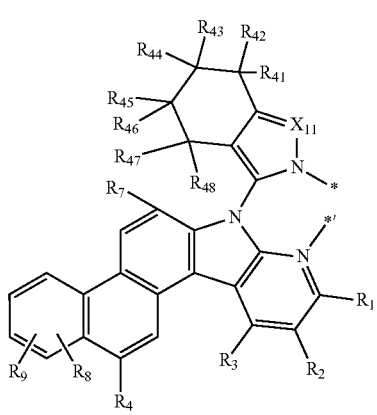
Formula 4-37
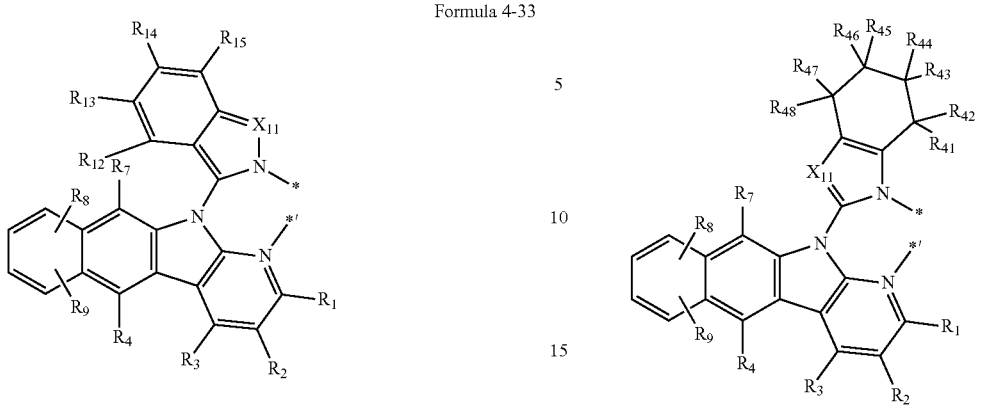
Formula 4-41
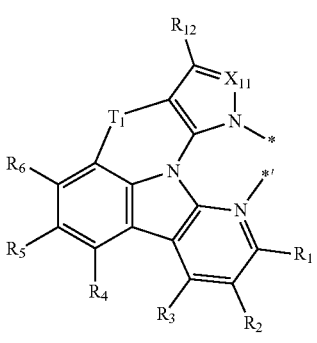
Formula 4-42
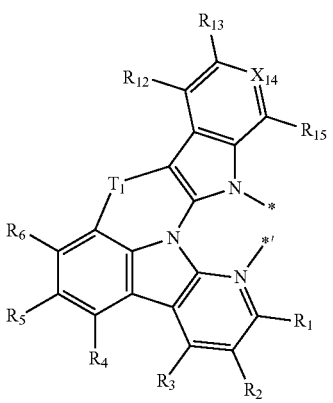
Formula 4-43
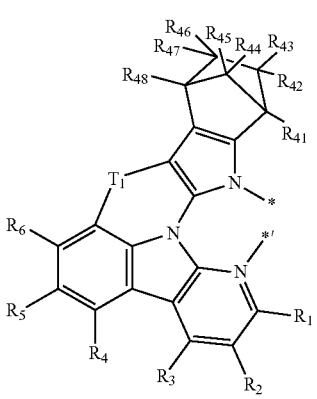

-continued
Formula 4-44
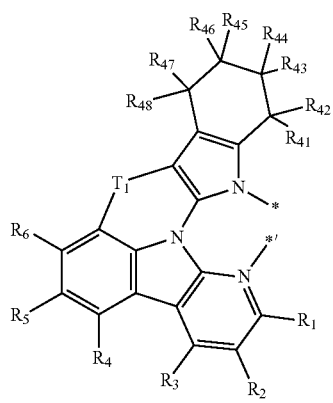
Formula 4-51
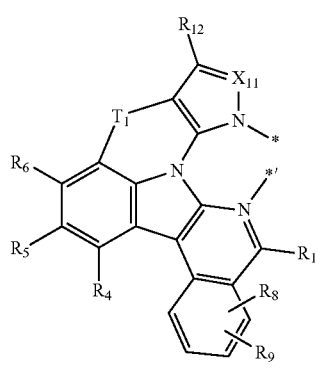
Formula 4-52
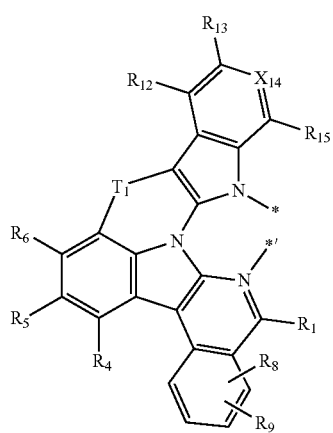
Formula 4-53
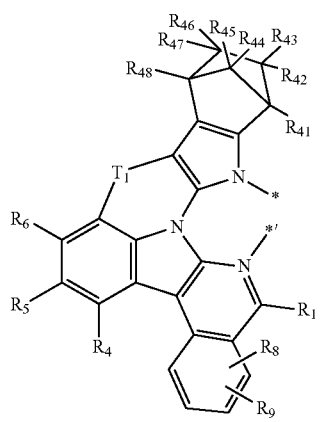
-continued
Formula 4-54
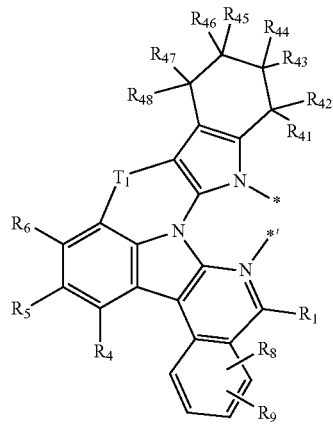
Formula 4-61
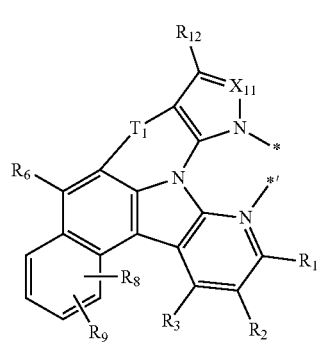
Formula 4-62
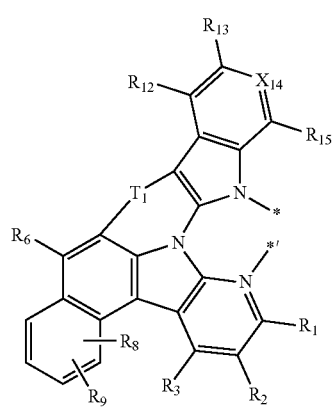
Formula 4-63
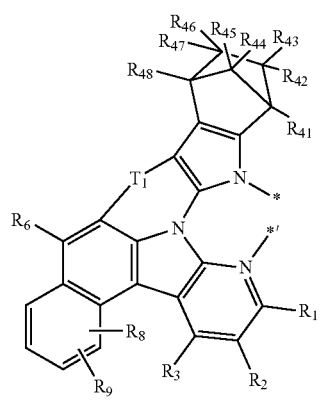

Formula 4-64

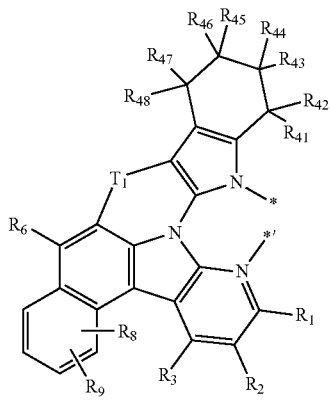

Formula 4-71

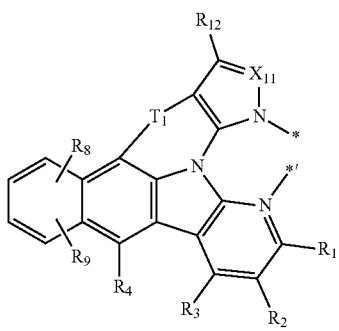

Formula 4-72

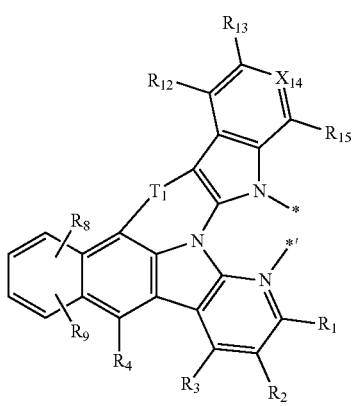

Formula 4-73

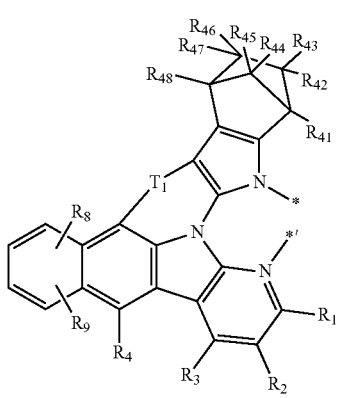

Formula 4-74

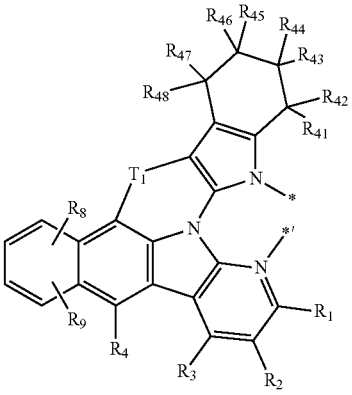

Regarding Formulae 4-1 to 4-7, 4-11 to 4-17, 4-21 to 4-27, 4-31 to 4-37, 4-41 to 4-44, 4-51 to 4-54, 4-61 to 4-64, and 4-71 to 4-74, descriptions of $X_{11}$, $X_{14}$, $T_1$, $R_1$ to $R_7$, $R_{11}$ to $R_{15}$, and $R_{41}$ to $R_{48}$ are the same as described herein, descriptions of $R_8$ and $R_9$ are the same as described in connection with $R_1$, and * and *' each indicates a binding site to M in Formula 1.

For example, in Formulae 4-1 to 4-7, 4-11 to 4-17, 4-21 to 4-27, 4-31 to 4-37, 4-41 to 4-44, 4-51 to 4-54, 4-61 to 4-64, and 4-71 to 4-74, $X_{11}$ is N or $C(R_{11})$, $X_{14}$ is N or $C(R_{14})$, $T_1$ is selected from *—O—*', *—S—*', *—$C(R_{31})$($R_{32}$)—*', and groups represented by Formulae 11-1 to 11-4, $R_1$ to $R_9$, $R_{11}$ to $R_{15}$, $R_{31}$, $R_{32}$, and $R_{41}$ to $R_{48}$ are each independently selected from hydrogen, deuterium, —F, a cyano group, a nitro group, —$SF_5$, —$CH_3$, —$CD_3$, —$CD_2H$, —$CDH_2$, —$CF_3$, —$CF_2H$, —$CFH_2$, groups represented by Formulae 9-1 to 9-19, groups represented by Formulae 10-1 to 10-36, and —$Si(Q_3)(Q_4)(Q_5)$, Q3 to Q5 are each independently selected from:
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group, but they are not limited thereto.

Ligand $L_2$ in Formula 1 may be selected from ligands represented by Formulae 3A to 3F:

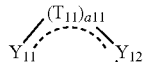

Formula 3A

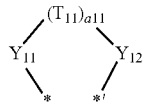

Formula 3B

-continued

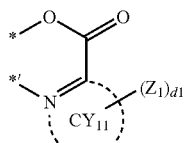

Formula 3C

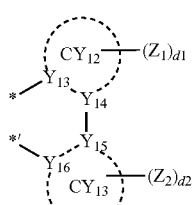

Formula 3D $$*-C\equiv C-Z_1$$

Formula 3E

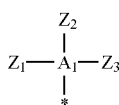

Formula 3F

In Formulae 3A to 3F, $Y_{11}$ is selected from O, N, $N(Z_1)$, $P(Z_1)(Z_2)$, and $As(Z_1)(Z_2)$, $Y_{12}$ is selected from O, N, $N(Z_3)$, $P(Z_3)(Z_4)$, and $As(Z_3)(Z_4)$, $CY_{11}$ is a $C_2$-$C_{30}$ heterocyclic group, $T_{11}$ is each independently selected from a single bond, a double bond, *—$C(Z_{11})(Z_{12})$—*', *—$C(Z_{11})=C(Z_{12})$—*', *=$C(Z_{11})$—*', *—$C(Z_{11})=$*', *=$C(Z_{11})$—$C(Z_{12})=C(Z_{13})$—*', *—$C(Z_{11})=C(Z_{12})$—$C(Z_{13})=$*', *—$N(Z_{11})$—*', and a substituted or unsubstituted $C_6$-$C_{30}$ arylene group, a11 is an integer selected from 1 to 10, $Y_{13}$ to $Y_{16}$ are each independently carbon (C) or nitrogen (N), $Y_{13}$ and $Y_{14}$ are bound to each other via a single bond or a double bond, $Y_{15}$ and $Y_{16}$ are bound to each other via a single bond or a double bond, $CY_{12}$ and $CY_{13}$ are each independently selected from a $C_5$-$C_{60}$ cyclic group and a $C_2$-$C_{60}$ heterocyclic group, $A_i$ is P or As, $Z_1$ to $Z_4$ and $Z_{11}$ to $Z_{13}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, —$B(Q_6)(Q_7)$, and —$P(=O)(Q_8)(Q_9)$, d2 and d2 are each independently an integer selected from 0 to 10, and

* and *' are each a binding site to M in Formula 1.

$Z_1$ to $Z_4$ and $Z_{11}$ to $Z_{13}$ may be the same as described in connection with $R_1$.

For example, in Formulae 3A to 3F, $CY_{11}$ is selected from a pyridine ring, a pyrimidine ring, a triazine ring, a pyrrole ring, a pyrazole ring, an imidazole ring, and a triazole ring, $CY_{12}$ and $CY_{13}$ are each independently selected from a benzene ring, a naphthalene ring, a pyridine ring, a pyrimidine ring, a triazine ring, a pyrrole ring, a pyrazole ring, an imidazole ring, and a triazole ring, $Z_1$ to $Z_4$ and $Z_{11}$ to $Z_{13}$ are each independently selected from:

hydrogen, deuterium, —F, a cyano group, a nitro group, —$SF_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group and a dibenzothiophenyl group;

a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group, each substituted with at least one selected from deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group; and —$N(Q_1)(Q_2)$, —$Si(Q_3)(Q_4)(Q_5)$, —$B(Q_6)(Q_7)$, and —$P(=O)(Q_8)(Q_9)$, $Q_1$ to $Q_9$ are each independently selected from:

—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group.

In an embodiment, ligand $L_2$ in Formula 1 may be selected from ligands represented by Formulae 3-1 to 3-15, but is not limited thereto:

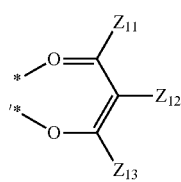
Formula 3-1

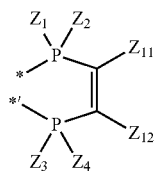
Formula 3-2

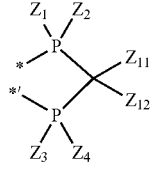
Formula 3-3

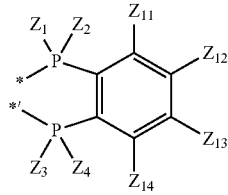
Formula 3-4

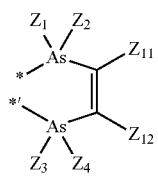
Formula 3-5

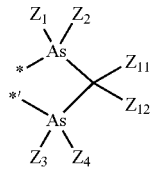
Formula 3-6

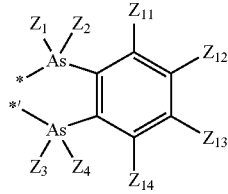
Formula 3-7

-continued

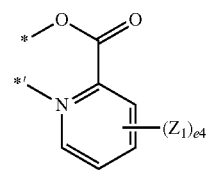
Formula 3-8

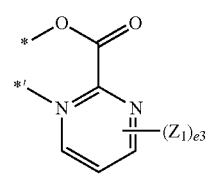
Formula 3-9

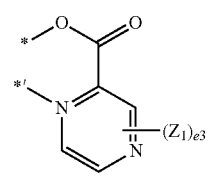
Formula 3-10

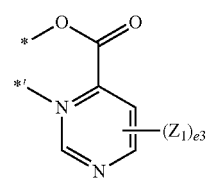
Formula 3-11

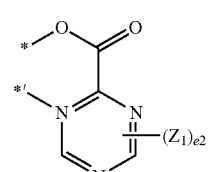
Formula 3-12

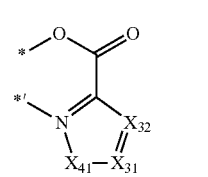
Formula 3-13

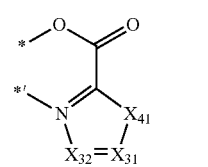
Formula 3-14

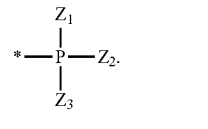
Formula 3-15

In Formulae 3-1 to 3-15,
$X_{31}$ is N or $C(Z_{1a})$, $X_{32}$ is N or $C(Z_{1b})$,
$X_{41}$ is O, S, $N(Z_{1a})$, or $C(Z_{1a})(Z_{1b})$,
descriptions of $Z_1$ to $Z_4$ and $Z_{11}$ to $Z_{14}$ are the same as described herein,
descriptions of $Z_{1a}$ and $Z_{1b}$ are the same as described in connection with $Z_1$,
e2 is 1 or 2,
e3 is an integer selected from 1 to 3,
e4 is an integer selected from 1 to 4,
* and *' each indicate a binding site to M in Formula 1.

For example, $Z_1$ to $Z_4$, $Z_{1a}$, $Z_{1b}$, and $Z_{11}$ to $Z_{14}$ in Formulae 3-1 to 3-15 may each independently be selected from:

hydrogen, deuterium, —F, a cyano group, a nitro group, —$SF_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group;

a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group, each substituted with at least one selected from deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group; and —$N(Q_1)(Q_2)$, —$Si(Q_3)(Q_4)(Q_5)$, —$B(Q_6)(Q_7)$, and —$P(=O)(Q_8)(Q_9)$, $Q_1$ to $Q_9$ are each independently selected from:

—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group, but they are not limited thereto.

In an embodiment, ligand $L_1$ in Formula 1 may be selected from ligands represented by Formulae 2A-1 to 2A-4 and 2B-1 to 2B-3, and ligand $L_2$ in Formula 1 may be selected from ligands represented by Formulae 3A to 3F (for example, ligands represented by Formulae 3-1 to 3-15).

In some embodiments, ligand $L_1$ in Formula 1 may be selected from ligands represented by Formulae 2A-1(1) to 2A-1(6), and ligand $L_2$ in Formula 1 may be selected from ligands represented by Formulae 3A to 3F (for example, ligands represented by Formulae 3-1 to 3-15).

In some embodiments, ligand $L_1$ in Formula 1 may be selected from ligands represented by Formulae 4-1 to 4-7, 4-11 to 4-17, 4-21 to 4-27, 4-31 to 4-37, 4-41 to 4-44, 4-51 to 4-54, 4-61 to 4-64, and 4-71 to 4-74, and ligand $L_2$ in Formula 1 may be selected from ligands represented by Formulae 3A to 3F (for example, ligands represented by Formulae 3-1 to 3-15).

The organometallic compound may be one of Compounds 1 to 68:

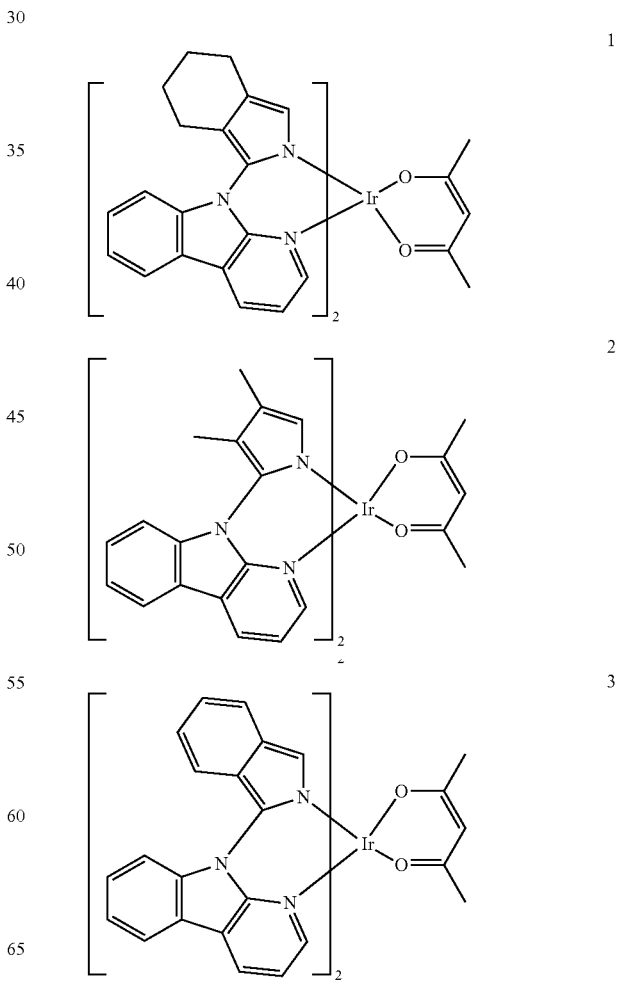

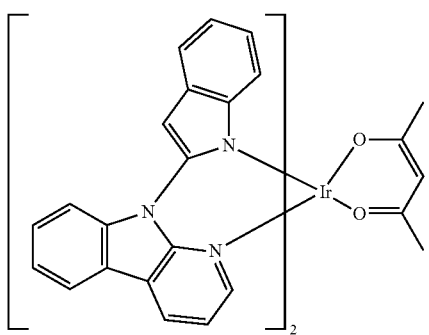
4
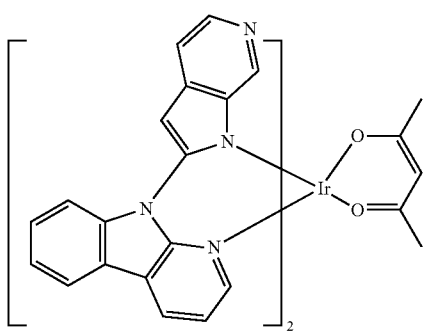
5
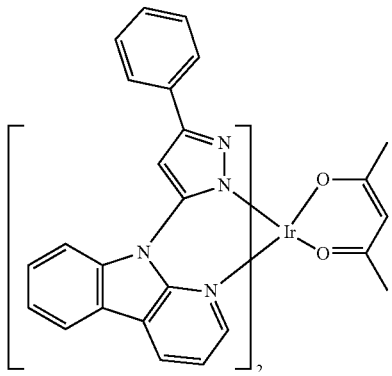
6
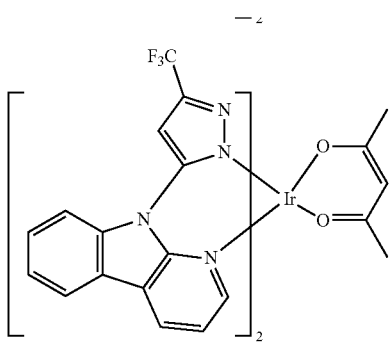
7
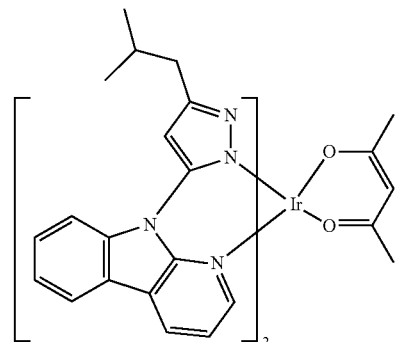
8
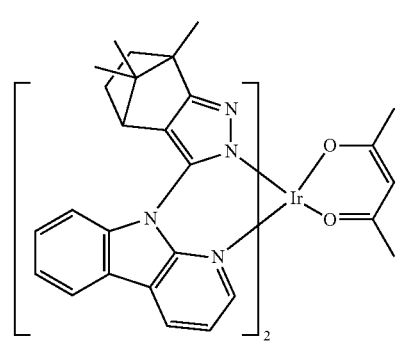
9
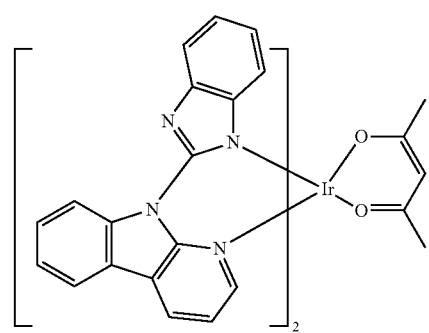
10
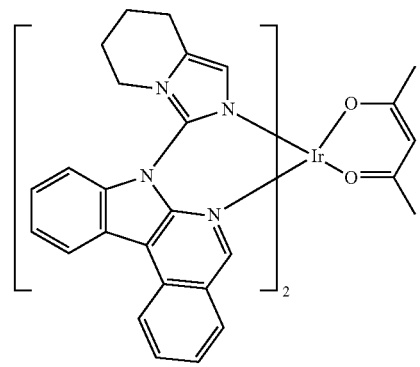
11

12
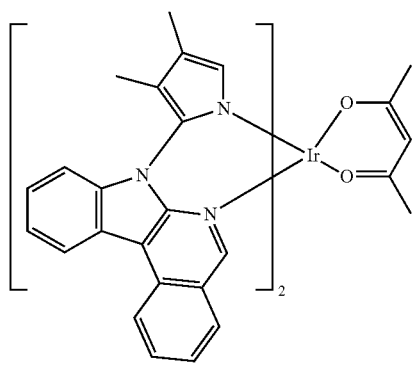
13
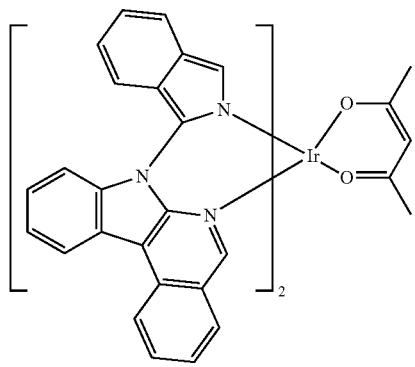
14
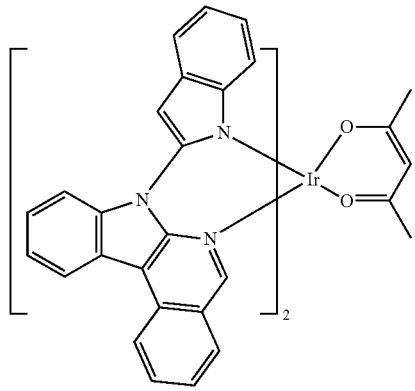
15
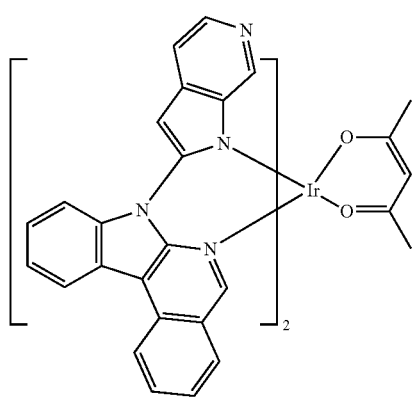
16
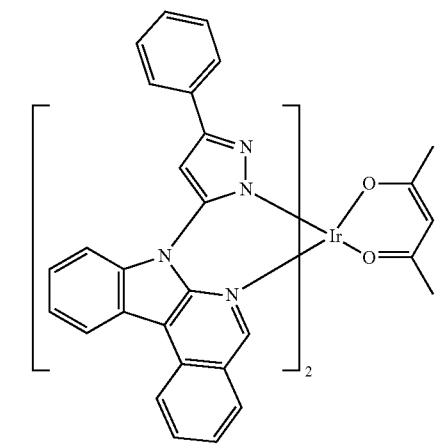
17
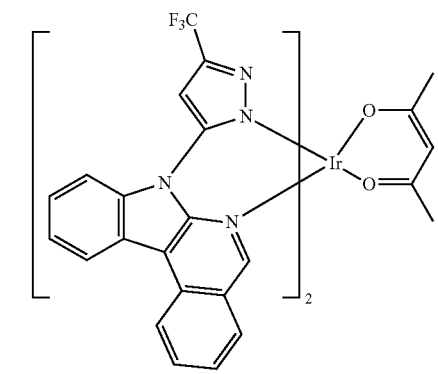
18
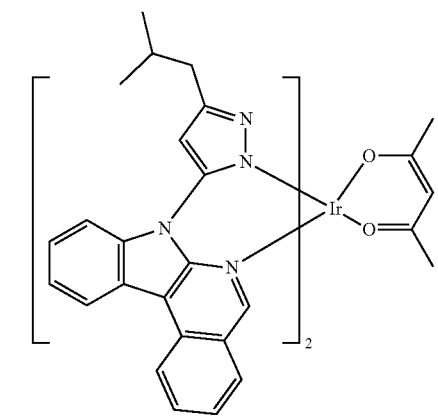
19
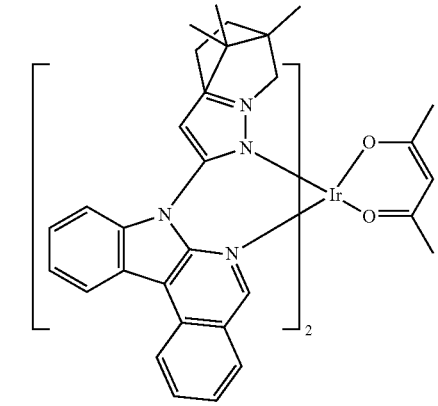

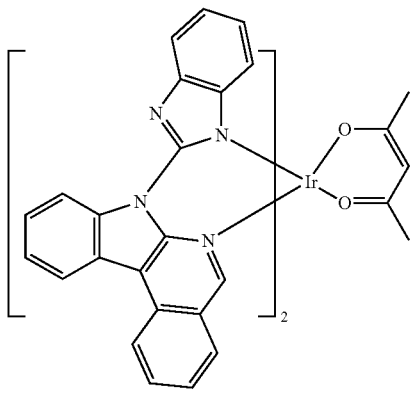
20
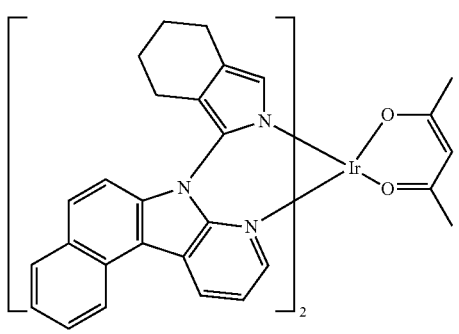
21
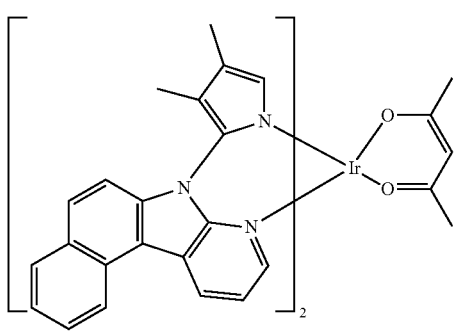
22
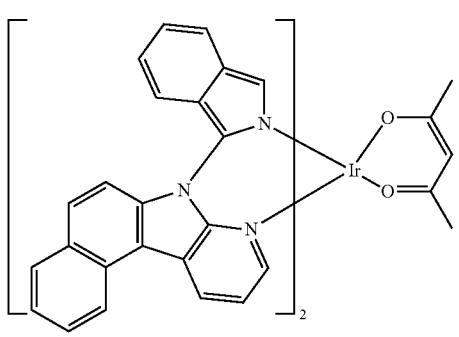
23
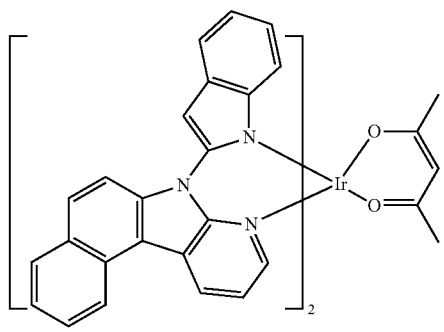
24
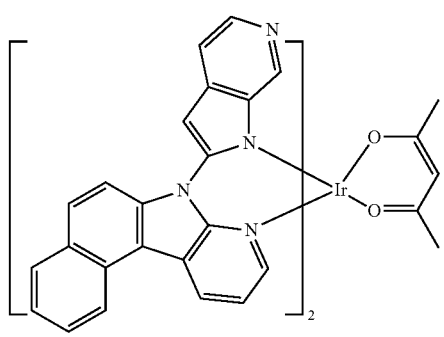
25
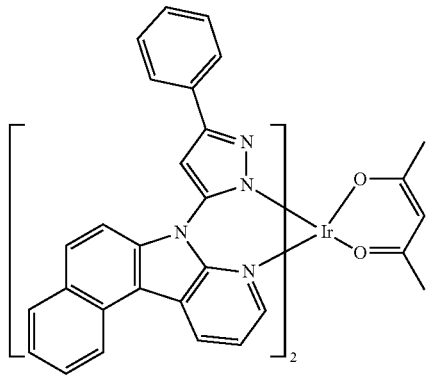
26
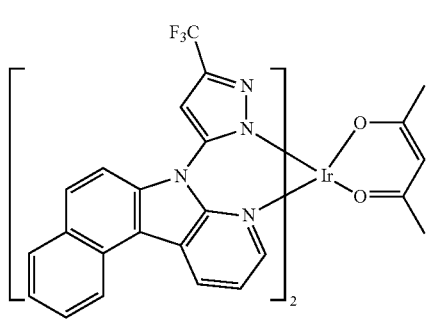
27

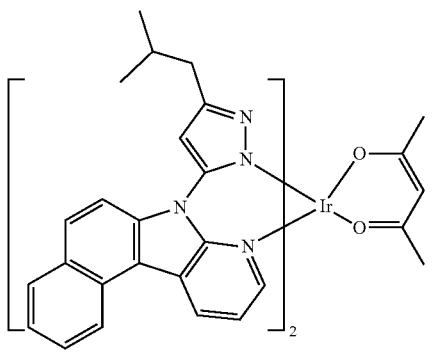
28
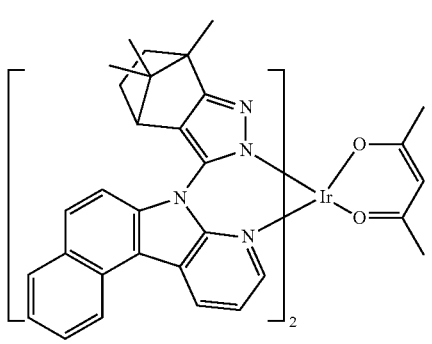
29
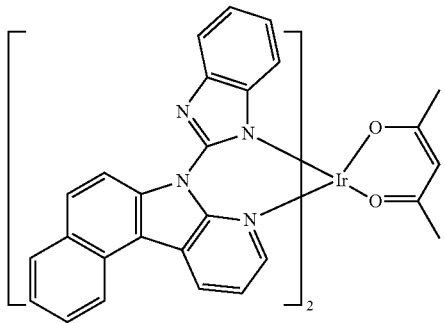
30
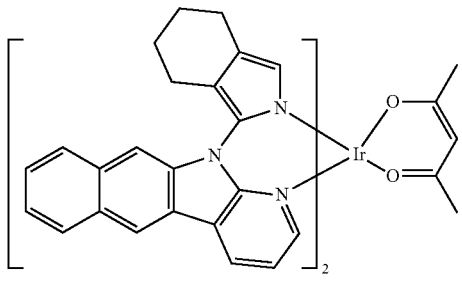
31
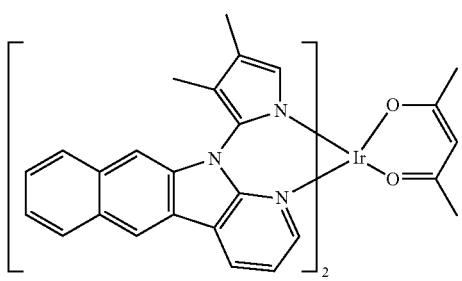
32
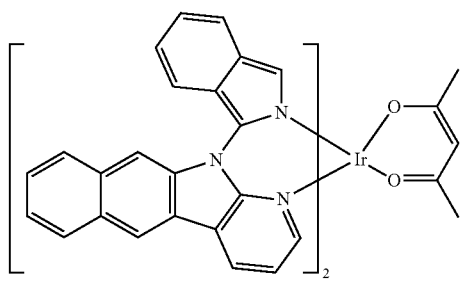
33
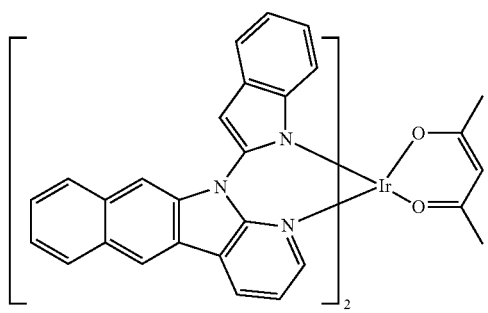
34
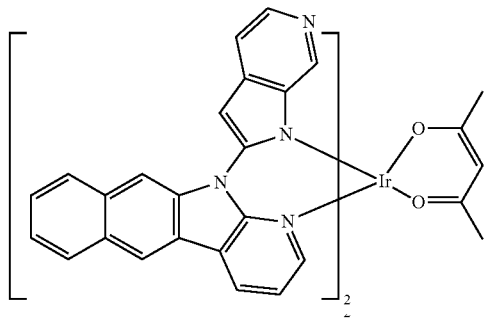
35
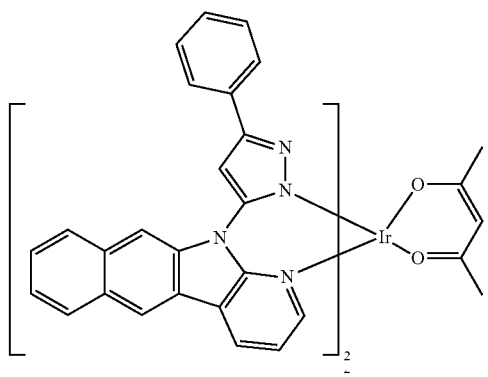
36
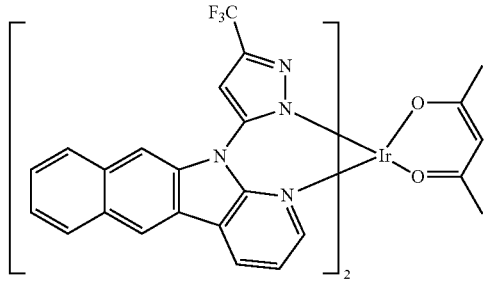
37

38
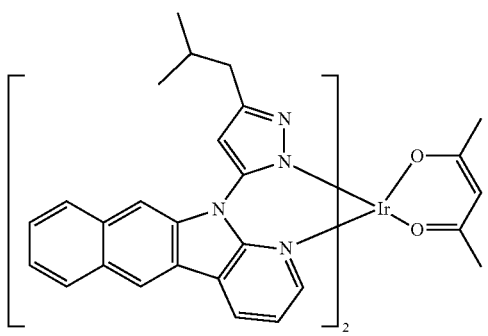
39
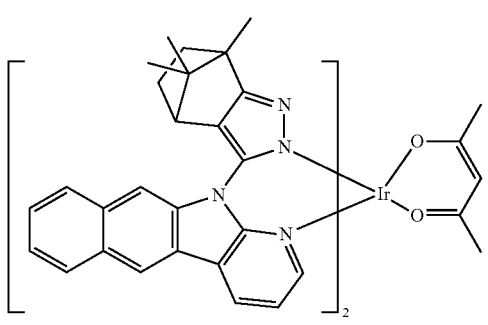
40
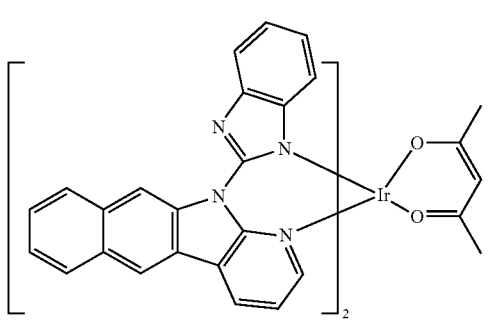
41
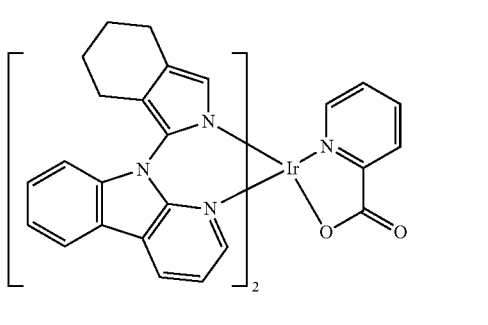
42
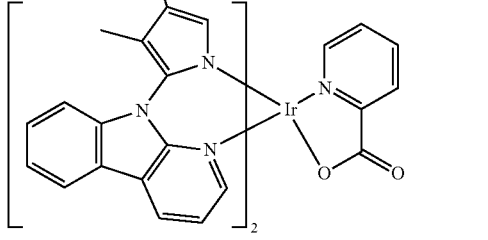
43
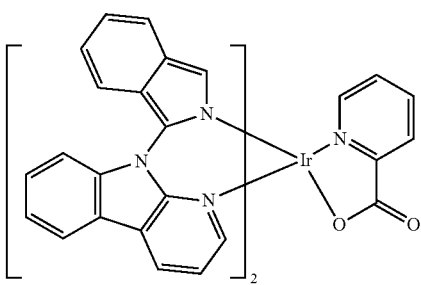
44
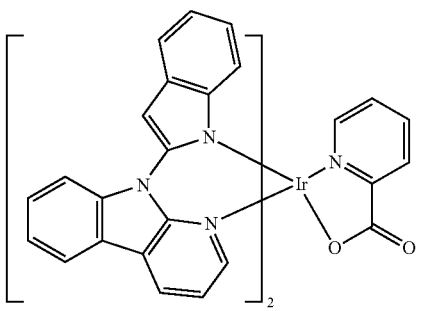
45
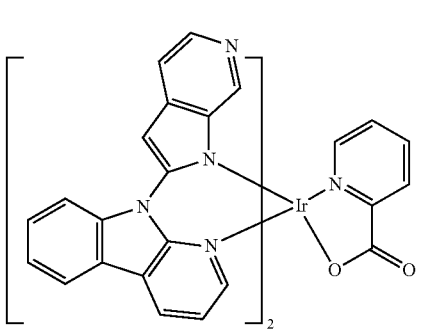
46
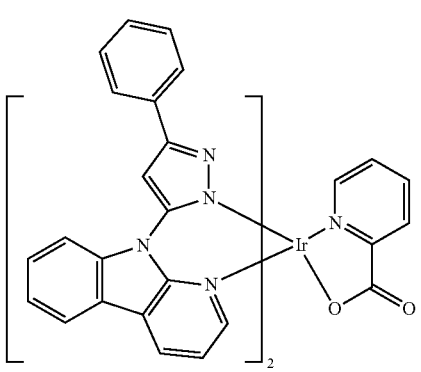
47
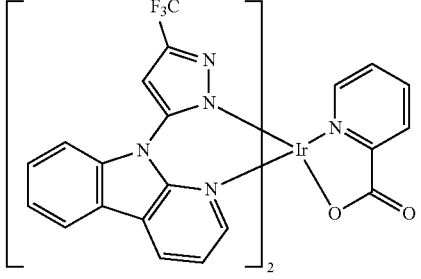

48
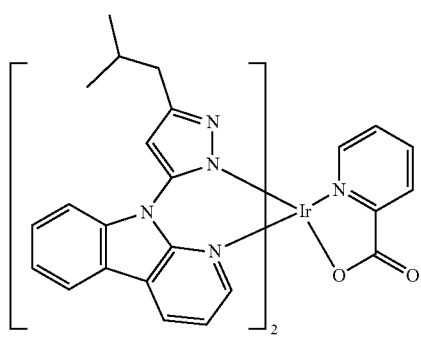
49
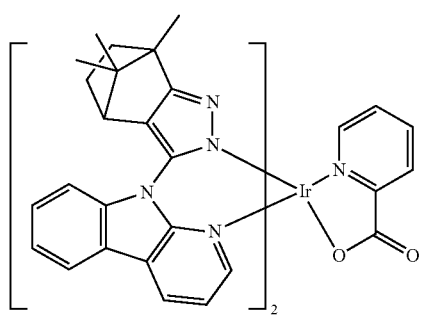
50
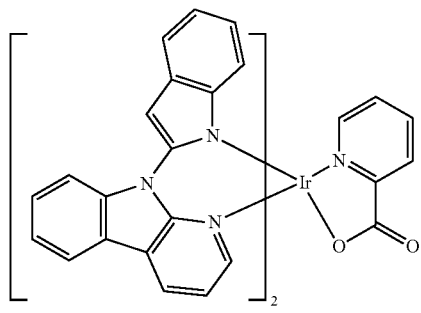
51
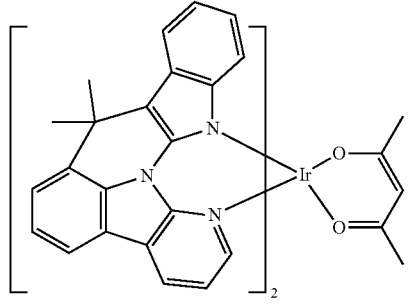
52
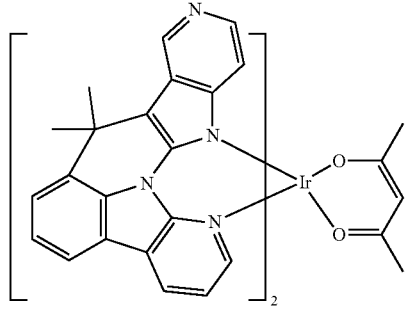
53
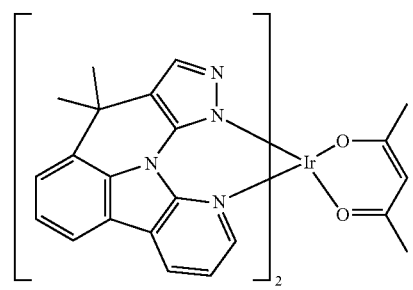
54
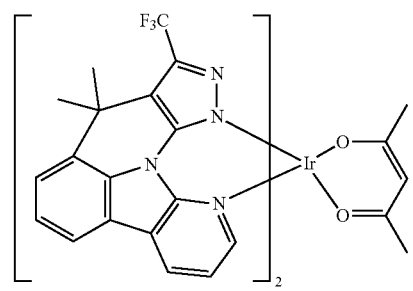
55
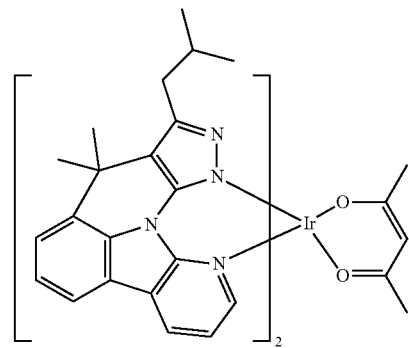
56
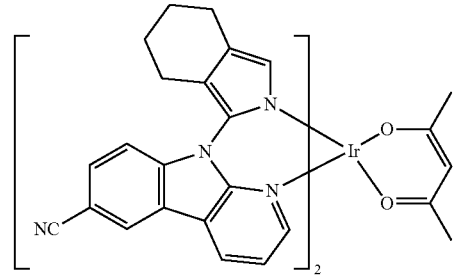
57
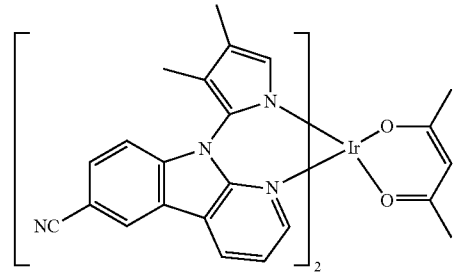

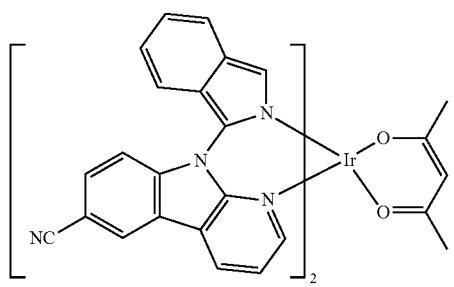
58
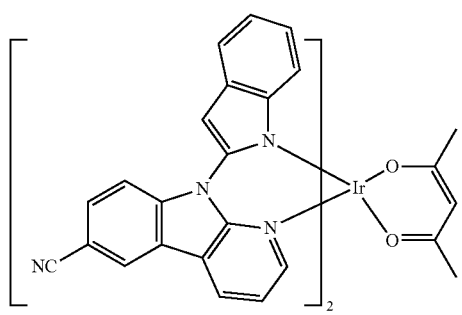
59
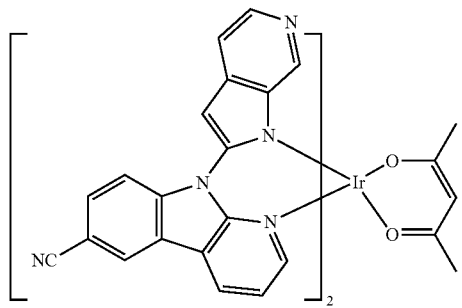
60
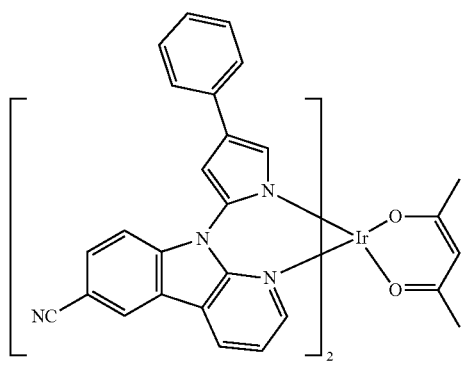
61
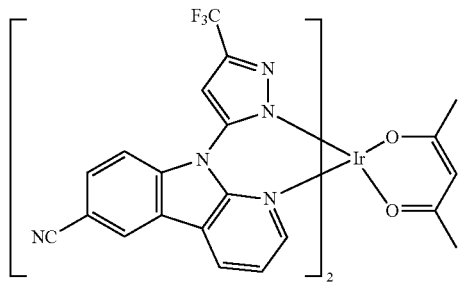
62
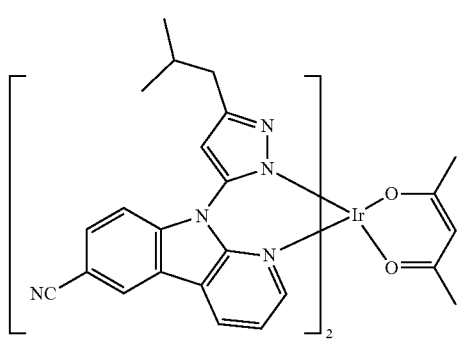
63
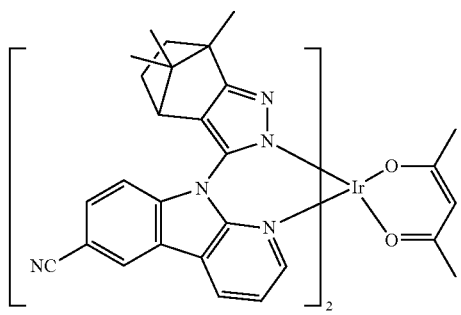
64
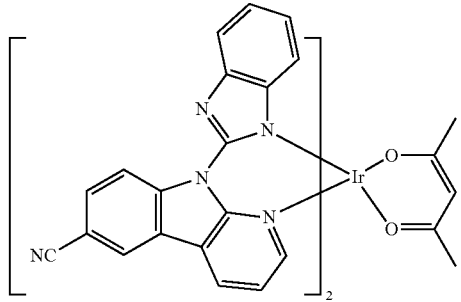
65
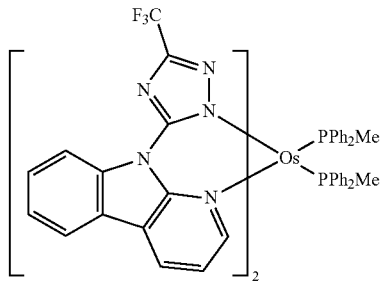
66
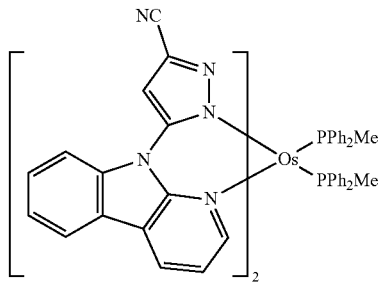
67

-continued

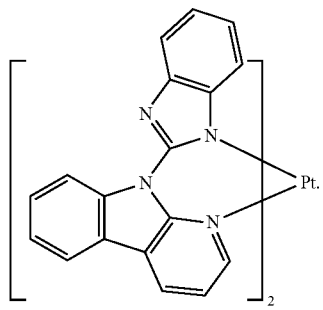

68

Regarding the organometallic compound represented by Formula 1, ligand $L_1$ may be selected from a ligand represented by Formula 2A or 2B.

Nitrogen of a carboline-based ring in Formulae 2A and 2B is bound to M in Formula 1, and ring $CY_1$ in Formulae 2A and 2B is bound to M in Formula 1 via nitrogen. Accordingly, the organometallic compound represented by Formula 1 may have high luminescent efficiency.

For example, HOMO, LUMO, singlet ($S_1$), and triplet ($T_1$) energy levels of some of the organometallic compounds were evaluated by using a DFT method of Gaussian program (structurally optimized at a level of B3LYP, 6-31G(d,p)), and results thereof are shown in Table 1 below.

TABLE 1

| Compound No. | HOMO (eV) | LUMO (eV) | $T_1$ energy level (eV) |
|---|---|---|---|
| 3 | −4.208 | −1.705 | 1.860 |
| 4 | −4.508 | −1.769 | 2.140 |
| 9 | −4.941 | −1.580 | 2.593 |
| 10 | −5.084 | −1.842 | 2.551 |
| 19 | −4.938 | −1.949 | 2.225 |
| 49 | −4.831 | −1.828 | 2.366 |
| 66 | −4.508 | −1.547 | 2.203 |
| 68 | −5.246 | −2.028 | 2.545 |
| Comparative Compound 1 | −4.691 | −1.298 | 2.528 |

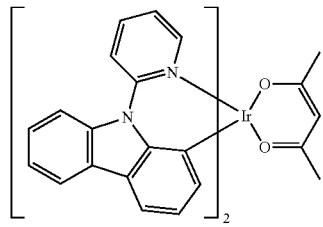

Comparative Compound 1

Referring to Table 1, it can be seen that the organometallic compound represented by Formula 1 has electronic characteristics that are suitable for a material for an electronic device, for example, a dopant for an organic light-emitting device.

Synthesis methods of the organometallic compound represented by Formula 1 may be recognizable by one of ordinary skill in the art by referring to Synthesis Examples provided below.

The organometallic compound represented by Formula 1 is suitable for use in an organic layer of an organic light-emitting device, for example, for use as a dopant in an emission layer of the organic layer. Thus, another aspect provides an organic light-emitting device that includes:

a first electrode;
a second electrode; and
an organic layer that is disposed between the first electrode and the second electrode,
wherein the organic layer includes an emission layer and at least one organometallic compound represented by Formula 1.

The organic light-emitting device may have, due to the inclusion of an organic layer including the organometallic compound represented by Formula 1, excellent driving voltage, efficiency, power, electroluminescent (EL) emission wavelength, and color purity characteristics.

The organometallic compound represented by Formula 1 may be used between a pair of electrodes of an organic light-emitting device. For example, the organometallic compound represented by Formula 1 may be included in the emission layer. In this regard, the organometallic compound may act as a dopant, and the emission layer may further include a host (that is, an amount of the organometallic compound represented by Formula 1 is smaller than an amount of the host).

The expression that "(an organic layer) includes at least one of organometallic compounds" as used herein may include an embodiment in which "(an organic layer) includes identical organometallic compounds represented by Formula 1 and an embodiment in which (an organic layer) includes two or more different organometallic compounds represented by Formula 1.

For example, the organic layer may include only Compound 1 as the organometallic compound. In this regard, Compound 1 may be included only in the emission layer of the organic light-emitting device. In some embodiments, the organic layer may include, as the organometallic compound, Compound 1 and Compound 2. In this regard, Compound 1 and Compound 2 may be included in an identical layer (for example, Compound 1 and Compound 2 all may be included in an emission layer).

The first electrode may be an anode, which is a hole injection electrode, and the second electrode may be a cathode, which is an electron injection electrode; or the first electrode may be a cathode, which is an electron injection electrode, and the second electrode may be an anode, which is a hole injection electrode.

For example, in the organic light-emitting device, the first electrode may be an anode, the second electrode may be a cathode, and the organic layer may further include a hole transport region disposed between the first electrode and the emission layer and an electron transport region disposed between the emission layer and the second electrode, wherein the hole transport region may include at least one selected from a hole injection layer, a hole transport layer, and an electron blocking layer, and wherein the electron transport region may include at least one selected from a hole blocking layer, an electron transport layer, and an electron injection layer.

The term "organic layer" as used herein refers to a single layer and/or a plurality of layers disposed between the first electrode and the second electrode of the organic light-emitting device. The "organic layer" may include, in addition to an organic compound, an organometallic complex including metal.

FIG. 1 is a schematic cross-sectional view of an organic light-emitting device 10 according to an embodiment. Hereinafter, the structure of an organic light-emitting device according to an embodiment and a method of manufacturing an organic light-emitting device according to an embodiment will be described in connection with FIG. 1. The organic light-emitting device 10 includes a first electrode 11, an organic layer 15, and a second electrode 19, which are sequentially stacked.

A substrate may be additionally disposed under the first electrode 11 or above the second electrode 19. For use as the substrate, any substrate that is used in general organic light-emitting devices may be used, and the substrate may be a glass substrate having excellent mechanical strength, thermal stability, transparency, surface smoothness, ease of handling, and water-resistance, or a transparent plastic substrate.

The first electrode 11 may be formed by depositing or sputtering a material for forming the first electrode 11 on the substrate. The first electrode 11 may be an anode. The material for the first electrode 11 may be selected from materials with a high work function to facilitate hole injection. The first electrode 11 may be a reflective electrode, a semi-transmissive electrode, or a transmissive electrode. The material for the first electrode may be, for example, indium tin oxide (ITO), indium zinc oxide (IZO), tin oxide ($SnO_2$), and zinc oxide (ZnO). In some embodiments, magnesium (Mg), aluminum (Al), aluminum-lithium (Al—Li), calcium (Ca), magnesium-indium (Mg—In), or magnesium-silver (Mg—Ag) may be used as the material for the first electrode.

The first electrode 11 may have a single-layer structure or a multi-layer structure including two or more layers. For example, the first electrode 11 may have a three-layered structure of ITO/Ag/ITO, but the structure of the first electrode 110 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In some embodiments, the hole transport region may have a structure of hole injection layer/hole transport layer or hole injection layer/hole transport layer/electron blocking layer, which are sequentially stacked in this stated order from the first electrode 11.

A hole injection layer may be formed on the first electrode 11 by using one or more methods selected from vacuum deposition, spin coating, casting, or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100 to about 500° C., a vacuum pressure of about $10^{-8}$ to about $10^{-3}$ torr, and a deposition rate of about 0.01 to about 100 Angstroms per second (Å/sec). However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4', 4"-tris(N-carbazolyl)triphenylamine (TCTA), polyaniline/dodecylbenzene sulfonic acid (PANI/DBSA), poly(3,4-ethylenedioxythiophene)/poly(4-styrenesulfonate) (PEDOT/PSS), polyaniline/camphor sulfonic acid (PANI/CSA), (polyaniline)/poly(4-styrenesulfonate) (PANI/PSS), a compound represented by Formula 201 below, and a compound represented by Formula 202 below:

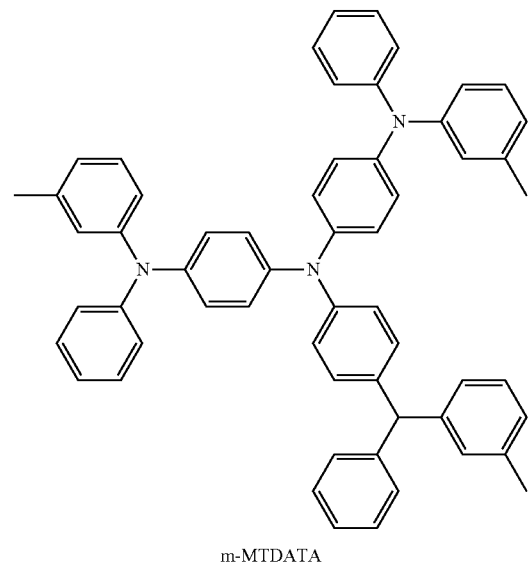

m-MTDATA

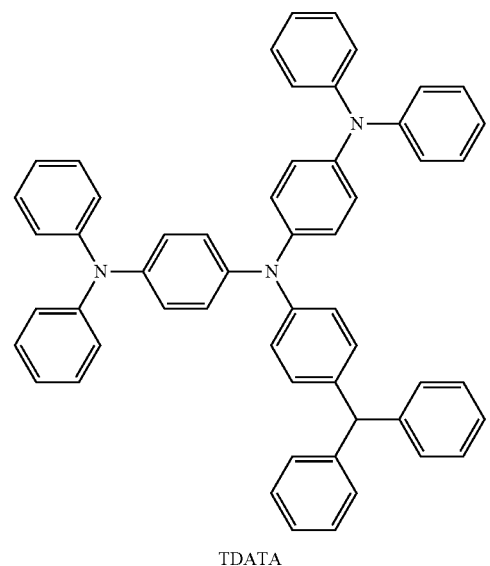

TDATA

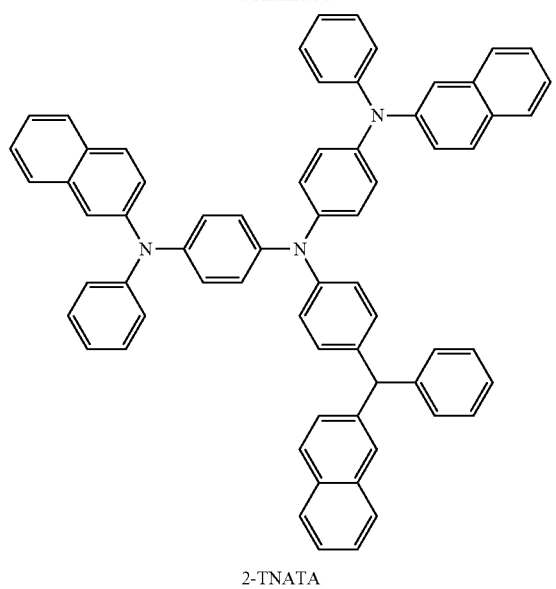
2-TNATA
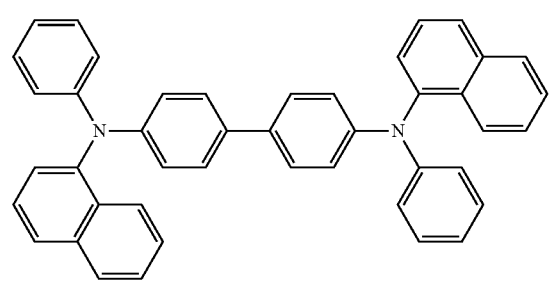
NPB
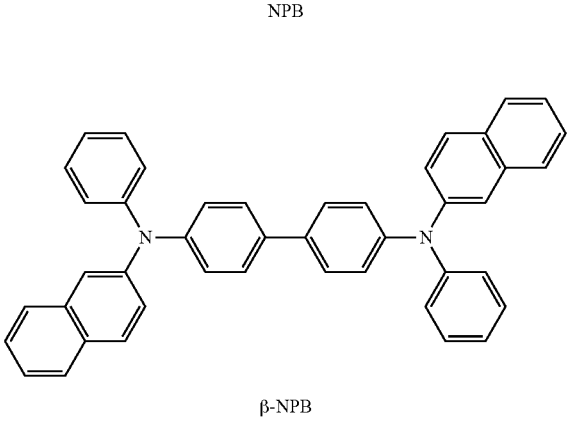
β-NPB
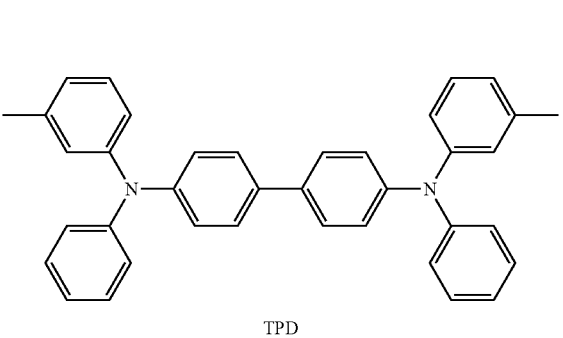
TPD
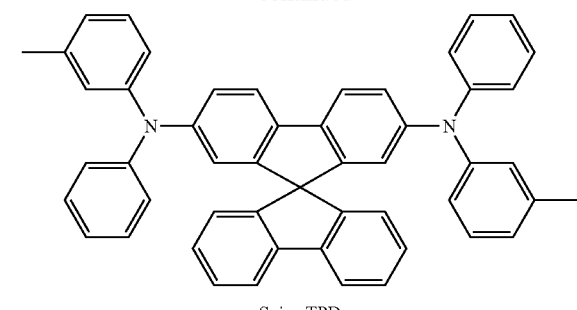
Spiro-TPD
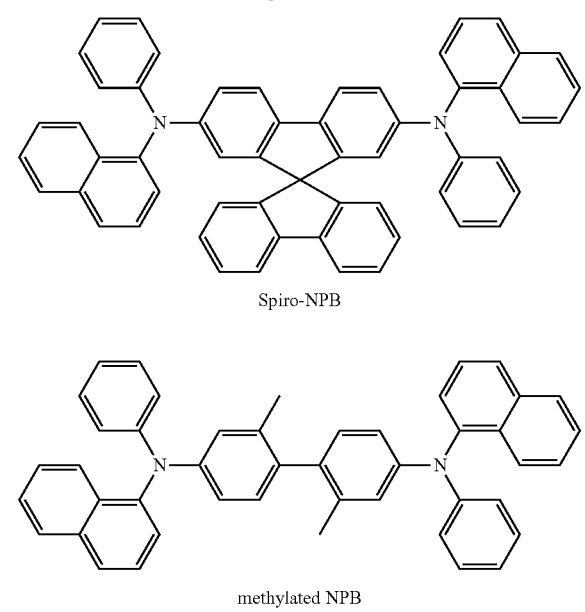
Spiro-NPB
methylated NPB
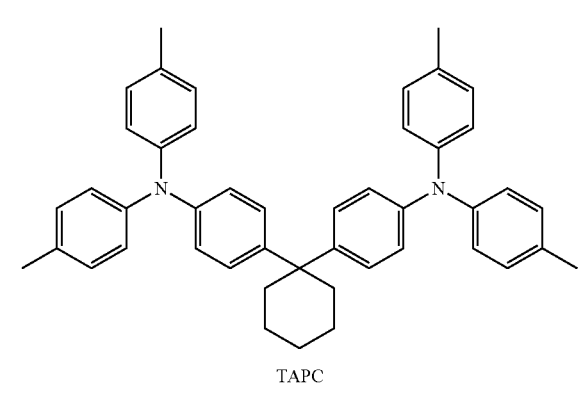
TAPC
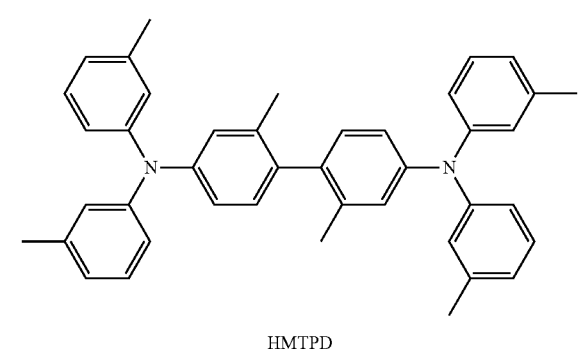
HMTPD -continued Formula 201

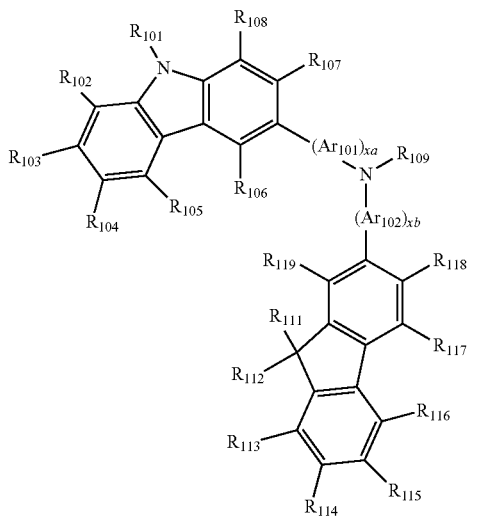

Formula 202

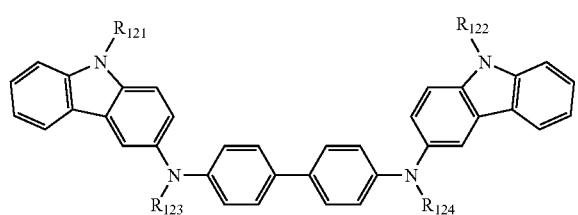

$Ar_{101}$ and $Ar_{102}$ in Formula 201 may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may each independently be an integer selected from 0 to 5, or 0, 1, or 2. For example, xa may be 1 and xb may be 0, but they are not limited thereto.

$R_{101}$ to $R_{108}$, $R_{111}$ to $R_{110}$, and $R_{121}$ to $R_{124}$ in Formulae 201 and 202 may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, and so on), or a $C_1$-$C_{10}$ alkoxy group (for example, a methoxy group, an ethoxy group, a propoxy group, a butoxy group, a pentoxy group, and so on);

a $C_1$-$C_{10}$ alkyl group or a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but they are not limited thereto.

$R_{109}$ in Formula 201 may be a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

According to an embodiment, the compound represented by Formula 201 may be represented by Formula 201A, but is not limited thereto:

Formula 201A

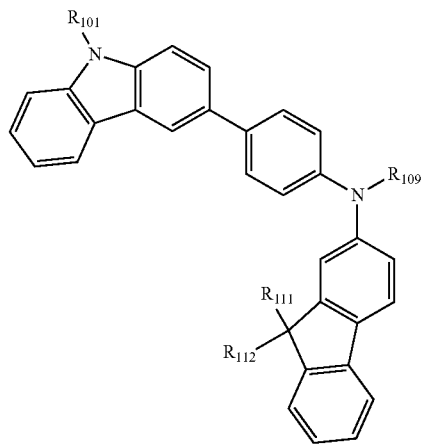

$R_{101}$, $R_{111}$, $R_{112}$, and $R_{109}$ in Formula 201A may be understood by referring to the description provided herein.

For example, the compound represented by Formula 201, and the compound represented by Formula 202 may include compounds HT1 to HT20 illustrated below, but are not limited thereto.

HT1
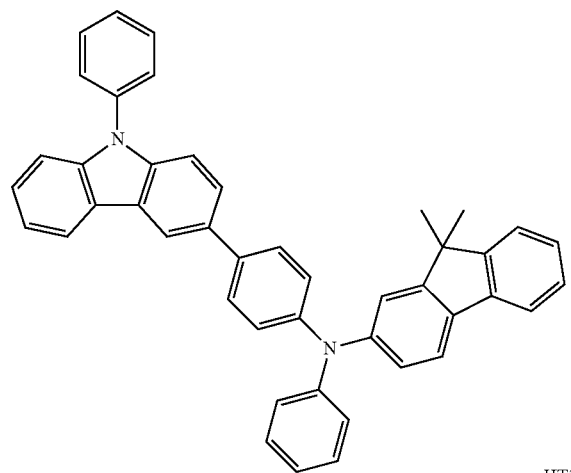
HT2
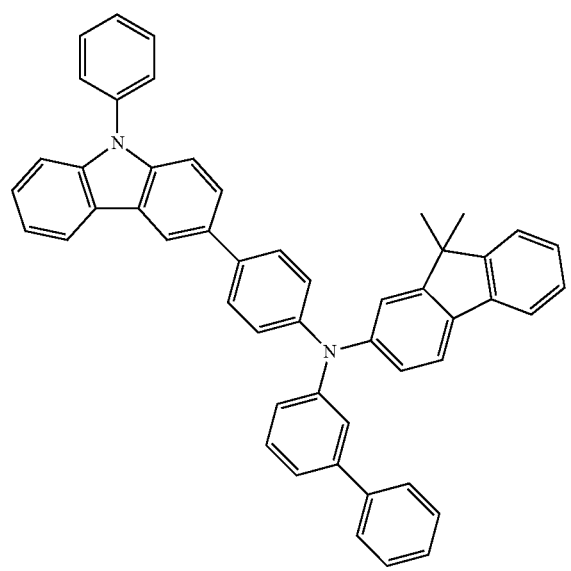
HT4
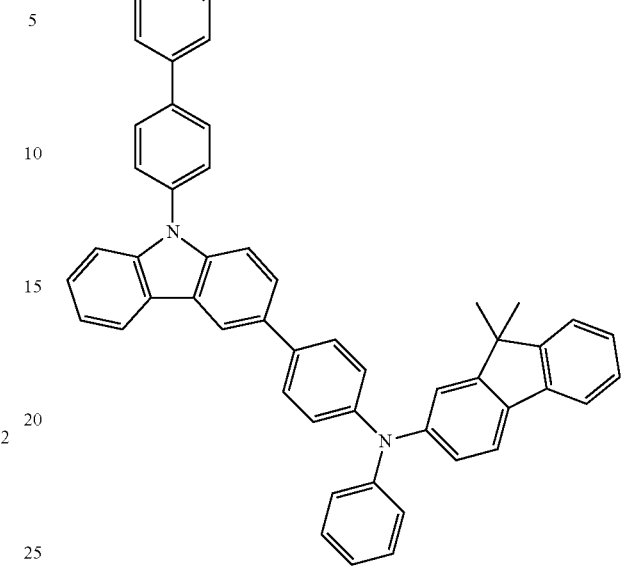
HT3
HT5
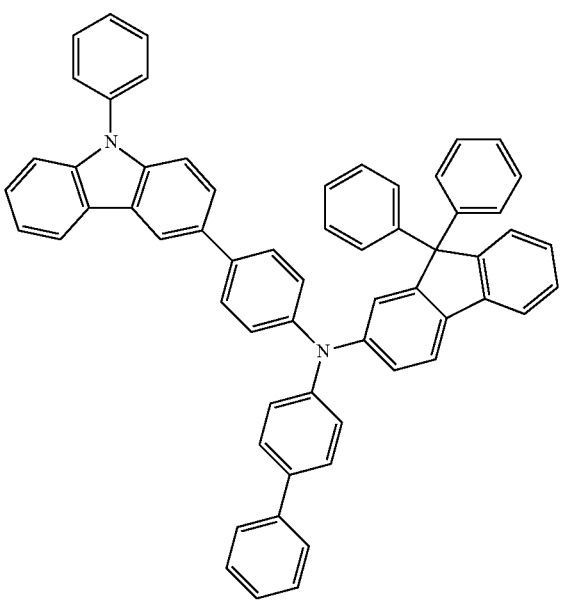

HT6
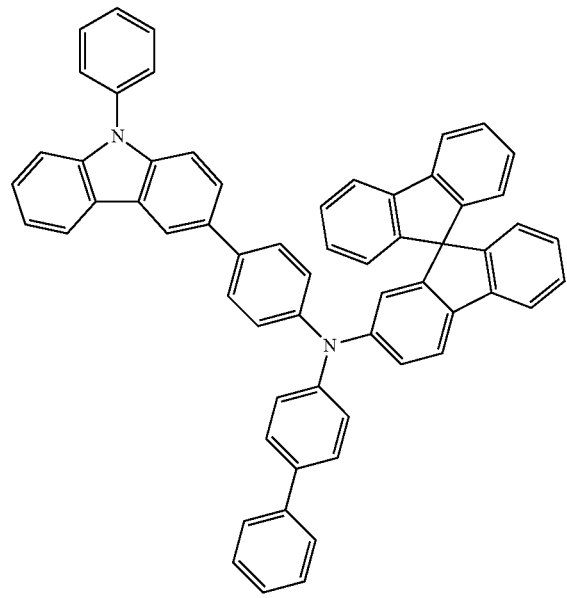
HT7
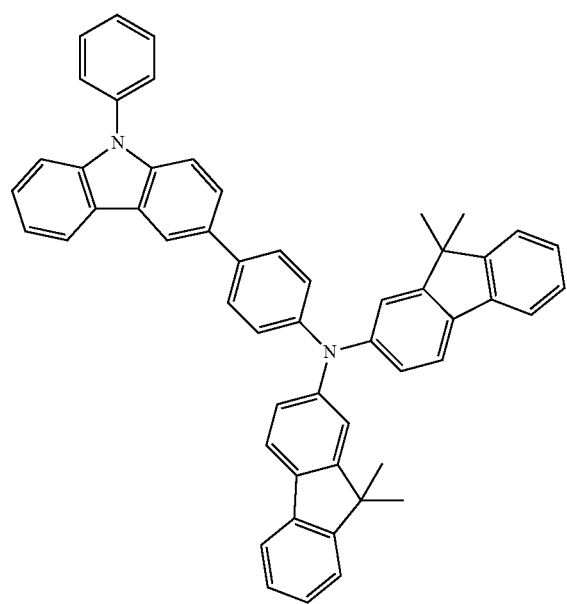
HT8
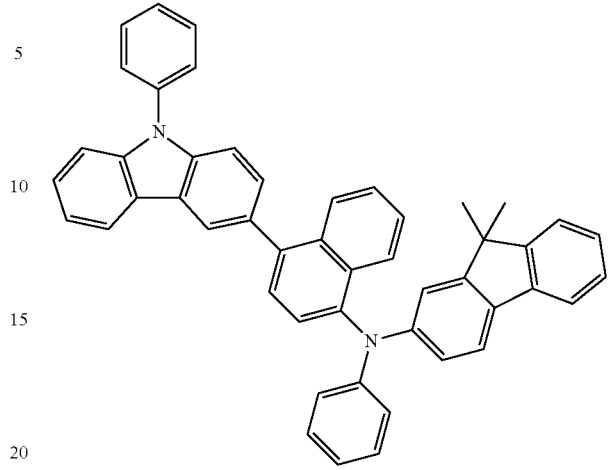
HT9
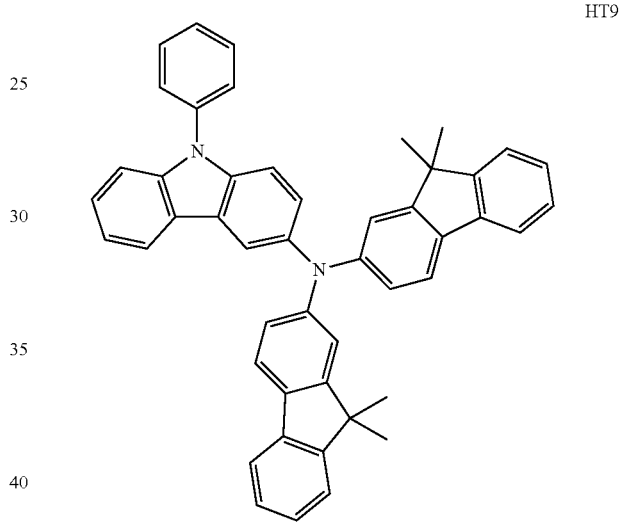
HT10
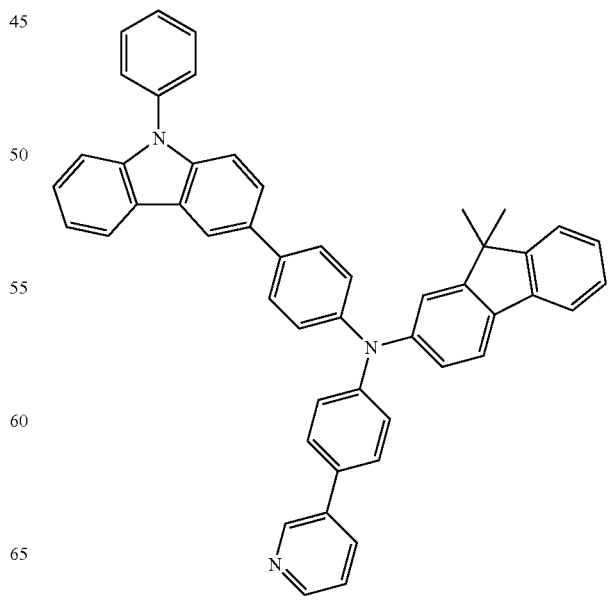

HT11
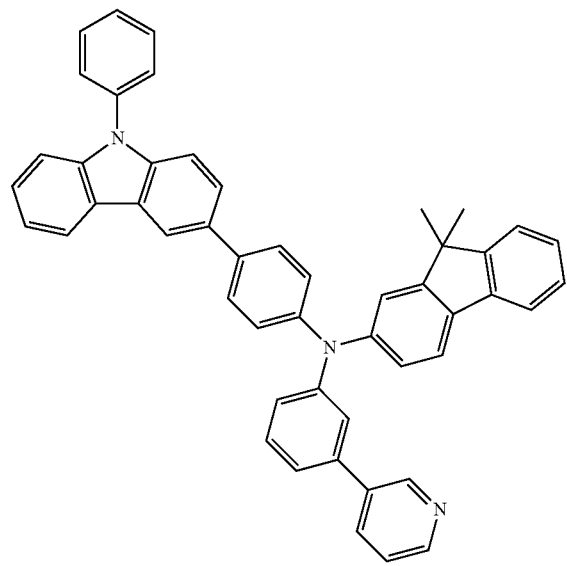
HT14
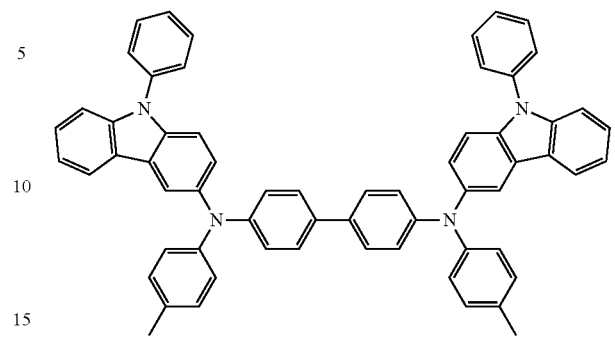
HT15
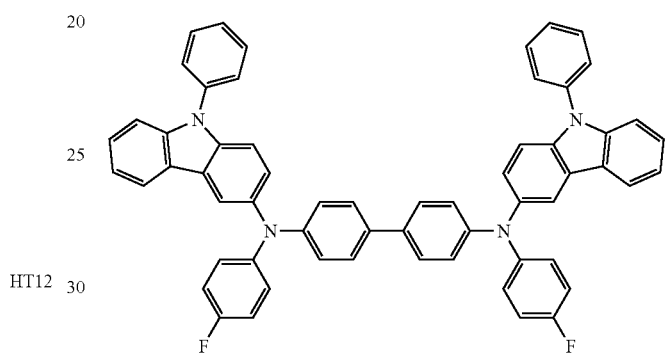
HT12
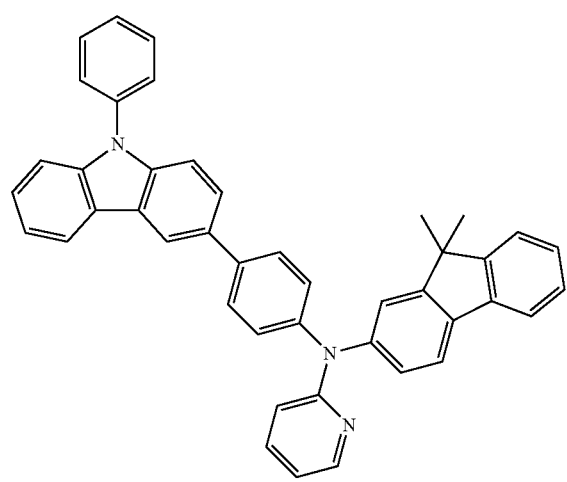
HT16
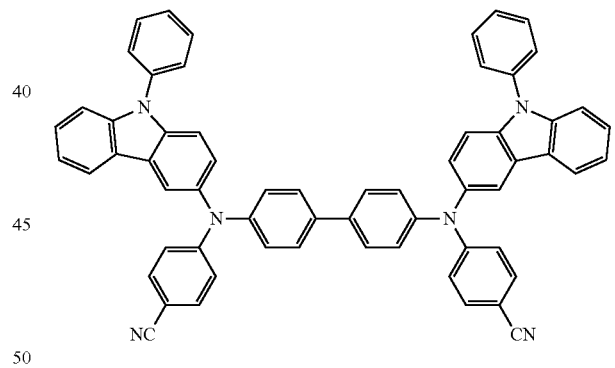
HT13
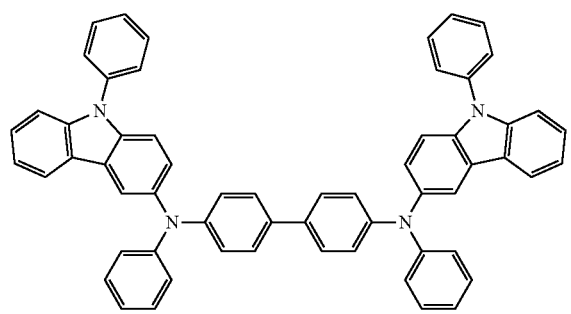
HT17
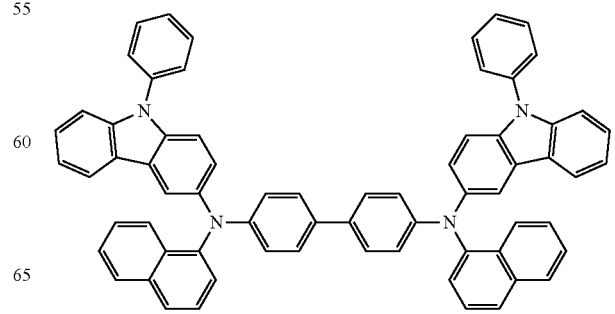

-continued

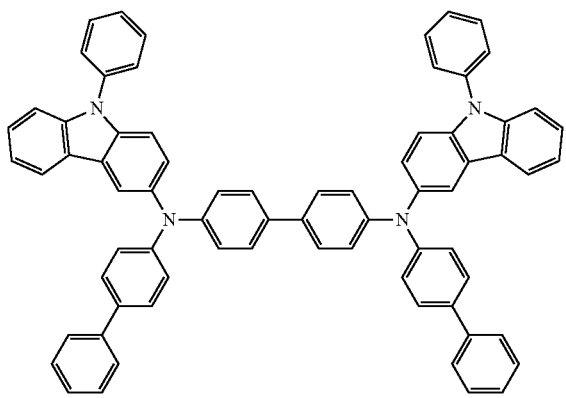

HT18

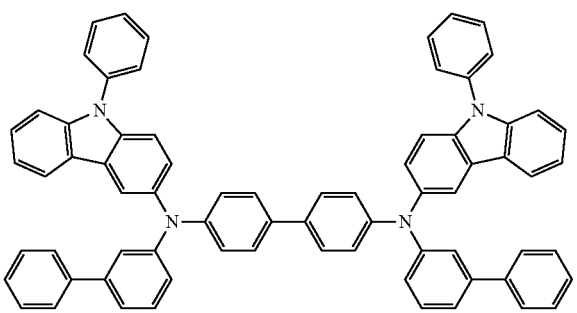

HT19

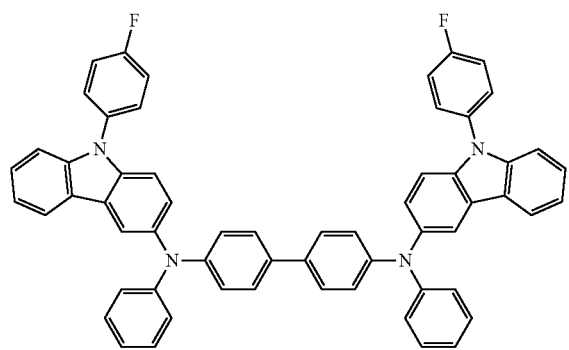

HT20

A thickness of the hole transport region may be in a range of about 100 Å to about 10,000 Å, for example, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. While not wishing to be bound by theory, it is understood that when the thicknesses of the hole transport region, the hole injection layer and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 below, but are not limited thereto.

Compound HT-D1

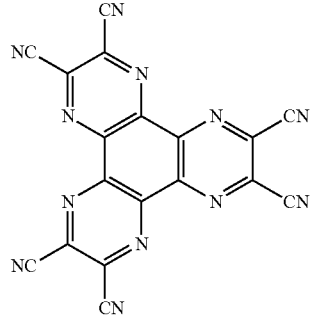

F4-TCNQ

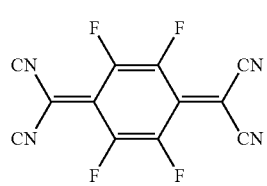

The hole transport region may include a buffer layer.

Also, the buffer layer may compensate for an optical resonance distance according to a wavelength of light emitted from the emission layer, and thus, efficiency of a formed organic light-emitting device may be improved.

Then, an emission layer (EML) may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary according to the material that is used to form the emission layer.

Meanwhile, when the hole transport region includes an electron blocking layer, a material for the electron blocking layer may be selected from materials for the hole transport region described above and materials for a host to be explained later. However, the material for the electron blocking layer is not limited thereto. For example, when the hole transport region includes an electron blocking layer, a material for the electron blocking layer may be mCP, which will be explained later.

The emission layer may include a host and a dopant, and the dopant may include the organometallic compound represented by Formula 1.

The host may include at least one selected from TPBi, TBADN, ADN (also referred to as "DNA"), CBP, CDBP, TCP, mCP, Compound H50, and Compound H51:

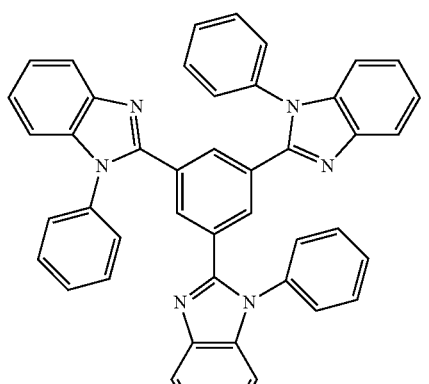
TPBi
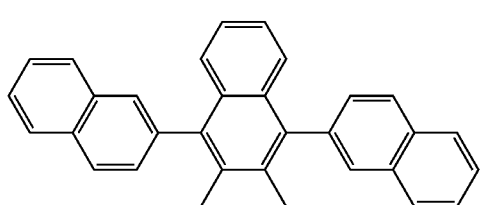
TBADN
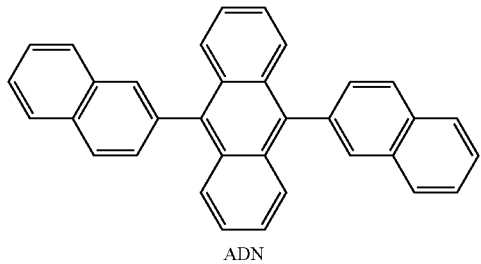
ADN
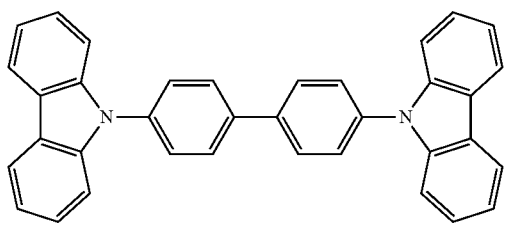
CBP
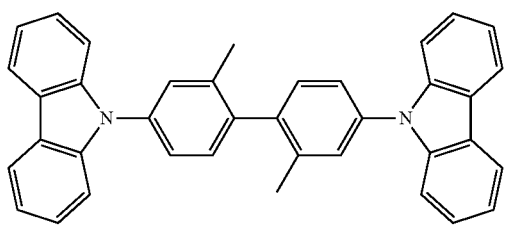
CDBP
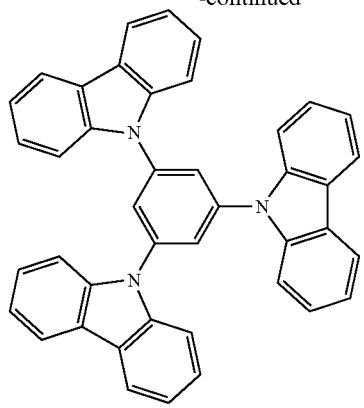
TCP
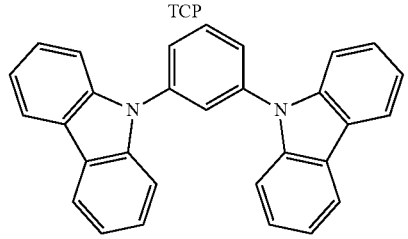
mCP
Compound H50
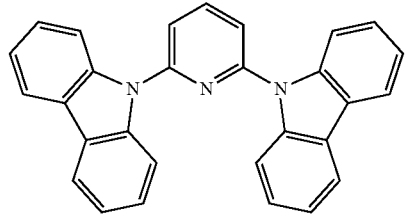
Compound H51
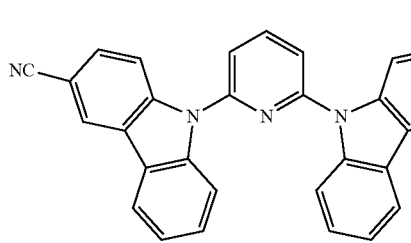
In some embodiments, the host may further include a compound represented by Formula 301 below.
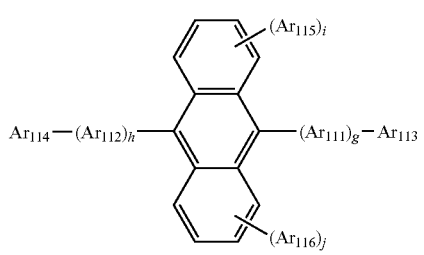
Formula 301
$Ar_{111}$ and $Ar_{112}$ in Formula 301 may each independently be selected from
a phenylene group, a naphthylene group, a phenanthrenylene group, and a pyrenylene group; and a phenylene group, a naphthylene group, a phenanthrenylene group, and a pyrenylene group, each substituted with at least one selected from a phenyl group, a naphthyl group, and an anthracenyl group.

$Ar_{113}$ to $Ar_{116}$ in Formula 301 may each independently be selected from a $C_1$-$C_{10}$ alkyl group, a phenyl group, a naphthyl group, a phenanthrenyl group, and a pyrenyl group; and a phenyl group, a naphthyl group, a phenanthrenyl group, and a pyrenyl group, each substituted with at least one selected from a phenyl group, a naphthyl group, and an anthracenyl group.

g, h, i, and j in Formula 301 may be each independently an integer selected from 0 to 4, and may be, for example, 0, 1, or 2.

$Ar_{113}$ to $Ar_{116}$ in Formula 301 may be each independently selected from a $C_1$-$C_{10}$ alkyl group, substituted with at least one selected from a phenyl group, a naphthyl group, and an anthracenyl group;

a phenyl group, a naphthyl group, an anthracenyl group, a pyrenyl group, a phenanthrenyl group, and a fluorenyl group;

a phenyl group, a naphthyl group, an anthracenyl group, a pyrenyl group, a phenanthrenyl group, and a fluorenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a pyrenyl group, a phenanthrenyl group, and a fluorenyl group; and

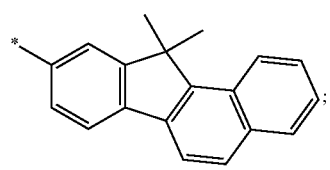 [SMILES: *c1ccc2c(c1)C(C)(C)c1c-2ccc2ccccc12]

but embodiments are not limited thereto.

In some embodiments, the host may include a compound represented by Formula 302 below:

Formula 302

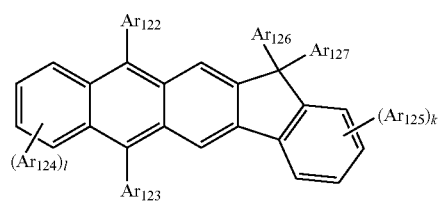

$Ar_{122}$ to $Ar_{125}$ in Formula 302 are the same as described in detail in connection with $Ar_{113}$ in Formula 301.

$Ar_{126}$ and $Ar_{127}$ in Formula 302 may be each independently a $C_1$-$C_{10}$ alkyl group (for example, a methyl group, an ethyl group, or a propyl group).

k and l in Formula 302 may be each independently an integer of 0 to 4. For example, k and l may be 0, 1, or 2.

The compound represented by Formula 301 and the compound represented by Formula 302 may include Compounds H1 to H42 illustrated below, but are not limited thereto.

H1
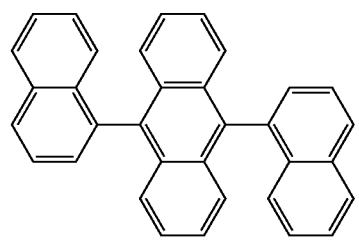

H2
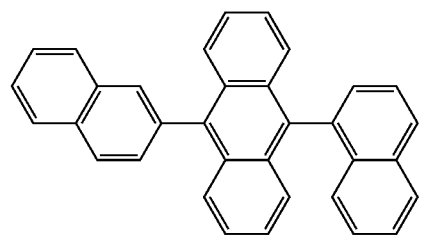

H3
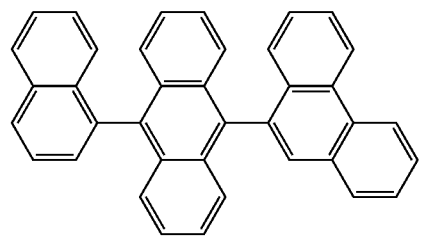

H4
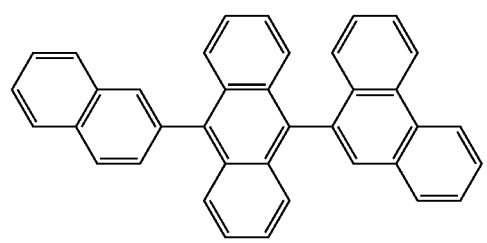

H5
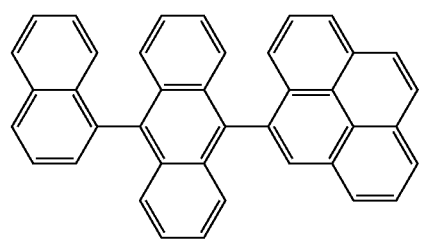

H6
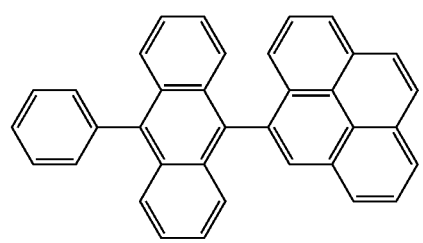

-continued
H7
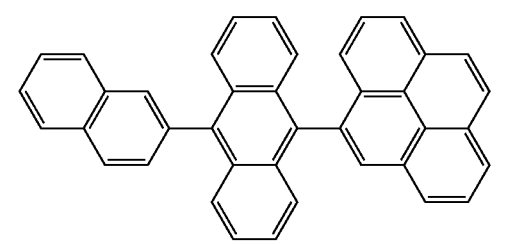
H8
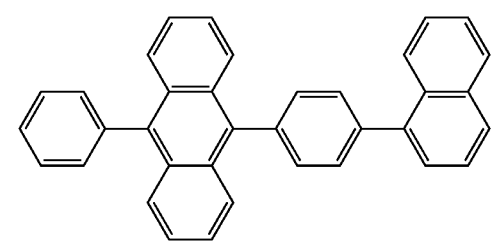
H9
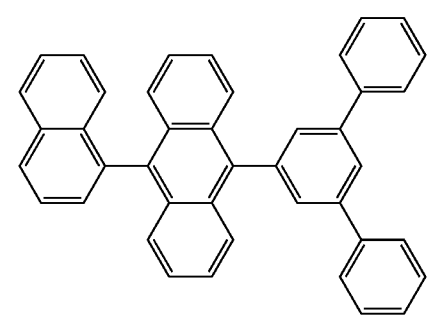
H10
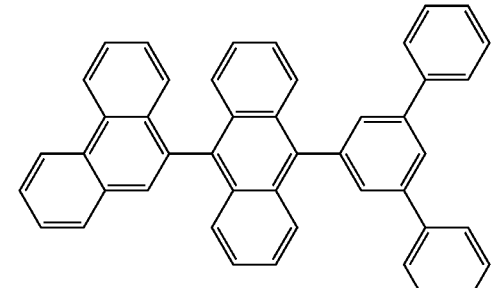
H11
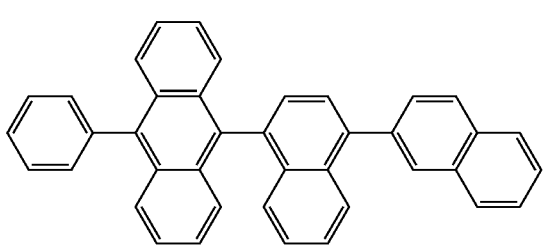
H12
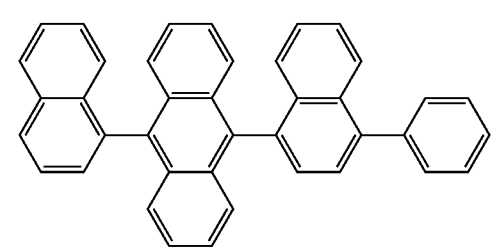
-continued
H13
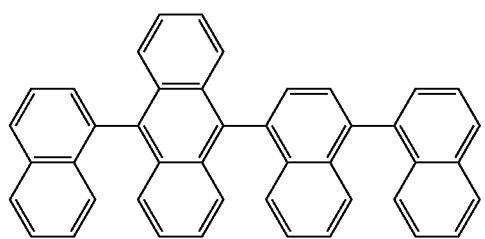
H14
H15
H16
H17
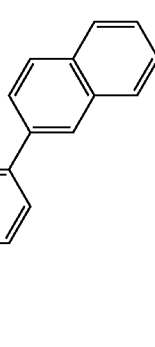

H18
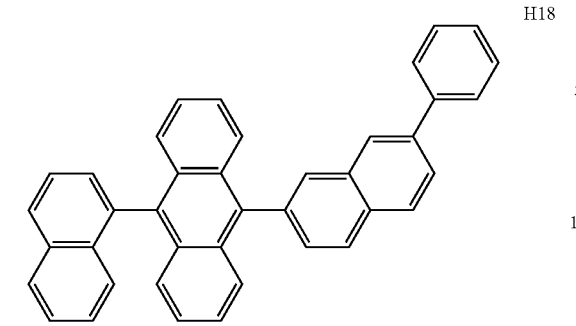
H19
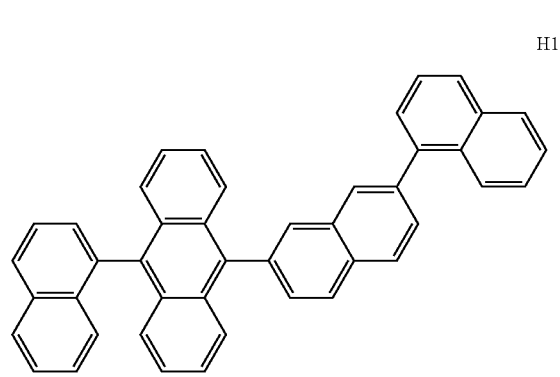
H20
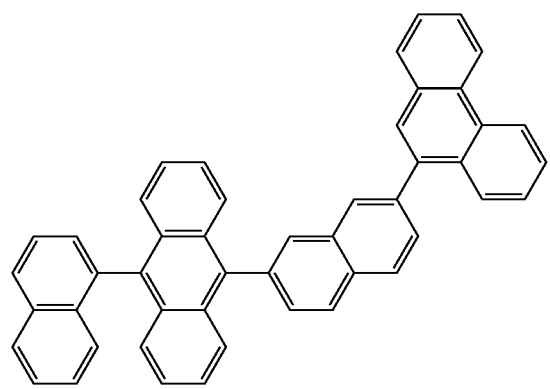
H21
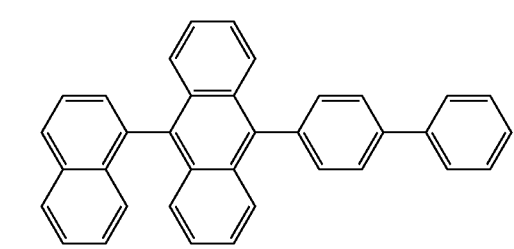
H22
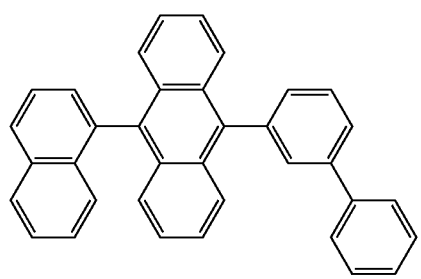
H23
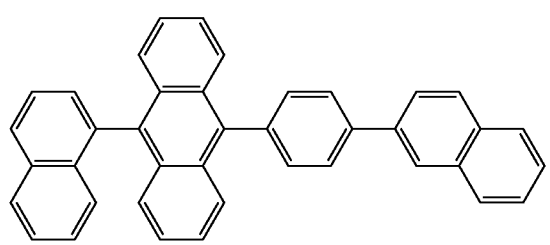
H24
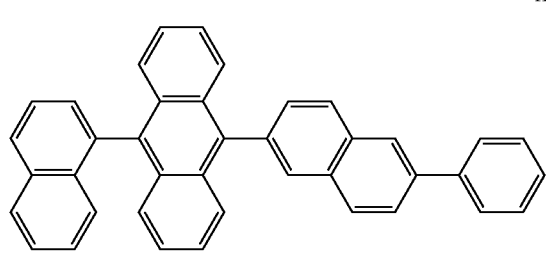
H25
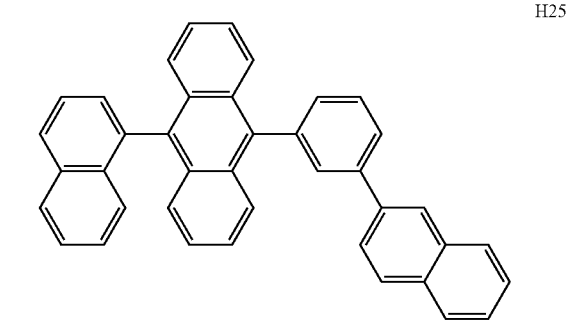
H26
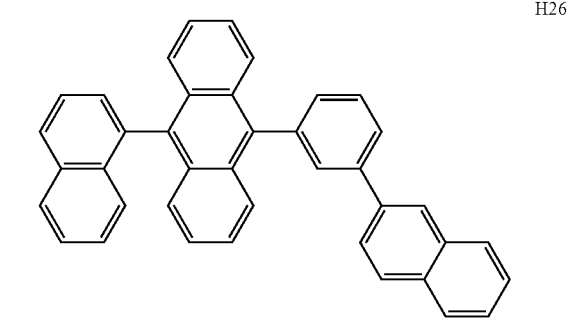
H27
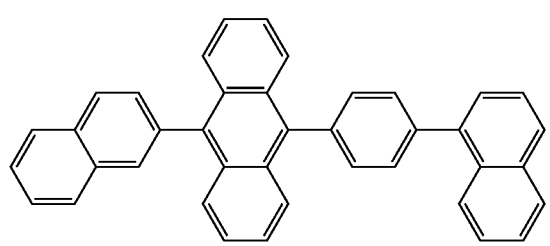

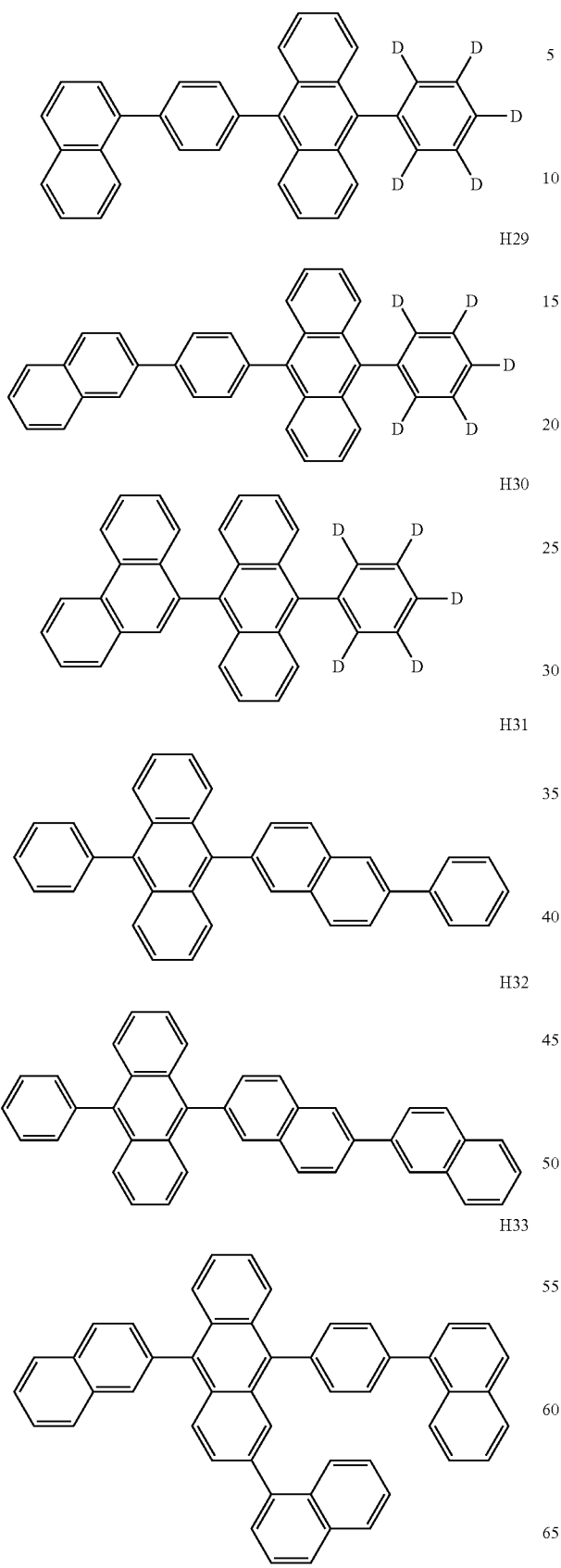
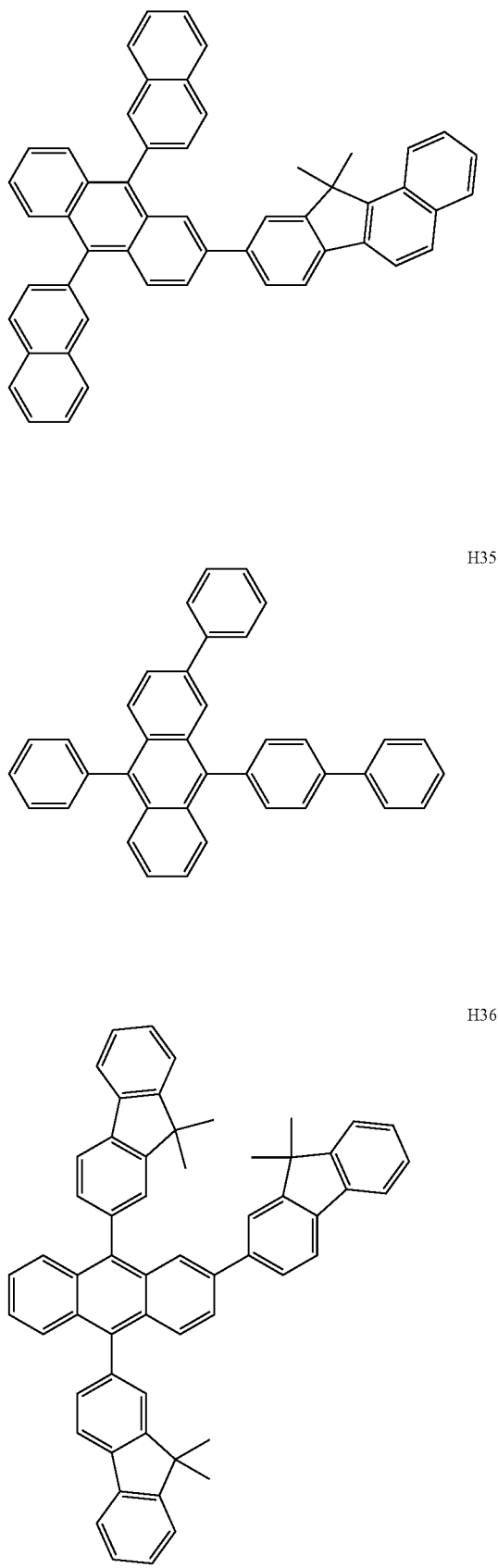

H37
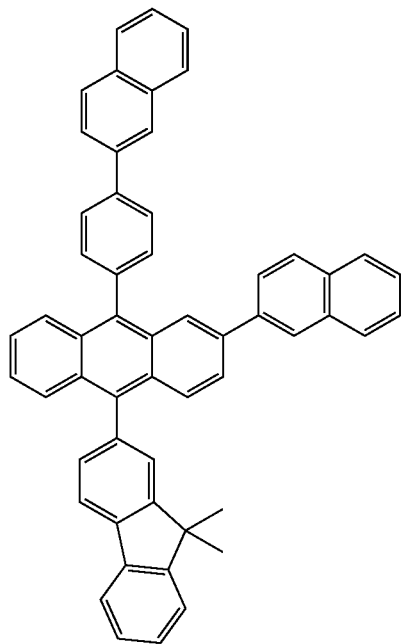
H38
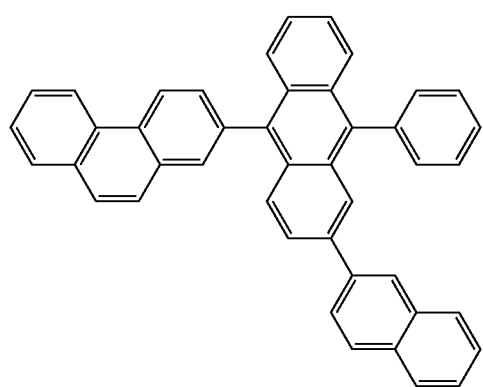
H39
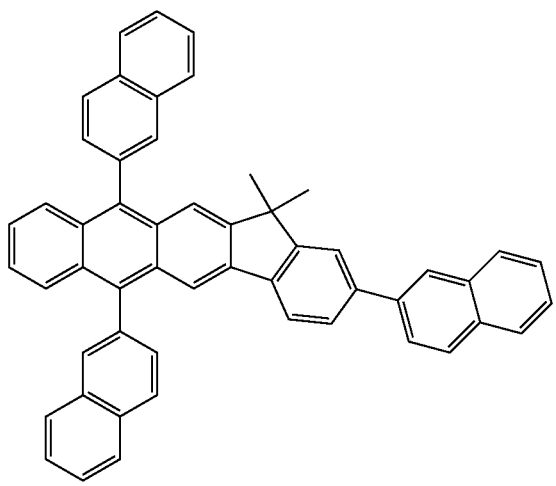
H40
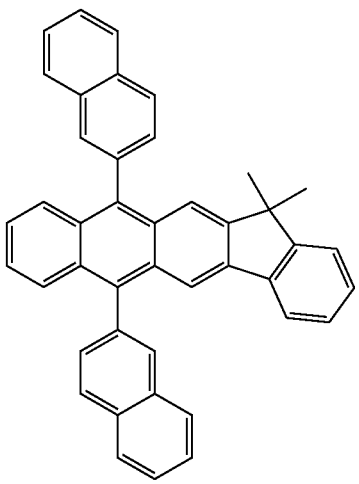
H41
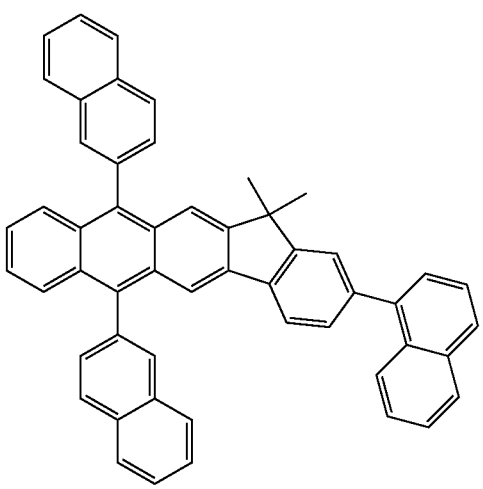
H42
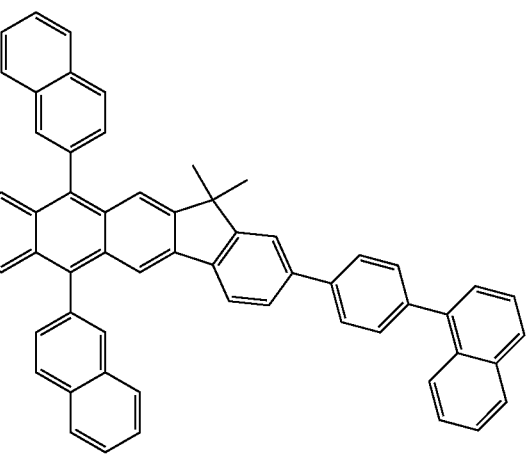

When the organic light-emitting device is a full color organic light-emitting device, the emission layer may be patterned into a red emission layer, a green emission layer, and a blue emission layer. In some embodiments, due to a stack structure including a red emission layer, a green emission layer, and/or a blue emission layer, the emission layer may emit white light.

When the emission layer includes a host and a dopant, an amount of the dopant may be in a range of about 0.01 to about 15 parts by weight based on 100 parts by weight of the host, but is not limited thereto.

A thickness of the emission layer may be in a range of about 100 Å to about 1,000 Å, for example, about 200 Å to about 600 Å. While not wishing to be bound by theory, it is understood that when the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layer structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP, Bphen, and BAlq but is not limited thereto.

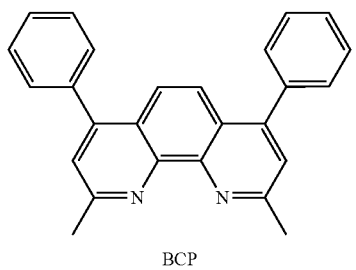

BCP

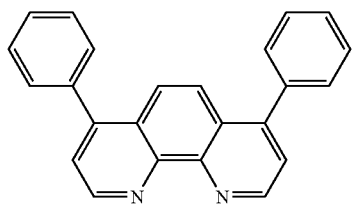

Bphen

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, the hole blocking layer may have improved hole blocking ability without a substantial increase in driving voltage.

The electron transport layer may further include at least one selected from BCP, Bphen, Alq$_3$, BAlq, TAZ, and NTAZ.

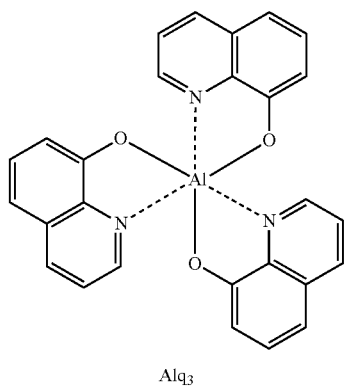

Alq$_3$

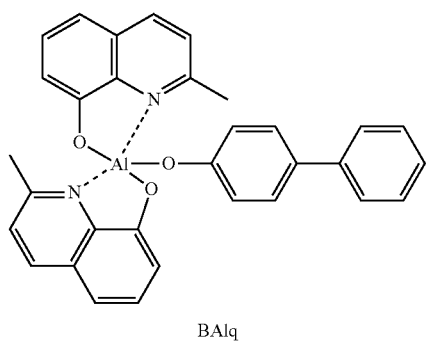

BAlq

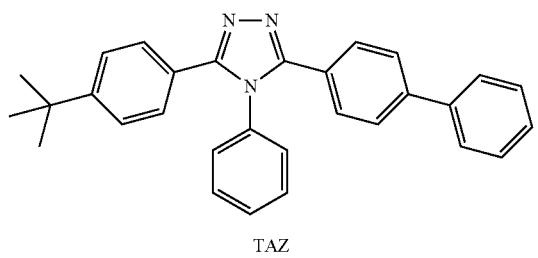

TAZ

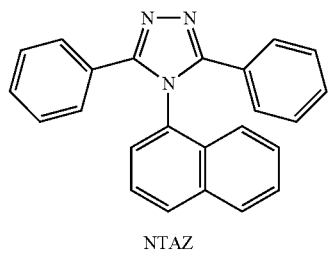

NTAZ

In some embodiments, the electron transport layer may include at least one of ET1 and ET2, but are not limited thereto:

ET1

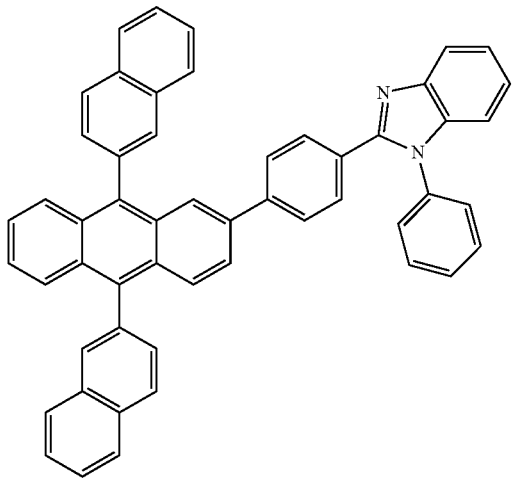

ET2

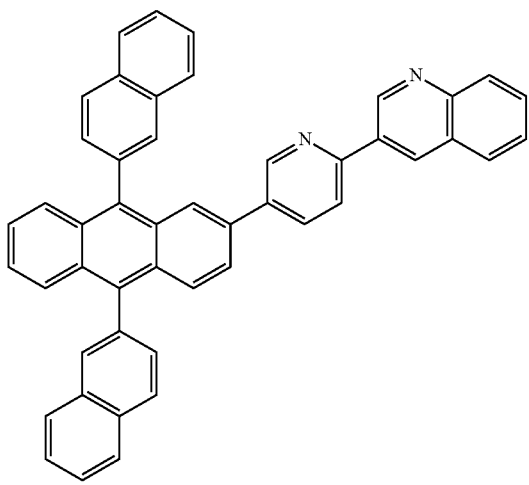

A thickness of the electron transport layer may be in a range of about 100 Å to about 1,000 Å, for example, about 150 Å to about 500 Å. While not wishing to be bound by theory, it is understood that when the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The Li complex may include, for example, Compound ET-D1 (lithium quinolate, LiQ) or ET-D2. The Li complex may include, for example, Compound ET-D1 (lithium quinolate, LiQ) or ET-D2.

ET-D1

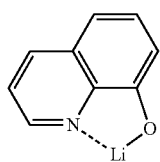

ET-D2

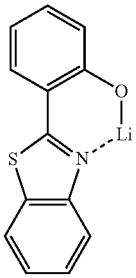

The electron transport region may include an electron injection layer (EIL) that promotes flow of electrons from the second electrode 19 thereinto.

The electron injection layer may include at least one selected from, LiF, NaCl, CsF, $Li_2O$, BaO, and LiQ.

A thickness of the electron injection layer may be in a range of about 1 Å to about 100 Å, for example, about 3 Å to about 90 Å. While not wishing to be bound by theory, it is understood that when the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be selected from metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be used as a material for forming the second electrode 19. In some embodiments, to manufacture a top emission type light-emitting device, a transmissive electrode formed using ITO or IZO may be used as the second electrode 19.

Hereinbefore, the organic light-emitting device has been described with reference to FIG. 1, but is not limited thereto.

A $C_1$-$C_{60}$ alkyl group as used herein refers to a linear or branched aliphatic saturated hydrocarbon monovalent group having 1 to 60 carbon atoms. Examples thereof are a methyl group, an ethyl group, a propyl group, an iso-butyl group, a sec-butyl group, a tert-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by —$OA_{101}$ (wherein $A_{101}$ is the $C_1$-$C_{60}$ alkyl group). Examples thereof are a methoxy group, an ethoxy group, and an iso-propyloxy (iso-propoxy) group.

A $C_2$-$C_{60}$ alkenyl group as used herein refers to a hydrocarbon group formed by including at least one carbon-carbon double bond in the middle or at the terminal of the $C_2$-$C60$ alkyl group. Examples thereof are an ethenyl group, a propenyl group, and a butenyl group. A $C_2$-$C_{60}$ alkenylene group as used herein refers to a divalent group having the same structure as the $C_2$-$C_{60}$ alkenyl group.

A $C_2$-$C_{60}$ alkynyl group as used herein refers to a hydrocarbon group formed by including at least one carbon-carbon triple bond in the middle or at the terminal of the $C_2$-$C60$ alkyl group. Examples thereof are an ethynyl group, and a propynyl group. A $C_2$-$C_{60}$ alkynylene group as used herein refers to a divalent group having the same structure as the $C_2$-$C_{60}$ alkynyl group.

A $C_3$-$C_{10}$ cycloalkyl group as used herein refers to a monovalent saturated hydrocarbon monocyclic group having 3 to 10 carbon atoms. Examples thereof are a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as the $C_3$-$C_{10}$ cycloalkyl group.

A $C_1$-$C_{10}$ heterocycloalkyl group as used herein refers to a monovalent monocyclic group having at least one heteroatom selected from N, O, P, and S as a ring-forming atom and 1 to 10 carbon atoms. Examples thereof are a tetrahydrofuranyl group, and a tetrahydrothiophenyl group. A $C_1$-$C_{10}$ heterocycloalkylene group as used herein refers to a divalent group having the same structure as the $C_1$-$C_{10}$ heterocycloalkyl group.

A $C_3$-$C_{10}$ cycloalkenyl group as used herein refers to a monovalent monocyclic group that has 3 to 10 carbon atoms and at least one carbon-carbon double bond in the ring thereof, and which is not aromatic. Examples thereof are a cyclopentenyl group, a cyclohexenyl group, and a cycloheptenyl group. A $C_3$-$C_{10}$ cycloalkenylene group as used herein refers to a divalent group having the same structure as the $C_3$-$C_{10}$ cycloalkenyl group.

A $C_1$-$C_{10}$ heterocycloalkenyl group as used herein refers to a monovalent monocyclic group that has at least one heteroatom selected from N, O, P, and S as a ring-forming atom, 1 to 10 carbon atoms, and at least one double bond in its ring. Examples of the $C_1$-$C_{10}$ heterocycloalkenyl group are a 2,3-dihydrofuranyl group and a 2,3-dihydrothiophenyl group. A $C_1$-$C_{10}$ heterocycloalkenylene group as used herein refers to a divalent group having the same structure as the $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group as used herein refers to a monovalent group having a heterocyclic aromatic system that has at least one heteroatom selected from N, O, P, Si, and S as a ring-forming atom, and 1 to 60 carbon atoms. A $C_1$-$C_{60}$ heteroarylene group as used herein refers to a divalent group having a carbocyclic aromatic system that has at least one heteroatom selected from N, O, P, Si, and S as a ring-forming atom, and 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

A $C_6$-$C_{60}$ aryloxy group as used herein indicates —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group).

A monovalent non-aromatic condensed polycyclic group as used herein refers to a monovalent group (for example, having 8 to 60 carbon atoms) that has two or more rings condensed to each other, only carbon atoms as a ring forming atom, and which is non-aromatic in the entire molecular structure. A detailed example of the monovalent non-aromatic condensed polycyclic group is a fluorenyl group. A divalent non-aromatic condensed polycyclic group as used herein refers to a divalent group having the same structure as the monovalent non-aromatic condensed polycyclic group.

A monovalent non-aromatic condensed heteropolycyclic group as used herein refers to a monovalent group (for example, having 2 to 60 carbon atoms) that has two or more rings condensed to each other, has a heteroatom selected from N, O, P, Si, and S, other than carbon atoms, as a ring forming atom, and which is non-aromatic in the entire molecular structure. An example of the monovalent non-aromatic condensed heteropolycyclic group is a carbazolyl group. A divalent non-aromatic condensed heteropolycyclic group as used herein refers to a divalent group having the same structure as the monovalent non-aromatic condensed heteropolycyclic group.

At least one of substituents of the substituted $C_5$-$C_{30}$ carbocyclic group, substituted $C_2$-$C_{30}$ heterocyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group as used herein may be selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$B(Q_{16})(Q_{17})$, and —$P(=O)(Q_{18})(Q_{19})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —P(=O)($Q_{28}$)($Q_{29}$); and —N($Q_{31}$)($Q_{32}$), —Si($Q_{33}$)($Q_{34}$)($Q_{35}$), —B($Q_{36}$)($Q_{37}$), and —P(=O)($Q_{38}$)($Q_{39}$), wherein $Q_{11}$ to $Q_{19}$, $Q_{21}$ to $Q_{29}$, and $Q_{31}$ to $Q_{39}$ are each independently selected from a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ alkyl group, and a $C_6$-$C_{60}$ aryl group.

When a group containing a specified number of carbon atoms is substituted with any of the groups listed in the preceding paragraphs, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{60}$ alkyl" refers to a $C_1$-$C_{60}$ alkyl group substituted with $C_6$-$C_{60}$ aryl group, the total number of carbon atoms in the resulting aryl substituted alkyl group is $C_7$-$C_{120}$.

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that an amount of A in molar equivalents was identical to an amount of B in molar equivalents.

EXAMPLE

Synthesis Example 1

Synthesis of Compound 9

Synthesis of Compound M1A

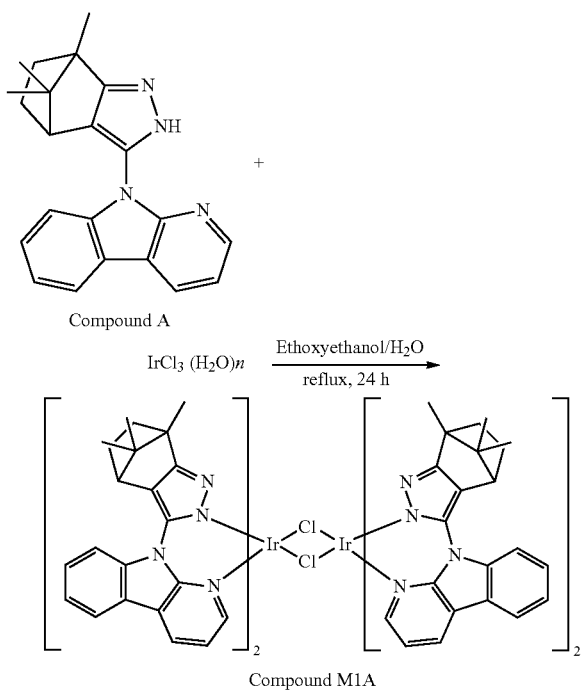

5.08 grams (g) (14.83 millimoles, mmol) of Compound A and 2.32 g (6.59 mmol) of iridium chloride were mixed with 60 milliliters (mL) of ethoxyethanol and 20 mL of distilled water. The resulting mixture was stirred under reflux for about 24 hours until the reaction was complete, and then the temperature was reduced to room temperature. A solid formed therefrom was separated by filtration. The solid was thoroughly washed with water, methanol, and hexane in the stated order, and dried in a vacuum oven, to obtain 3.8 g (63%) of Compound M1A.

Synthesis of Compound 9

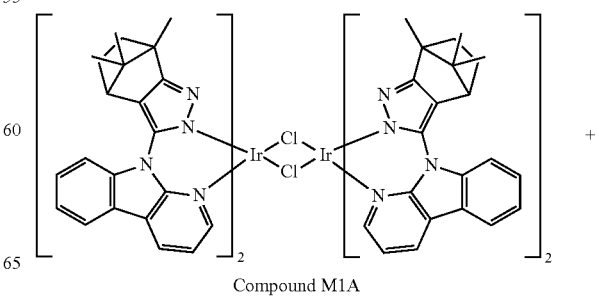

Compound M1A

-continued

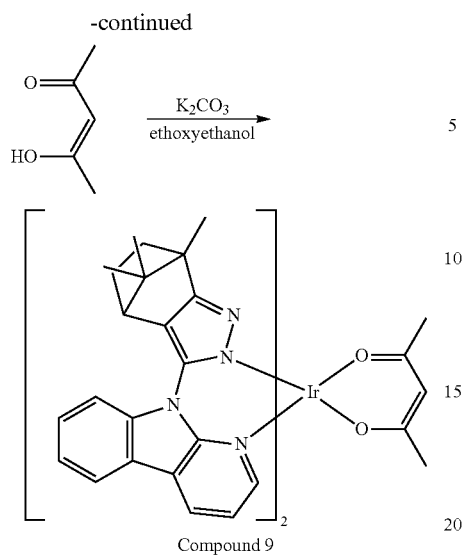

Compound 9

2.80 g (1.54 mmol) of Compound M1A, 1.54 g (15.40 mmol) of acetylacetone, and 2.13 g (15.40 mmol) of $K_2CO_3$ were mixed with 30 mL of ethoxyethanol. The resulting mixture was stirred under reflux for about 12 hours until the reaction was complete, and then the temperature was reduced. The cooled reaction mixture was filtered to obtain a solid, which was then thoroughly washed with ethanol and hexane. The solid was purified by column chromatography using methylene chloride (MC) and hexane to obtain 0.35 g (12%) of Compound 9. The obtained compound was identified by using mass spectroscopy and high-performance liquid chromatography (HPLC) analysis.

HRMS (MALDI) calcd for $C_{49}H_{49}IrN_8O_2$: m/z 974.3608, Found: 974.3601

Synthesis Example 2

Synthesis of Compound 19

Synthesis of Compound M1B

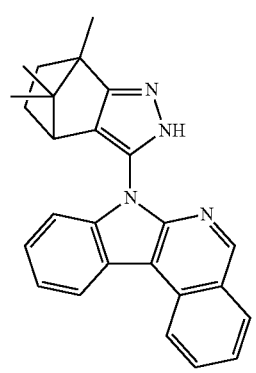

Compound B

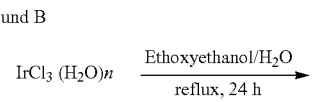

-continued

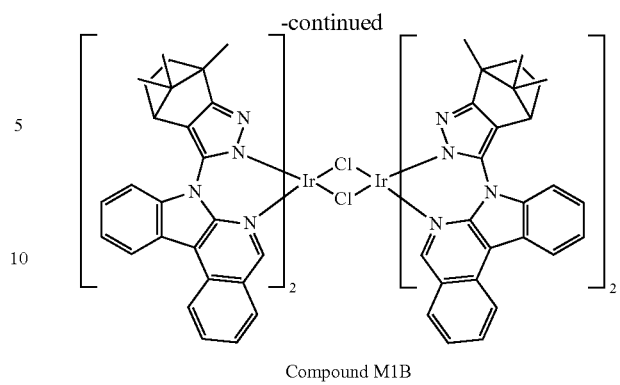

Compound M1B 5.24 g (13.36 mmol) of Compound B and 2.09 g (5.94 mmol) of iridium chloride were mixed with 60 mL of ethoxyethanol and 20 mL of distilled water. The resulting mixture was stirred under reflux for about 24 hours until the reaction was complete, and then the temperature was reduced to room temperature. A solid formed therefrom was separated by filtration. The solid was thoroughly washed with water, methanol, and hexane in the stated order, and dried in a vacuum oven, to obtain 4.5 g (75%) of Compound M1 B.

Synthesis of Compound 19

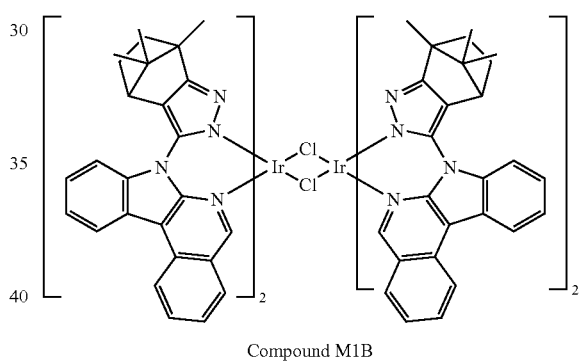

Compound M1B

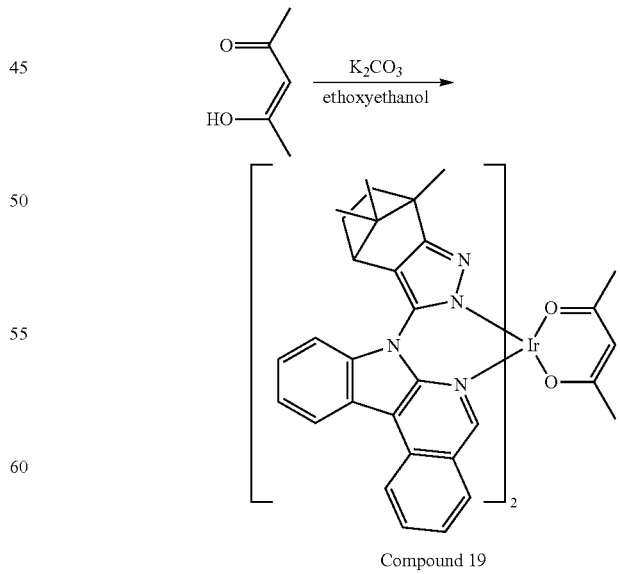

Compound 19

2.82 g (1.40 mmol) of Compound M1B, 1.40 g (13.96 mmol) of acetylacetone, and 1.93 g (13.96 mmol) of $K_2CO_3$ were mixed with 30 mL of ethoxyethanol. The resulting mixture was stirred under reflux for about 12 hours until the reaction was complete, and then the temperature was reduced. The cooled mixture was then filtered to obtain a solid, which was thoroughly washed with ethanol and hexane. The solid was purified by column chromatography using MC and hexane to obtain 0.72 g (24%) of Compound 19. The obtained compound was identified by using mass spectroscopy and HPLC analysis.

HRMS (MALDI) calcd for $C_{57}H_{53}IrN_8O_2$: m/z 1074.3921, Found: 1074.3926

Comparative Synthesis Example

Synthesis of Comparative Compound 1

Synthesis of Compound M1C

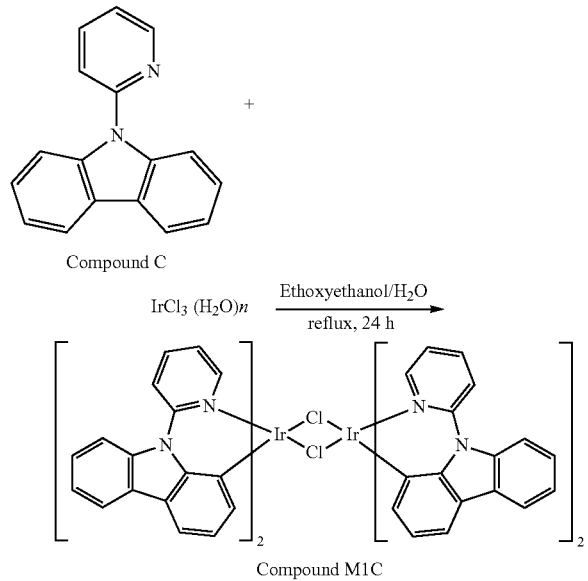

Compound M1C 7.70 g (31.50 mmol) of Compound C and 4.94 g (14.00 mmol) of iridium chloride were mixed with 90 mL of ethoxyethanol and 30 mL of distilled water. The resulting mixture was stirred under reflux for about 24 hours until the reaction was complete, and then the temperature was reduced to room temperature. A solid formed therefrom was separated by filtration. The washed solid was thoroughly washed with water, methanol, and hexane in the stated order, and dried in a vacuum oven, to obtain 8.6 g (86%) of Compound M1C.

Synthesis of Comparative Compound 1

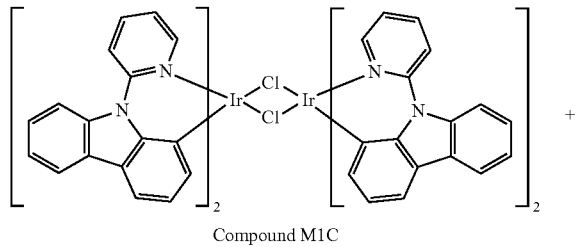

Compound M1C

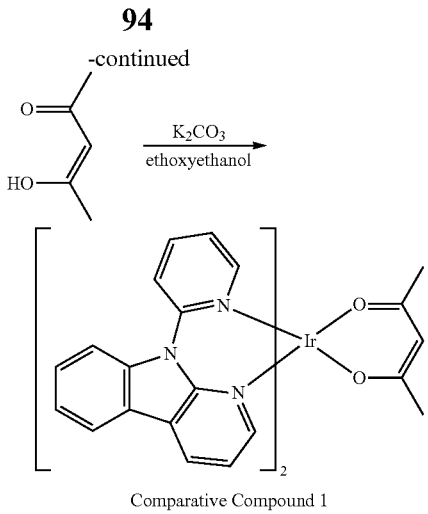

Comparative Compound 1

4.13 g (2.89 mmol) of Compound M1C, 2.90 g (28.92 mmol) of acetylacetone, and 4.00 g (28.92 mmol) of $K_2CO_3$ were mixed with 50 mL of ethoxyethanol. The resulting mixture was stirred under reflux for about 12 hours until the reaction was complete. The formed solid was filtered and thoroughly washed with ethanol and hexane. Then, the solid was purified by column chromatography using MC and hexane to obtain 0.95 g (21%) of Comparative Compound 1. The obtained compound was identified by using mass spectroscopy and HPLC analysis.

HRMS (MALDI) calcd for $C_{39}H_{29}IrN_4O_2$: m/z 778.1920, Found: 778.1914

Example 1

An ITO glass substrate was cut to a size of 50 millimeters (mm)×50 mm×0.5 mm. Then the glass substrate was sonicated in acetone, iso-propyl alcohol, and pure water for about 15 minutes in each solvent, and cleaned by exposure to ultraviolet rays with ozone for 30 minutes.

Thereafter, m-MTDATA was deposited on an ITO electrode (anode) of the glass substrate at a deposition rate of about 1 Angstroms per second (Å/sec) to form a hole injection layer having a thickness of about 600 Angstroms (Å) and α-NPD was deposited on the hole injection layer at a deposition rate of about 1 Å/sec to form a hole transport layer having a thickness of about 250 Å.

Compound 9 (as a dopant) and CBP (as a host) were co-deposited on the hole transport layer at a deposition rate of about 0.1 Å/sec and 1 Å/sec, respectively to form an emission layer having a thickness of about 400 Å.

BAlq was deposited on the emission layer at a deposition rate of 1 Å/sec to form a hole blocking layer having a thickness of about 50 Å. Then, $Alq_3$ was deposited on the hole blocking layer to form an electron transport layer having a thickness of about 300 Å, and LiF was deposited on the electron transport layer to form an electron injection layer having a thickness of about 10 Å. A second electrode (cathode) was formed on the electron injection layer by depositing Al to have a thickness of about 1,200 Å. Accordingly, the manufacture of an organic light-emitting device was completed, in which the organic light-emitting device included a structure of ITO/m-MTDATA (600 Å)/α-NPD (250 Å)/CBP+10% (Compound 9) (400 Å)/BAlq (50 Å)/$Alq_3$ (300 Å)/LiF (10 Å)/Al (1,200 Å).

Example 2 and Comparative Example 1

An organic light-emitting device was manufactured in the same manner as in Example 1, except that the compounds listed in Table 2 were used instead of Compound 9 as a dopant in the formation of the emission layer.

Evaluation Example 1

Evaluation of Characteristics of Organic Light-Emitting Device

Driving voltage, efficiency, power, EL emission wavelength, and color-coordination of the organic light-emitting devices manufactured in Examples 1 and 2 and Comparative Example 1 were evaluated at a selected luminance of about 1,000 candelas per square meter ($cd/m^2$). The results thereof are shown in Table 2. A Keithley 2400 current voltmeter and a luminance meter (Minolta Cs-1000A) were used in evaluation.

Referring to Table 2, it was found that the organic light-emitting devices manufactured in Examples 1 and 2 had excellent driving voltage, efficiency, power, EL emission wavelength, and color-coordination, as compared with the organic light-emitting device of Comparative Example 1.

The organometallic compound according to embodiments has excellent electric characteristics and thermal stability. Accordingly, an organic light-emitting device including the organometallic compound may have excellent driving voltage, current density, efficiency, power, color purity, and lifespan characteristics.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood

TABLE 2

| | Dopant | Driving voltage (V) | Efficiency (cd/A) | Power (lm/W) | $\lambda_{max}$ | CIEx | CIEy |
|---|---|---|---|---|---|---|---|
| Example 1 | Compound 9 | 7.0 | 10 | 4.5 | 525 | 0.28 | 0.69 |
| Example 2 | Compound 19 | 7.3 | 7.5 | 3.2 | 601.8 | 0.61 | 0.38 |
| Comparative Example 1 | Comparative Compound 1 | 8.0 | 6.0 | 2.4 | 535 | 0.40 | 0.58 |

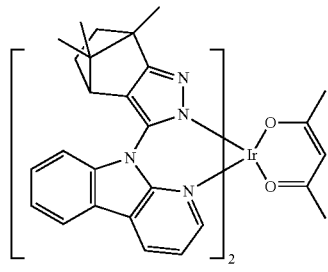

Compound 9

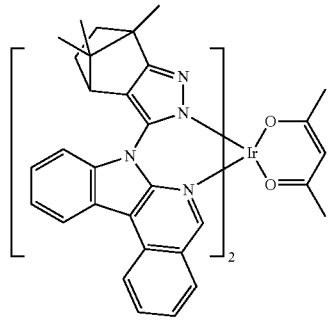

Compound 19

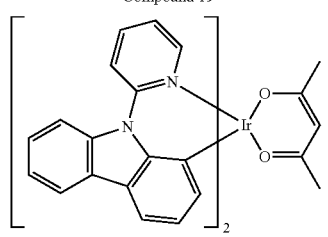

Comparative Compound 1

What is claimed is:
1. An organometallic compound represented by Formula 1:

$$M(L_1)_{n1}(L_2)_{n2}$$ Formula 1

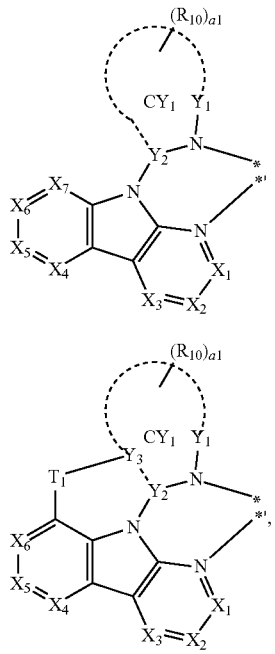

Formula 2A

Formula 2B wherein
M in Formula 1 is selected from iridium (Ir), platinum (Pt), osmium (Os), titanium (Ti), zirconium (Zr), hafnium (Hf), europium (Eu), terbium (Tb), thulium (Tm), and rhodium (Rh),
$L_1$ in Formula 1 is selected from a ligand represented by Formula 2A or 2B,
$L_2$ in Formula 1 is selected from a mono-anionic organic ligand,
* and *' in Formulae 2A and 2B each indicate a binding site to M in Formula 1,
n1 in Formula 1 is 1, 2, or 3, and when n1 is 2 or more, 2 or more groups $L_1$ are identical to or different from each other,
n2 in Formula 1 is 0, 1, 2, or 3, and when n2 is 2 or more, 2 or more groups $L_2$ are identical to or different from each other,
$Y_1$ and $Y_3$ in Formulae 2A and 2B are each independently carbon or nitrogen,
$Y_2$ in Formulae 2A and 2B is carbon,
a bond between $Y_2$ and $Y_3$ in Formula 2B is a double bond,
$CY_1$ in Formulae 2A and 2B is a $C_2$-$C_{30}$ heterocyclic group,
in Formulae 2A and 2B, $X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, $X_7$ is N or $C(R_7)$,
$T_1$ in Formula 2B is selected from a single bond, *—O*', *—S—*', *—N($R_{31}$)—*', *—C($R_{31}$)($R_{32}$)—*', *—C($R_{31}$)=C($R_{32}$)—*', and *—Si($R_{31}$)($R_{32}$)—'*, and $R_{31}$ and $R_{32}$ are optionally bound to each other to form a substituted or unsubstituted $C_5$-$C_{30}$ carbocyclic group or a substituted or unsubstituted $C_2$-$C_{30}$ heterocyclic group,
$R_1$ to $R_7$, $R_{10}$, $R_{31}$, and $R_{32}$ are each independently selected from hydrogen, deuterium, —F, —Cl, —Br, —I, —SF$_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), and —P(=O)($Q_8$)($Q_9$),
a1 is an integer selected from 0 to 5,
two or more among $R_1$ to $R_3$ in Formulae 2A and 2B are optionally bound to each other to form a substituted or unsubstituted $C_5$-$C_{30}$ carbocyclic group or a substituted or unsubstituted $C_2$-$C_{30}$ heterocyclic group,
two or more among $R_4$ to $R_7$ in Formula 2A are optionally bound to each other to form a substituted or unsubstituted $C_5$-$C_{30}$ carbocyclic group or a substituted or unsubstituted $C_2$-$C_{30}$ heterocyclic group,
two or more among $R_4$ to $R_6$ in Formula 2B are optionally bound to each other to form a substituted or unsubstituted $C_5$-$C_{30}$ carbocyclic group or a substituted or unsubstituted $C_2$-$C_{30}$ heterocyclic group,
two or more among groups $R_{10}$ in the number of a1 in Formulae 2A and 2B are optionally bound to each other to form a substituted or unsubstituted $C_5$-$C_{30}$ carbocyclic group or a substituted or unsubstituted $C_2$-$C_{30}$ heterocyclic group, and
at least one of substituents of the substituted $C_5$-$C_{30}$ carbocyclic group, substituted $C_2$-$C_{30}$ heterocyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:
deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), and —P(=O)($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —P(=O)($Q_{28}$)($Q_{29}$); and —N($Q_{31}$)($Q_{32}$), —Si($Q_{33}$)($Q_{34}$)($Q_{35}$), —B($Q_{36}$)($Q_{37}$) and —P(=O)($Q_{38}$)($Q_{39}$), wherein $Q_1$ to $Q_9$, $Q_{11}$ to $Q_{19}$, $Q_{21}$ to $Q_{29}$, and $Q_{31}$ to $Q_{39}$ are each independently selected from a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ alkyl group, and a $C_6$-$C_{60}$ aryl group.

2. The organometallic compound of claim 1, wherein in Formula 1,

M is Ir or Os, and the sum of n1 and n2 is 3 or 4; or

M is Pt, and the sum of n1 and n2 is 2.

3. The organometallic compound of claim 1, wherein $CY_1$ in Formulae 2A and 2B is selected from a pyrrole ring, an isoindole ring, an indole ring, an indazole ring, a pyrazole ring, an imidazole ring, a triazole ring, an oxazole ring, an isoxazole ring, an oxadiazole ring, a thiazole ring, an isothiazole ring, a thiadiazole ring, a purine ring, a benzoimidazole ring, an isobenzothiazole ring, a benzoxazole ring, an isobenzoxazole ring, an imidazopyridine ring, an imidazopyrimidine ring, and a pyrrolopyridine ring.

4. The organometallic compound of claim 1, wherein $T_1$ in Formula 2B is selected from *—O—*', *—S—*', *—C($R_{31}$)($R_{32}$)—*', and groups represented by Formulae 11-1 to 11-4 below:

Formula 11-1

Formula 11-2

Formula 11-3

Formula 11-4 wherein * and *' in Formulae 11-1 to 11-4 each indicate a binding site to a neighboring atom.

5. The organometallic compound of claim 1, wherein $R_1$ to $R_7$, $R_{10}$, $R_{31}$, and $R_{32}$ are each independently selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —$N(Q_1)(Q_2)$, —$Si(Q_3)(Q_4)(Q_5)$, —$B(Q_6)(Q_7)$, and —$P(=O)(Q_8)(Q_9)$, wherein $Q_1$ to $Q_9$ are each independently selected from: —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group.

6. The organometallic compound of claim 1, wherein $R_1$ to $R_7$, $R_{10}$, $R_{31}$, and $R_{32}$ are each independently selected from:

hydrogen, deuterium, —F, a cyano group, a nitro group, —$SF_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group and a dibenzothiophenyl group; and a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group, each substituted with at least one selected from deuterium, —F, —CD$_3$, —CD$_2$H, —CDH$_2$, —CF$_3$, —CF$_2$H, —CFH$_2$, a cyano group, a nitro group, a C$_1$-C$_{10}$ alkyl group, a C$_1$-C$_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group; and
—N(Q$_1$)(Q$_2$), —Si(Q$_3$)(Q$_4$)(Q$_5$), —B(Q$_6$)(Q$_7$), and —P(=O)(Q$_8$)(Q$_9$);
wherein Q$_1$ to Q$_9$ are each independently selected from:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;
an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and
an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a C$_1$-C$_{10}$ alkyl group, and a phenyl group.

7. The organometallic compound of claim 1, wherein R$_1$ to R$_7$, R$_{10}$, R$_{31}$, and R$_{32}$ are each independently selected from hydrogen, deuterium, —F, a cyano group, a nitro group, —SF$_5$, —CH$_3$, —CD$_3$, —CD$_2$H, —CDH$_2$, —CF$_3$, —CF$_2$H, —CFH$_2$, groups represented by Formulae 9-1 to 9-19, groups represented by Formulae 10-1 to 10-36, and —Si(Q$_3$)(Q$_4$)(Q$_5$),
Q3 to Q5 are each independently selected from:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;
an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and
an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a C$_1$-C$_{10}$ alkyl group, and a phenyl group:

-continued
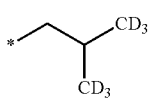
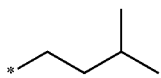
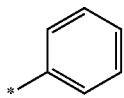
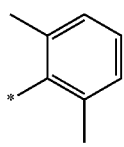
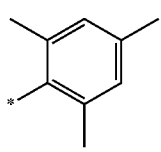
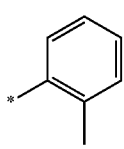
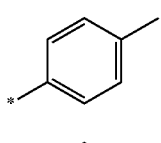
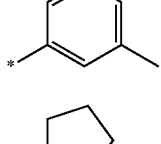
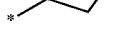
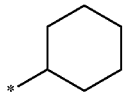
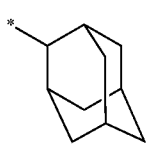
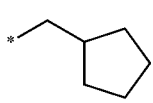
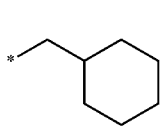
-continued
Formula 9-18
Formula 9-19
Formula 10-1
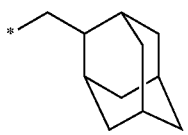
Formula 10-2
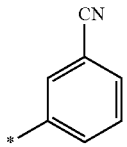
Formula 10-3
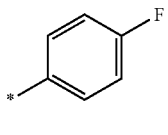
Formula 10-4
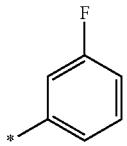
Formula 10-5
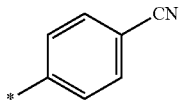
Formula 10-6
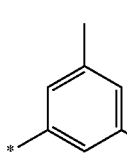
Formula 10-7
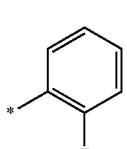
Formula 10-8
Formula 10-9
Formula 10-10
Formula 10-11
Formula 10-12
Formula 10-13
Formula 10-14
Formula 10-15
Formula 10-16
Formula 10-17
Formula 10-18
Formula 10-19
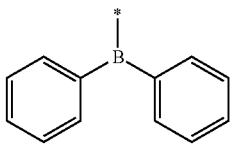
Formula 10-20
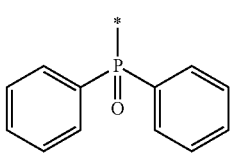
Formula 10-21
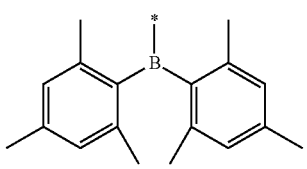

Formula 10-22
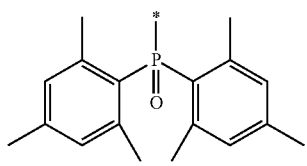
Formula 10-23
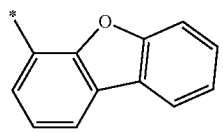
Formula 10-24
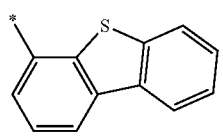
Formula 10-25
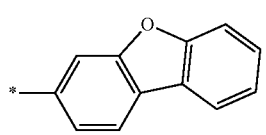
Formula 10-26
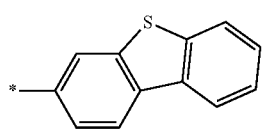
Formula 10-27
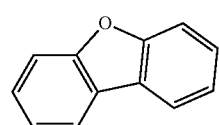
Formula 10-28
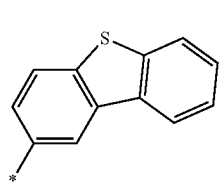
Formula 10-29
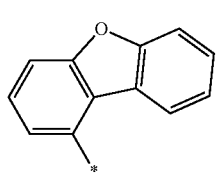
Formula 10-30
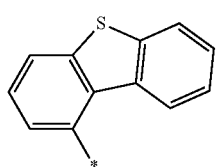
Formula 10-31
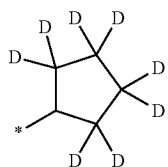
Formula 10-32
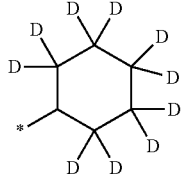
Formula 10-33
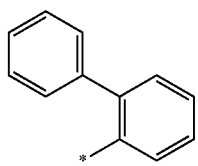
Formula 10-34
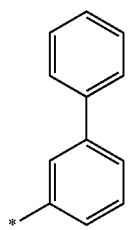
Formula 10-35
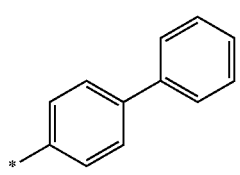
Formula 10-36
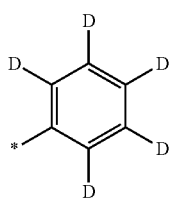
wherein, * in Formulae 9-1 to 9-19 and 10-1 to 10-36 indicates a binding site to a neighboring atom.
8. The organometallic compound of claim 1, wherein ligand $L_1$ in Formula 1 is selected from groups represented by Formulae 2A-1 to 2A-4 and 2B-1 to 2B-3:
Formula 2A-1
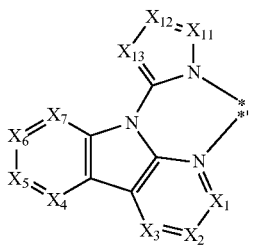

-continued

Formula 2A-2

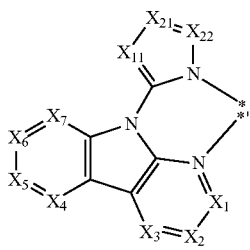

Formula 2A-3

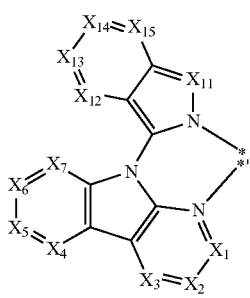

Formula 2A-4

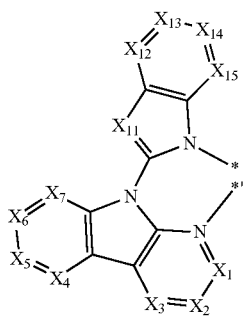

Formula 2B-1

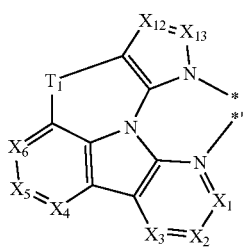

Formula 2B-2

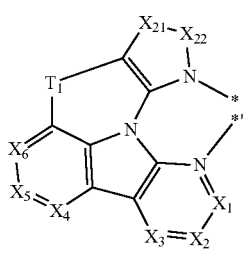

-continued

Formula 2B-3

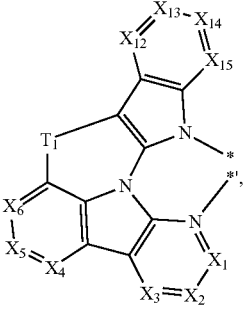

wherein, in Formulae 2A-1 to 2A-4 and 2B-1 to 2B-3,
$X_1$ to $X_7$, and $T_1$ are the same as described in claim 1,
$X_{11}$ is N or $C(R_{11})$, $X_{12}$ is N or $C(R_{12})$, $X_{13}$ is N or $C(R_{13})$, $X_{14}$ is N or $C(R_{14})$, $X_{15}$ is N or $C(R_{15})$,
$X_{21}$ is O, S, $N(R_{21})$, or $C(R_{22})(R_{23})$,
$X_{21}$ is O, S, $N(R_{24})$, or $C(R_{25})(R_{26})$,
$R_{11}$ to $R_{15}$ and $R_{21}$ to $R_{26}$ are the same as described in connection with $R_{10}$ in claim 1, and
* and *' each indicate a binding site to M in Formula 1.

9. The organometallic compound of claim 8, wherein
$X_1$ is $C(R_1)$, $X_2$ is $C(R_2)$, $X_3$ is $C(R_3)$, $X_4$ is $C(R_4)$, $X_5$ is $C(R_5)$, $X_6$ is $C(R_6)$, $X_7$ is $C(R_7)$,
$T_1$ is selected from *—O—*', *—S—*', *—$C(R_{31})(R_{32})$—*', and groups represented by Formulae 11-1 to 11-4,
$R_1$ to $R_7$, $R_{11}$ to $R_{15}$, $R_{21}$ to $R_{26}$, $R_{31}$, and $R_{32}$ are each independently selected from:
hydrogen, deuterium, —F, a cyano group, a nitro group, —$SF_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group;
a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group, each substituted with at least one selected from deuterium, —F, —CD$_3$, —CD$_2$H, —CDH$_2$, —CF$_3$, —CF$_2$H, —CFH$_2$, a cyano group, a nitro group, a C$_1$-C$_{10}$ alkyl group, a C$_1$-C$_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group; and
—N(Q$_1$)(Q$_2$), —Si(Q$_3$)(Q$_4$)(Q$_5$), —B(Q$_6$)(Q$_7$), and —P(=O)(Q$_8$)(Q$_9$), wherein Q$_1$ to Q$_9$ are each independently selected from:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a C$_1$-C$_{10}$ alkyl group, and a phenyl group, two neighboring substituents among R$_1$ to R$_3$ are optionally bound to each other to form a substituted or unsubstituted C$_5$-C$_{10}$ carbocyclic ring, two neighboring substituents among R$_4$ to R$_7$ are optionally bound to each other to form a substituted or unsubstituted C$_5$-C$_{10}$ carbocyclic ring, and two neighboring substituents among R$_{11}$ to R$_{15}$ and R$_{21}$ to R$_{26}$ are optionally bound to each other to form a substituted or unsubstituted C$_5$-C$_{10}$ carbocyclic ring:

Formula 11-1

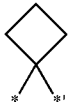

Formula 11-2

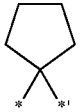

Formula 11-3

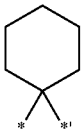

Formula 11-4 wherein * and *' in Formulae 11-1 to 11-4 each indicate a binding site to a neighboring atom.

10. The organometallic compound of claim 8, wherein X$_5$ is C(CN) or X$_{12}$ is C(CN).

11. The organometallic compound of claim 1, wherein ligand L$_1$ in Formula 1 is selected from ligands represented by Formulae 2A-1(1) to 2A-1(6):

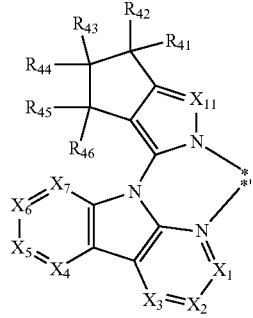

Formula 2A-1(1)

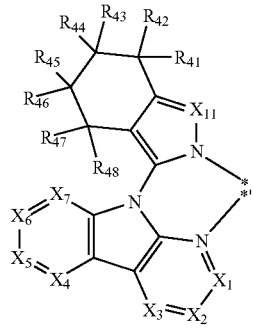

Formula 2A-1(2)

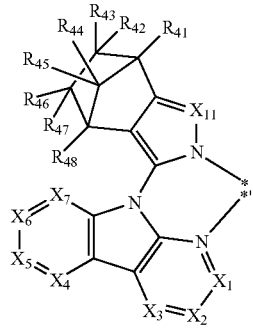

Formula 2A-1(3)

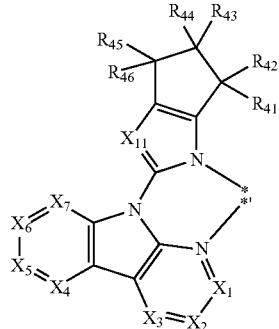

Formula 2A-1(4)

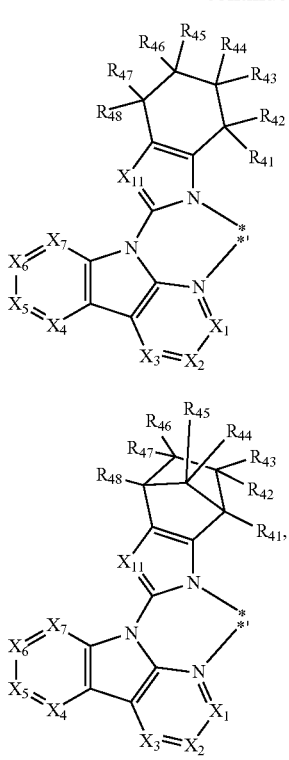

Formula 2A-1(5)

Formula 2A-1(6)

wherein, in Formulae 2A-1(1) to 2A-1(6), $X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, $X_7$ is N or $C(R_7)$, $T_1$ is selected from *—O—*', *—S—*', *—C($R_{31}$)($R_{32}$)—*', and groups represented by Formulae 11-1 to 11-4, $X_{11}$ is N or $C(R_{11})$, $R_1$ to $R_7$, $R_{11}$, $R_{31}$, $R_{32}$, and $R_{41}$ to $R_{48}$ are each independently selected from:

hydrogen, deuterium, —F, a cyano group, a nitro group, —SF$_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group;

a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group, each substituted with at least one selected from deuterium, —F, —CD$_3$, —CD$_2$H, —CDH$_2$, —CF$_3$, —CF$_2$H, —CFH$_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group; and —N($Q_1$)($Q_2$), —Si($Q_3$)($Q_4$)($Q_5$), —B($Q_6$)($Q_7$), and —P(=O)($Q_8$)($Q_9$), wherein $Q_1$ to $Q_9$ are each independently selected from: —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group, two neighboring substituents among $R_1$ to $R_3$ are optionally bound to each other to form a substituted or unsubstituted $C_5$-$C_{10}$ carbocyclic ring, two neighboring substituents among $R_4$ to $R_7$ are optionally bound to each other to form a substituted or unsubstituted $C_5$-$C_{10}$ carbocyclic ring, and

* and *' each indicate a binding site to M in Formula 1:

Formula 11-1

Formula 11-2

Formula 11-3

-continued
Formula 11-4
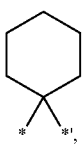
wherein * and *' in Formulae 11-1 to 11-4 each indicate a binding site to a neighboring atom.
12. The organometallic compound of claim 1, wherein ligand $L_1$ in Formula 1 is selected from ligands represented by Formulae 4-1 to 4-7, 4-11 to 4-17, 4-21 to 4-27, 4-31 to 4-37, 4-41 to 4-44, 4-51 to 4-54, 4-61 to 4-64, and 4-71 to 4-74:
Formula 4-1
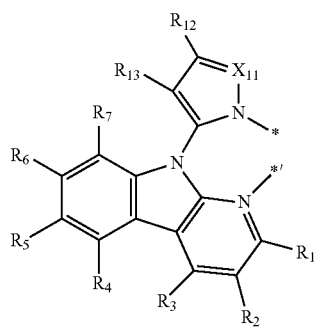
Formula 4-2
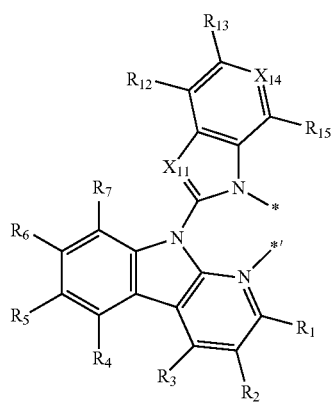
Formula 4-3
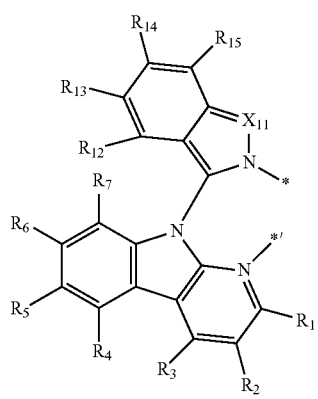
Formula 4-4
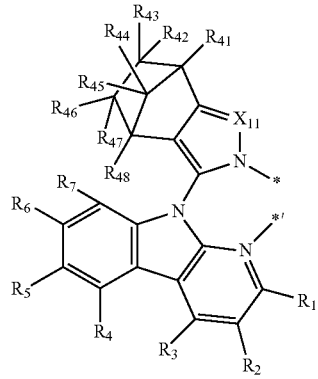
Formula 4-5
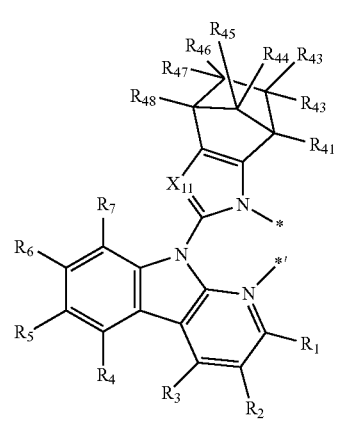
Formula 4-6
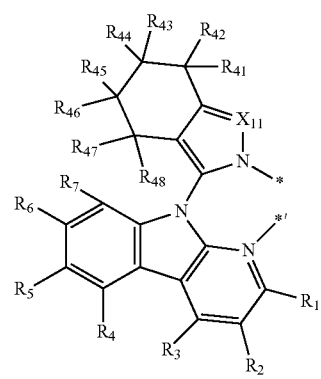
Formula 4-7
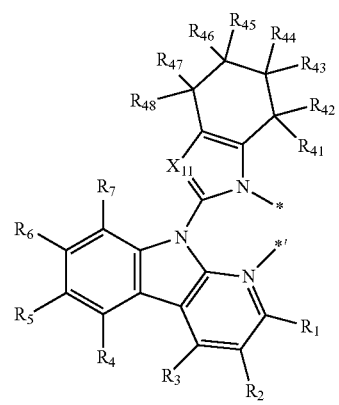

Formula 4-11
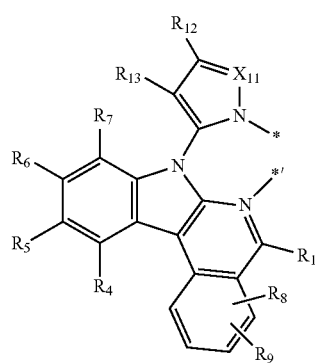
Formula 4-12
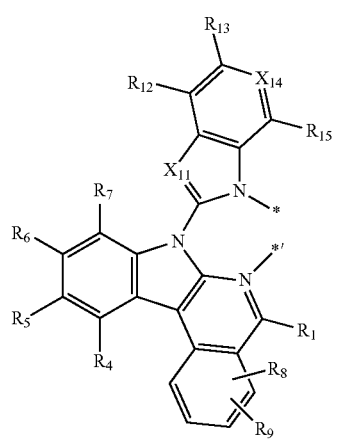
Formula 4-13
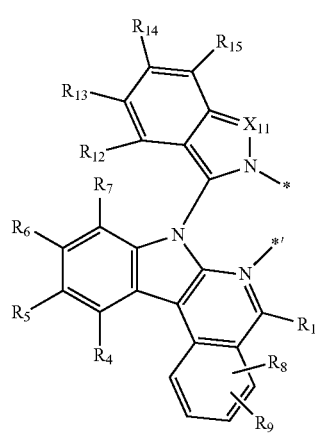
Formula 4-14
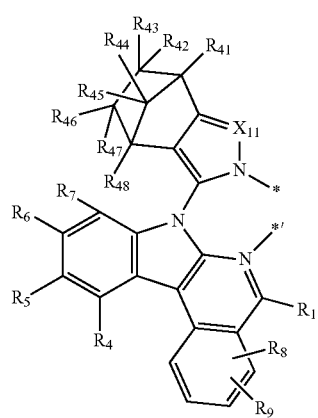
Formula 4-15
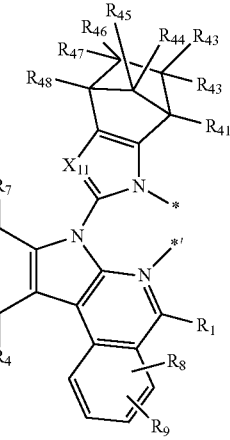
Formula 4-16
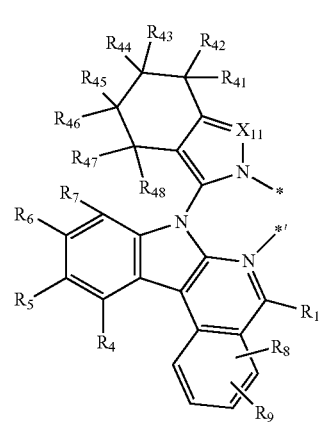
Formula 4-17
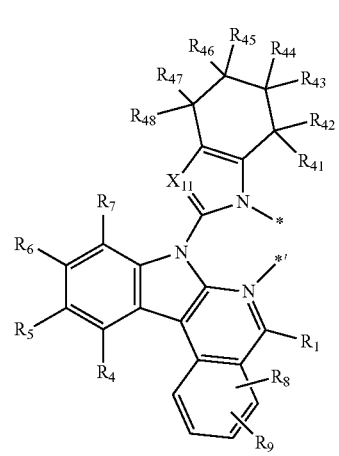
Formula 4-21
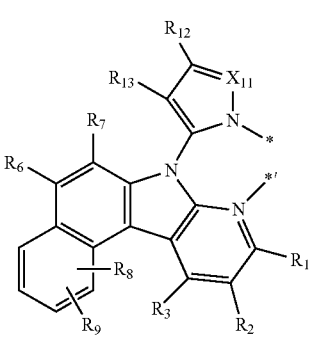

Formula 4-22
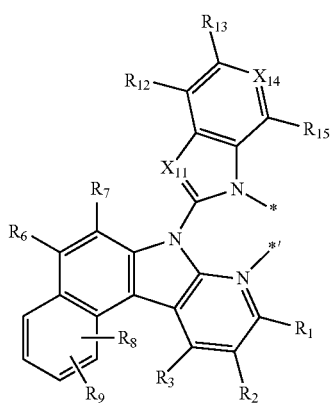
Formula 4-23
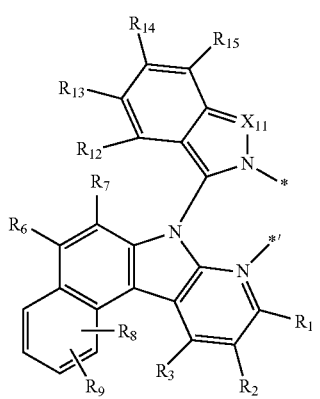
Formula 4-24
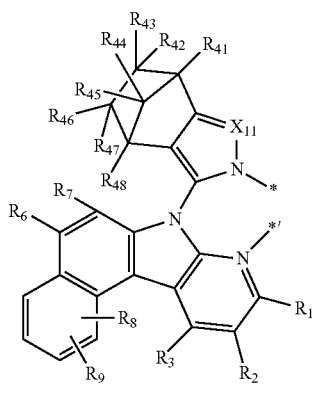
Formula 4-25
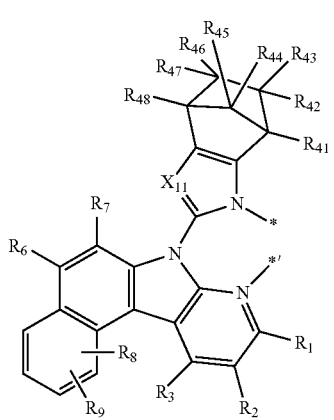
Formula 4-26
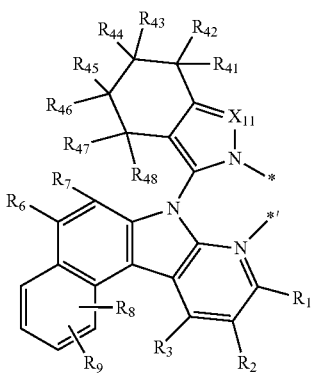
Formula 4-27
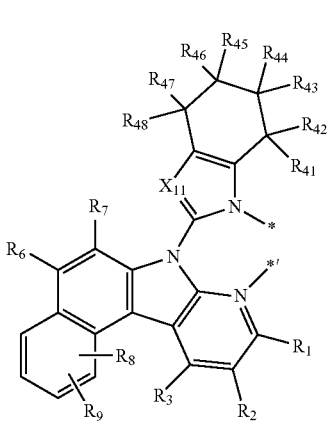
Formula 4-31
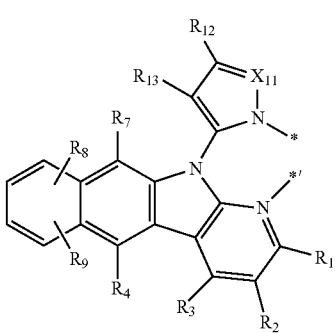
Formula 4-32
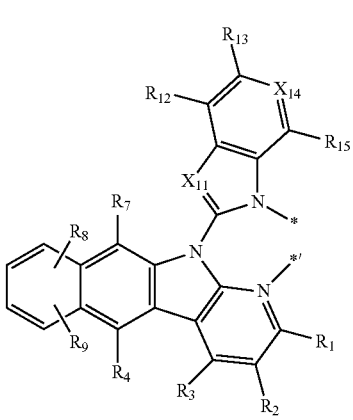

121
-continued
Formula 4-33
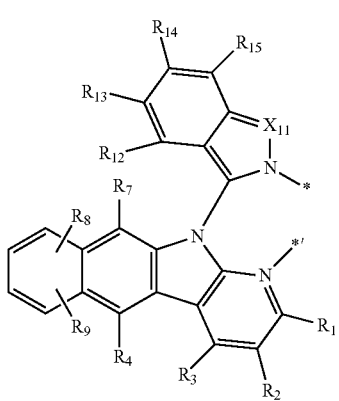
Formula 4-34
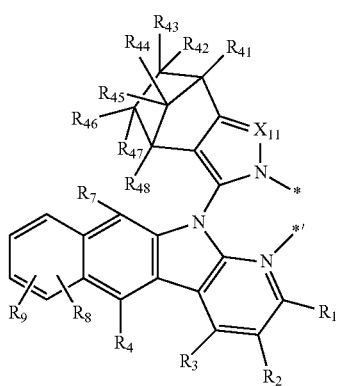
Formula 4-35
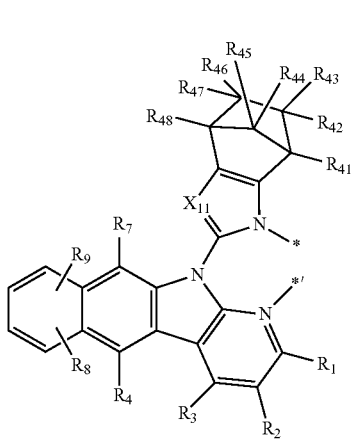
Formula 4-36
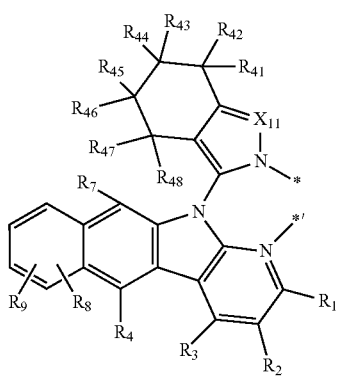
122
-continued
Formula 4-37
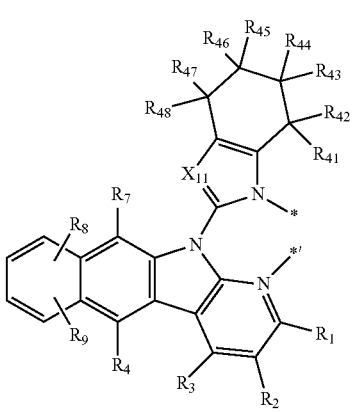
Formula 4-41
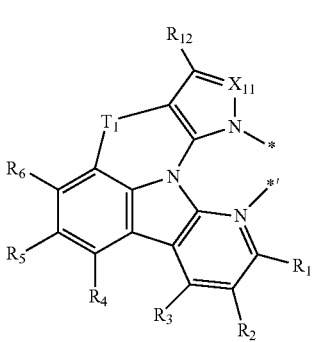
Formula 4-42
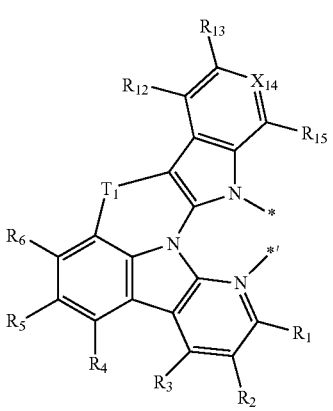
Formula 4-43
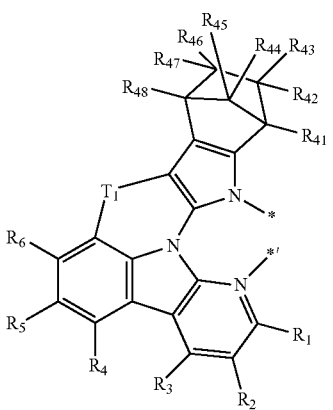

Formula 4-44
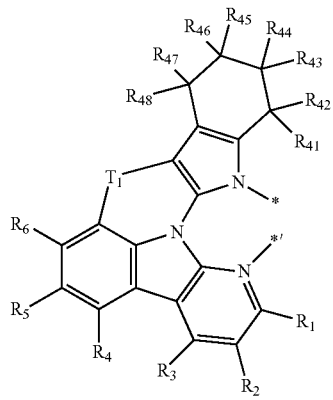
Formula 4-51
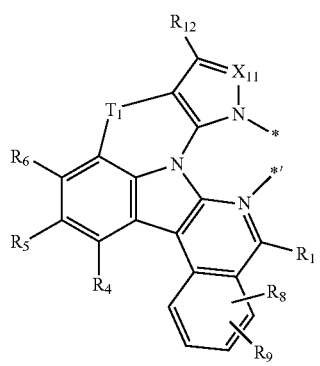
Formula 4-52
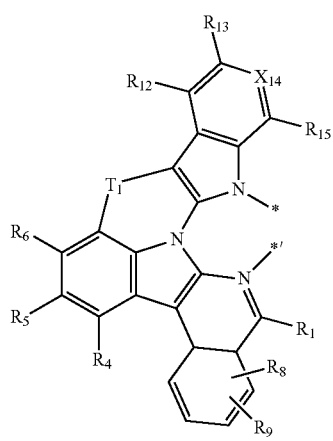
Formula 4-53
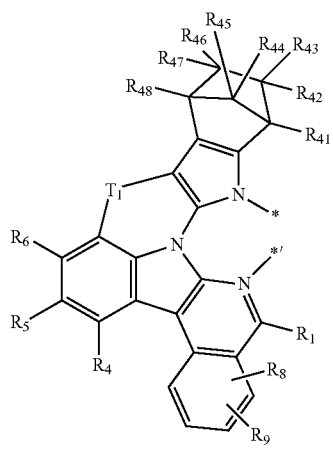
Formula 4-54
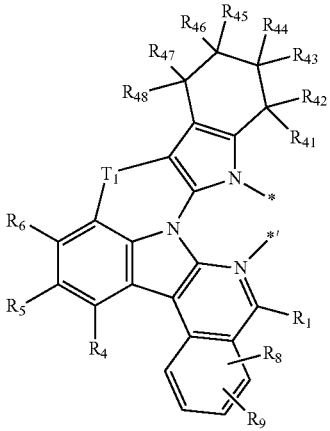
Formula 4-61
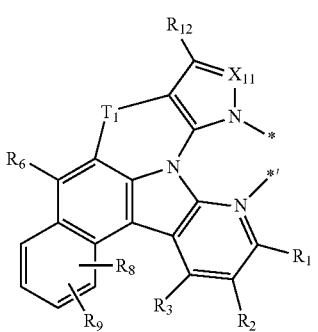
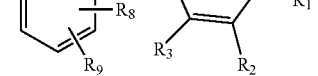
Formula 4-62
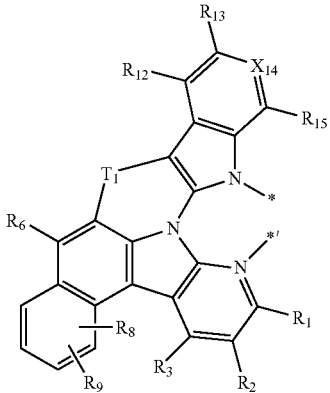
Formula 4-63
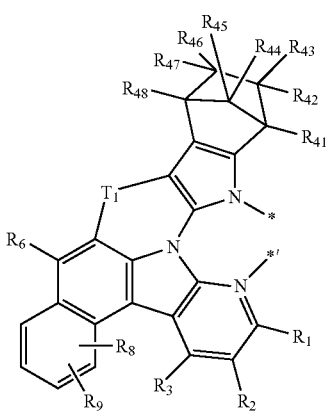

Formula 4-64
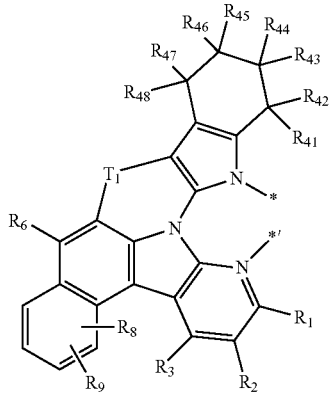

Formula 4-71
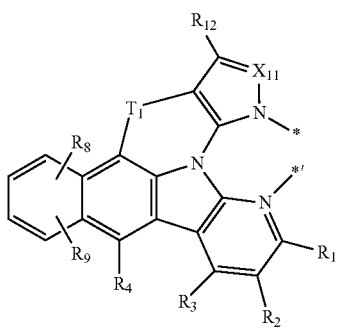

Formula 4-72
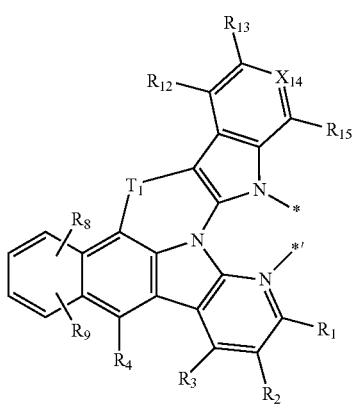

Formula 4-73
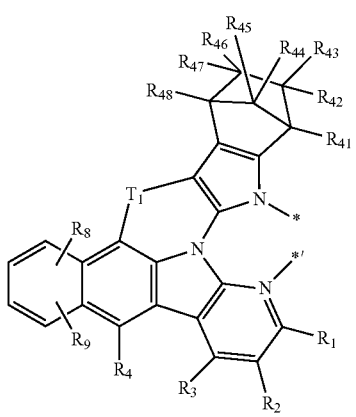

Formula 4-74
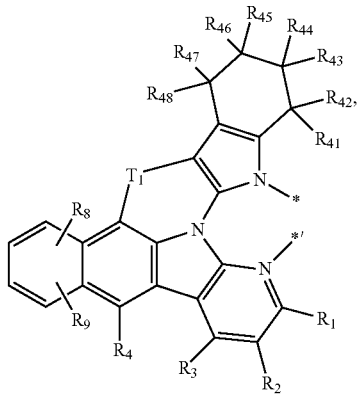

wherein, in Formulae 4-1 to 4-7, 4-11 to 4-17, 4-21 to 4-27, 4-31 to 4-37, 4-41 to 4-44, 4-51 to 4-54, 4-61 to 4-64, and 4-71 to 4-74, $X_{11}$ is N or $C(R_{11})$, $X_{14}$ is N or $C(R_{14})$, $T_1$ is the same as described in claim 1, $R_1$ to $R_9$, $R_{11}$ to $R_{15}$ and $R_{41}$ to $R_{48}$ are each independently selected from hydrogen, deuterium, —F, a cyano group, a nitro group, —SF$_5$, —CH$_3$, —CD$_3$, —CD$_2$H, —CDH$_2$, —CF$_3$, —CF$_2$H, —CFH$_2$, groups represented by Formulae 9-1 to 9-19, groups represented by Formulae 10-1 to 10-36, and —Si(Q$_3$)(Q$_4$)(Q$_5$), Q3 to Q$_5$ are each independently selected from:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a C$_1$-C$_{10}$ alkyl group, and a phenyl group, and

* and *' each indicate a binding site to M in Formula 1:

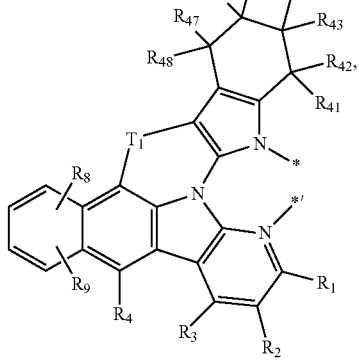

Formula 9-1

Formula 9-2

Formula 9-3

Formula 9-4

Formula 9-5

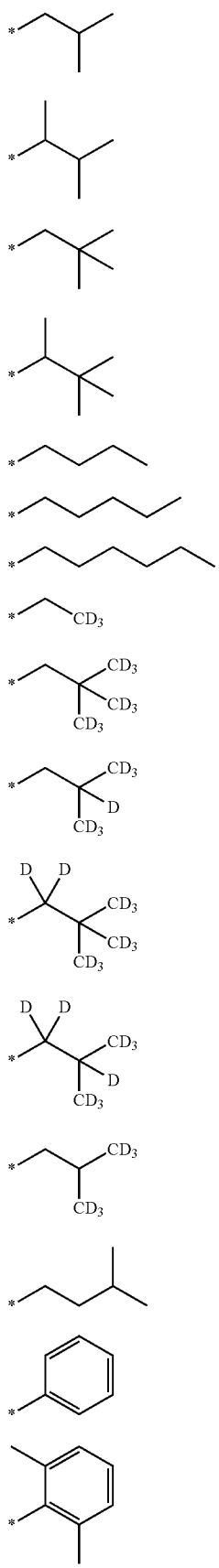
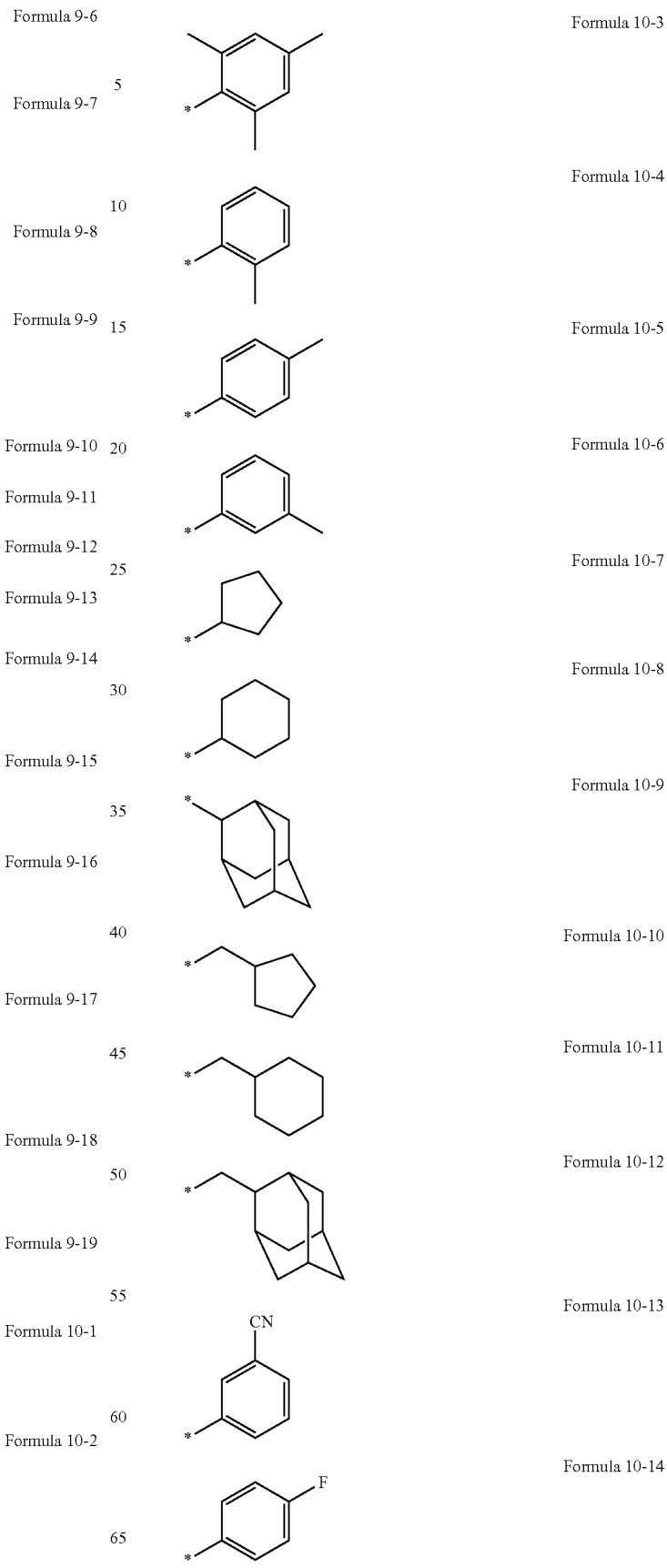

-continued
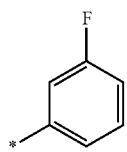
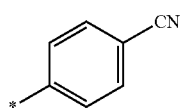
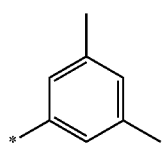
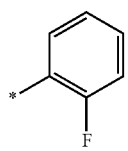
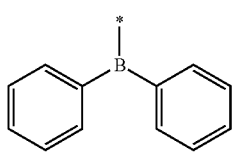
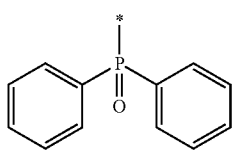
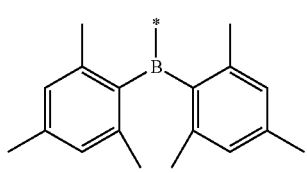
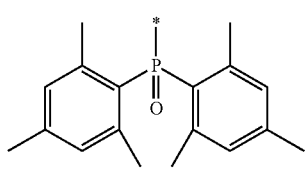
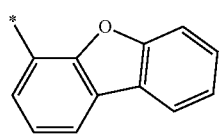
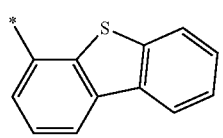
-continued
Formula 10-15
Formula 10-16
Formula 10-17
Formula 10-18
Formula 10-19
Formula 10-20
Formula 10-21
Formula 10-22
Formula 10-23
Formula 10-24
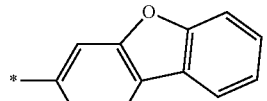
Formula 10-25
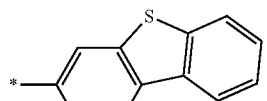
Formula 10-26
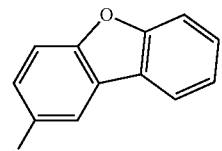
Formula 10-27
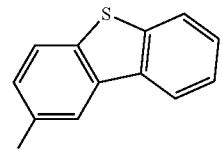
Formula 10-28
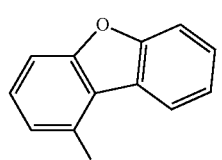
Formula 10-29
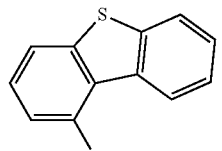
Formula 10-30
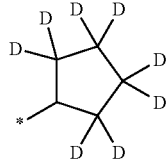
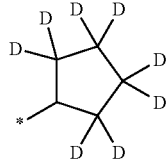
Formula 10-31
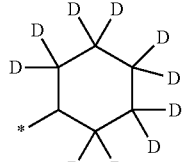
Formula 10-32
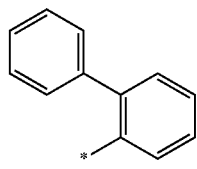
Formula 10-33

-continued

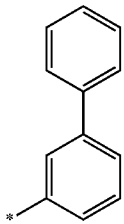
Formula 10-34

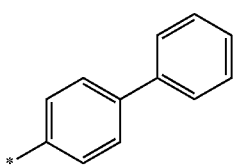
Formula 10-35

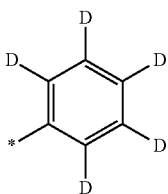
Formula 10-36 wherein * in Formulae 9-1 to 9-19 and 10-1 to 10-36 indicates a binding site to a neighboring atom.

13. The organometallic compound of claim 1, wherein ligand $L_2$ in Formula 1 is selected from ligands represented by Formula 3A to 3F:

Formula 3A $$\underset{*\quad *'}{\overset{(T_{11})_{a11}}{Y_{11}\cdots Y_{12}}}$$

Formula 3B $$\underset{*\quad *'}{\overset{(T_{11})_{a11}}{Y_{11}\quad Y_{12}}}$$

Formula 3C

[structure with N, CY₁₁, (Z₁)d1, O, O]

Formula 3D

[structure with CY₁₂, (Z₁)d1, Y₁₃, Y₁₄, Y₁₅, Y₁₆, CY₁₃, (Z₂)d2]

Formula 3E $$*—C≡C—Z_1$$

Formula 3F $$Z_1—\underset{\underset{*}{|}}{\overset{\overset{Z_2}{|}}{A_l}}—Z_3$$

wherein, in Formulae 3A to 3F
$Y_{11}$ is selected from O, N, $N(Z_1)$, $P(Z_1)(Z_2)$, and $As(Z_1)(Z_2)$, $Y_{12}$ is selected from O, N, $N(Z_3)$, $P(Z_3)(Z_4)$, and $As(Z_3)(Z_4)$, $CY_{11}$ is a $C_2$-$C_{30}$ heterocyclic group, $T_{11}$ are each independently selected from a single bond, a double bond, $*—C(Z_{11})(Z_{12})—*'$, $*—C(Z_{11})=C(Z_{12})—*'$, $*=C(Z_{11})—*'$, $*—C(Z_{11})=*'$, $*=C(Z_{11})—C(Z_{12})=C(Z_{13})—*'$, $*—C(Z_{11})=C(Z_{12})—C(Z_{13})=*'$, $*—N(Z_{11})—*'$, and a substituted or unsubstituted $C_6$-$C_{30}$ arylene group, a11 is an integer selected from 1 to 10, $Y_{13}$ to $Y_{16}$ are each independently carbon (C) or nitrogen (N), $Y_{13}$ and $Y_{14}$ are bound to each other via a single bond or a double bond, $Y_{15}$ and $Y_{16}$ are bound to each other via a single bond or a double bond, $CY_{12}$ and $CY_{13}$ are each independently selected from a $C_5$-$C_{60}$ cyclic group and a $C_2$-$C_{60}$ heterocyclic group, $A_l$ is P or As, $Z_1$ to $Z_4$ and $Z_{11}$ to $Z_{13}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $—N(Q_1)(Q_2)$, $—Si(Q_3)(Q_4)(Q_5)$, $—B(Q_6)(Q_7)$, and $—P(=O)(Q_8)(Q_9)$, d1 and d2 are each independently an integer selected from 0 to 10, and

* and *' each indicate a binding site to M in Formula 1.

14. The organometallic compound of claim 1, wherein
$CY_{11}$ is selected from a pyridine ring, a pyrimidine ring, a triazine ring, a pyrrole ring, a pyrazole ring, an imidazole ring, and a triazole ring, $CY_{12}$ and $CY_{13}$ are each independently selected from a benzene ring, a naphthalene ring, a pyridine ring, a pyrimidine ring, a triazine ring, a pyrrole ring, a pyrazole ring, an imidazole ring, and a triazole ring, and $Z_1$ to $Z_4$ and $Z_{11}$ to $Z_{13}$ are each independently selected from:

hydrogen, deuterium, —F, a cyano group, a nitro group, —SF₅, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group;

a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group, each substituted with at least one selected from deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group; and —$N(Q_1)(Q_2)$, —$Si(Q_3)(Q_4)(Q_5)$, —$B(Q_6)(Q_7)$ and —$P(=O)(Q_8)(Q_9)$, $Q_1$ to $Q_9$ are each independently selected from:

—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group.

15. The organometallic compound of claim 1, wherein ligand $L_2$ in Formula 1 is selected from ligands represented by Formulae 3-1 to 3-15:

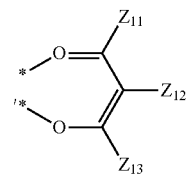

Formula 3-1

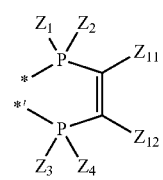

Formula 3-2

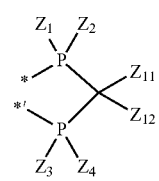

Formula 3-3

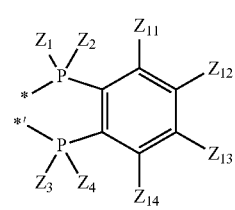

Formula 3-4

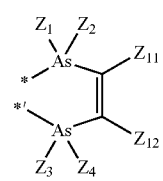

Formula 3-5

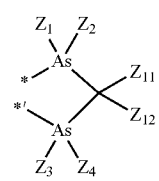

Formula 3-6

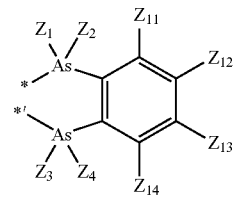

Formula 3-7

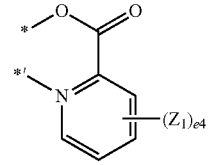

Formula 3-8

-continued

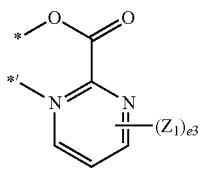
Formula 3-9

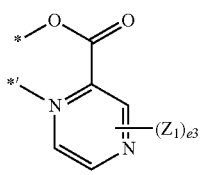
Formula 3-10

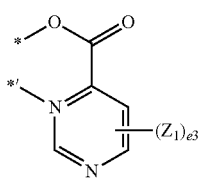
Formula 3-11

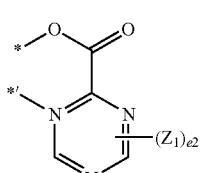
Formula 3-12

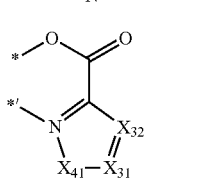
Formula 3-13

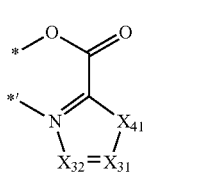
Formula 3-14

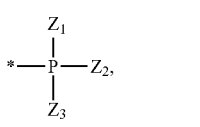
Formula 3-15 wherein, in Formulae 3-1 to 3-15, $X_{31}$ is N or $C(Z_{1a})$, and $X_{32}$ is N or $C(Z_{1b})$, $X_{41}$ is O, S, $N(Z_{1a})$, or $C(Z_{1a})(Z_{1b})$, $Z_1$ to $Z_4$, $Z_{1a}$, $Z_{1b}$, and $Z_{11}$ to $Z_{14}$ are each independently selected from:

hydrogen, deuterium, —F, a cyano group, a nitro group, —SF$_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group and a dibenzothiophenyl group;

a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group, each substituted with at least one selected from deuterium, —F, —CD$_3$, —CD$_2$H, —CDH$_2$, —CF$_3$, —CF$_2$H, —CFH$_2$, a cyano group, a nitro group, a C$_1$-C$_{10}$ alkyl group, a C$_1$-C$_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a dibenzofuranyl group, and a dibenzothiophenyl group; and —N(Q$_1$)(Q$_2$), —Si(Q$_3$)(Q$_4$)(Q$_5$), —B(Q$_6$)(Q$_7$), and —P(=O)(Q$_8$)(Q$_9$);

$Q_1$ to $Q_9$ are each independently selected from:

—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a C$_1$-C$_{10}$ alkyl group, and a phenyl group, e2 is an integer selected from 0 to 2, e3 is an integer selected from 0 to 3, e4 is an integer selected from 0 to 4, and

* and *' each indicate a binding site to M in Formula 1.

16. The organometallic compound of claim 1, wherein the organometallic compound is one of Compounds 1 to 68:

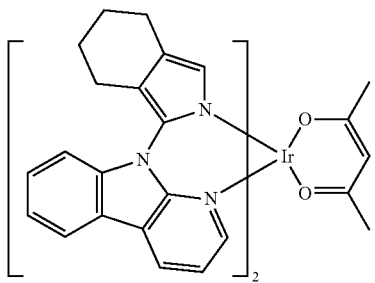
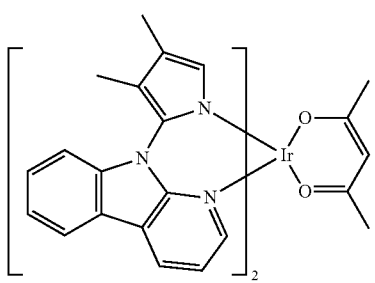
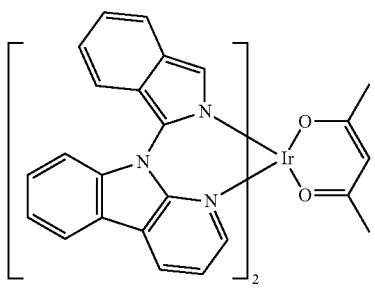
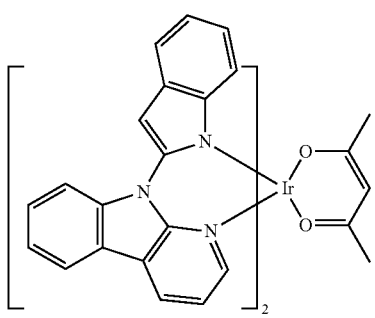
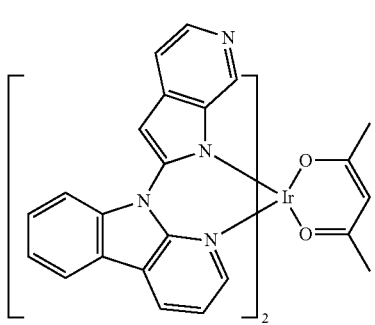
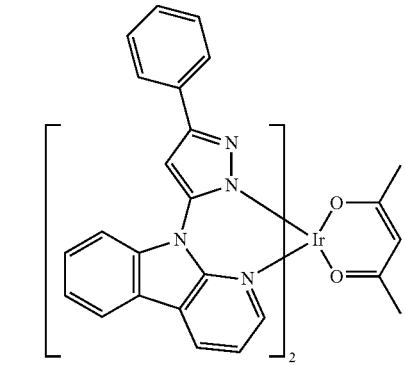
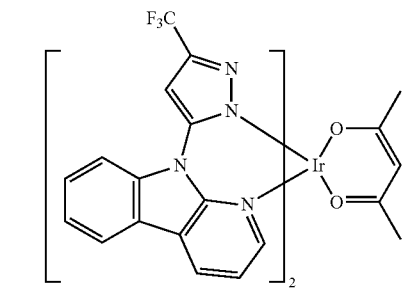
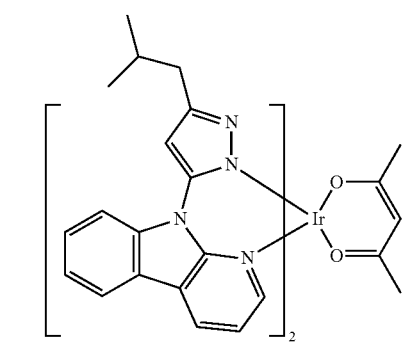
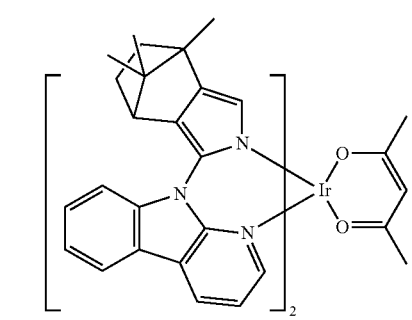
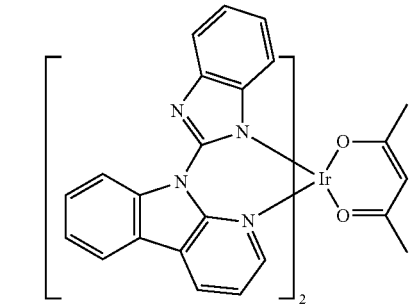

11
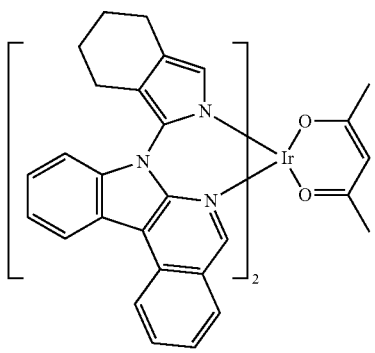
12
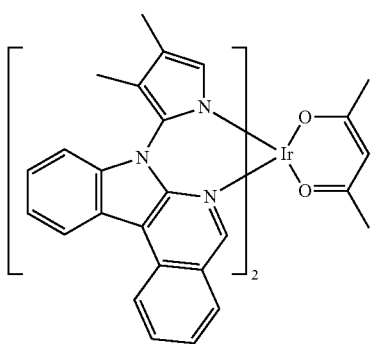
13
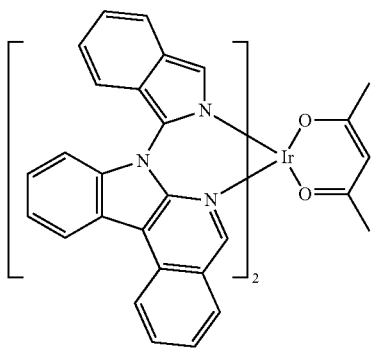
14
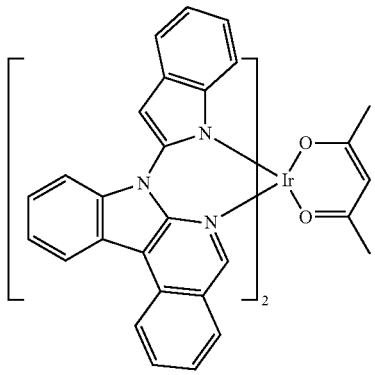
15
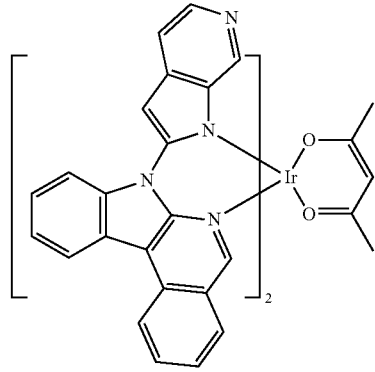
16
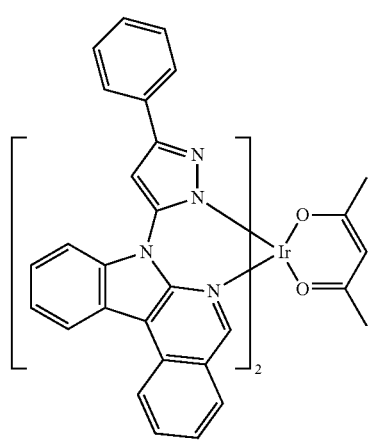
17
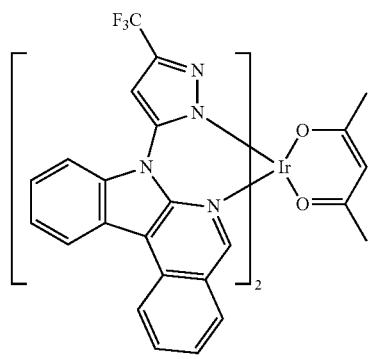
18
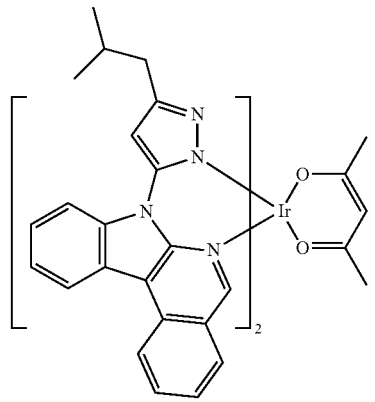

19
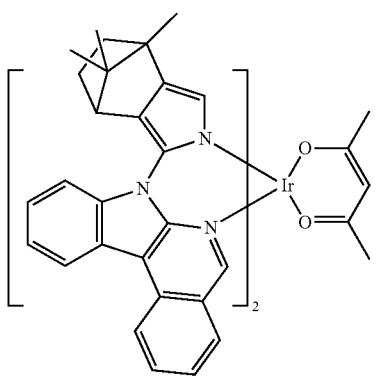
20
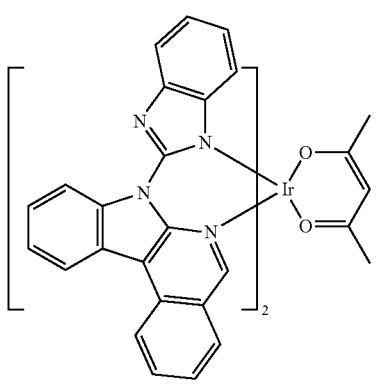
21
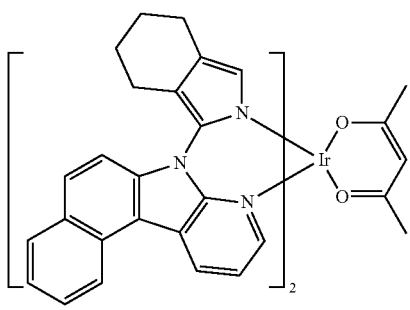
22
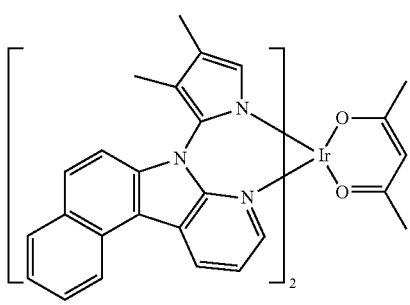
23
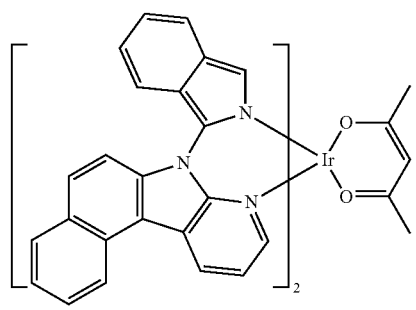
24
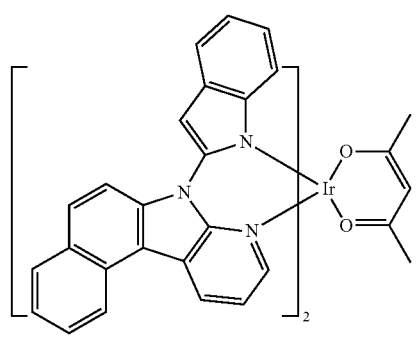
25
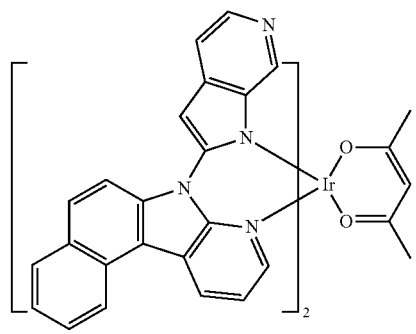
26
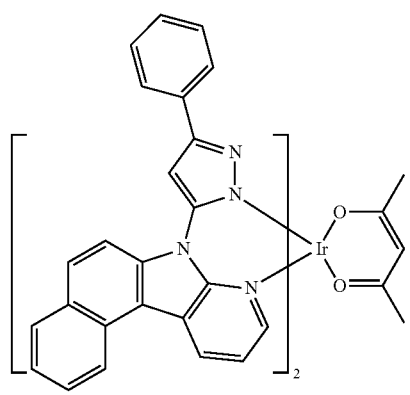

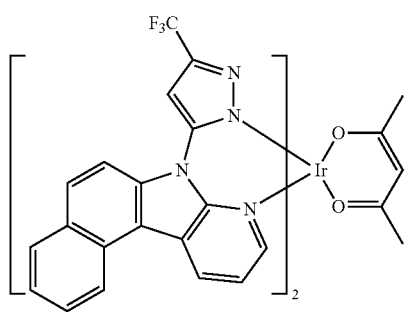
27
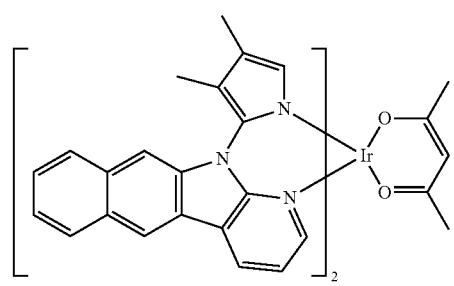
32
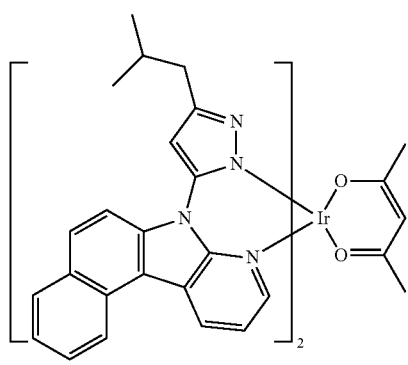
28
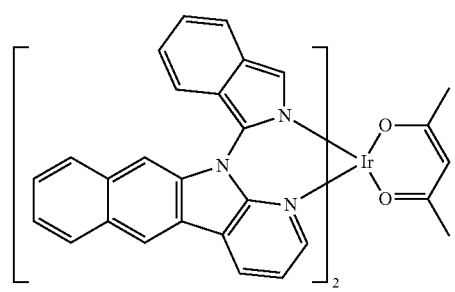
33
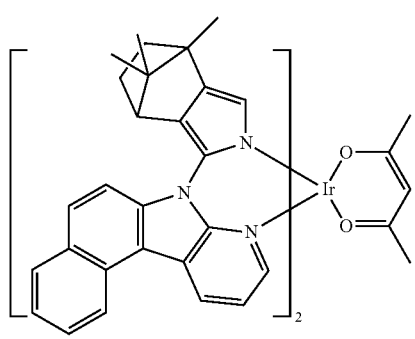
29
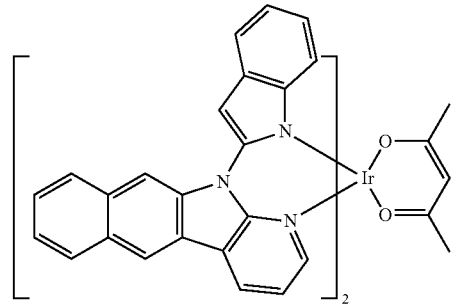
34
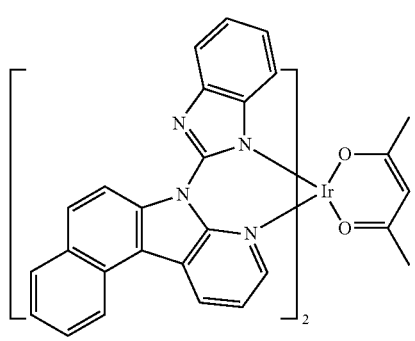
30
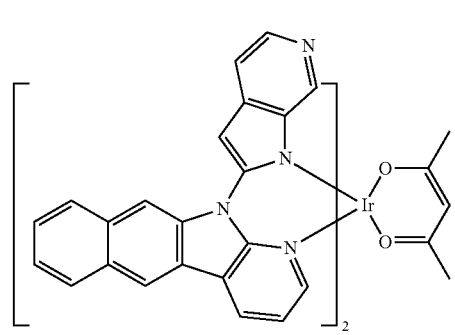
35
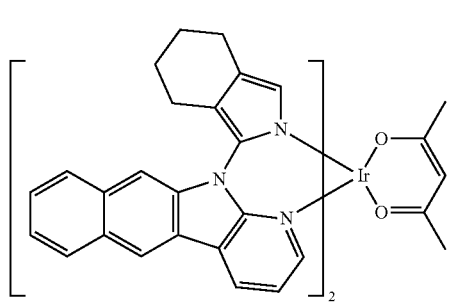
31
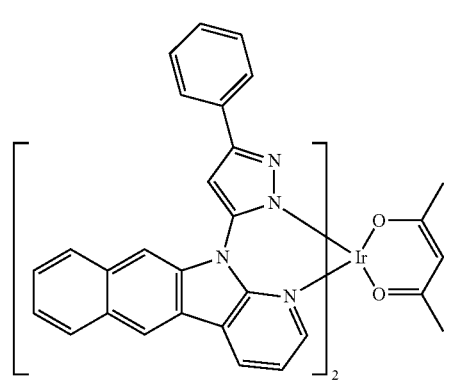
36

37
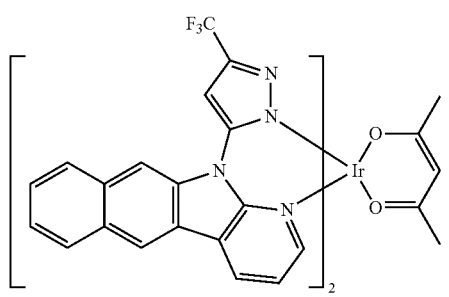
38
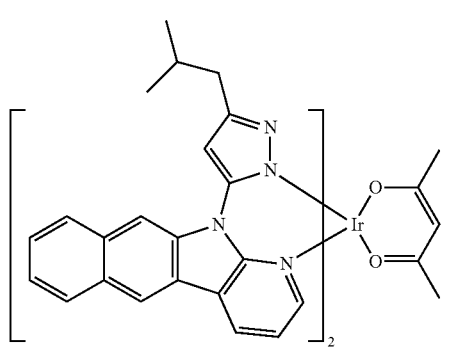
39
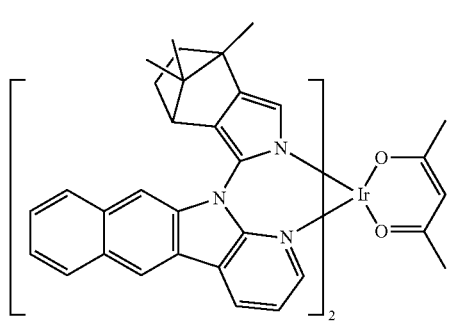
40
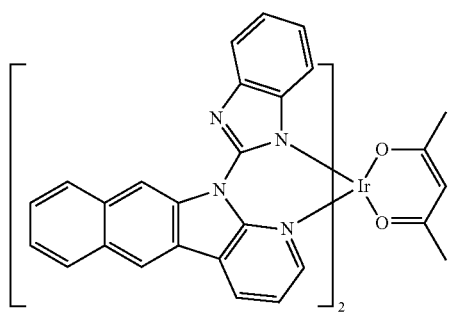
41
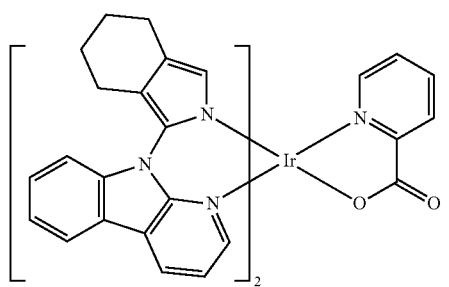
42
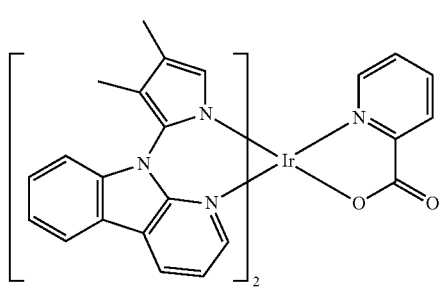
43
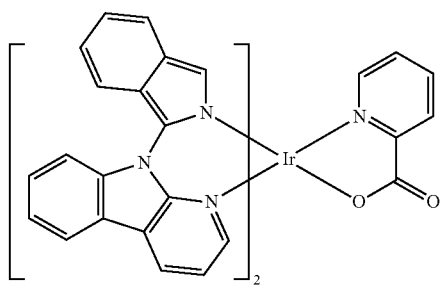
44
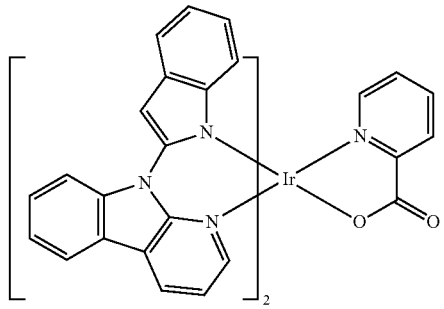
45
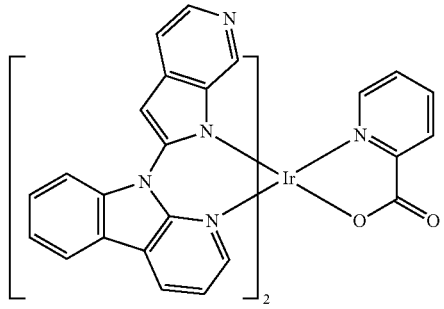
46
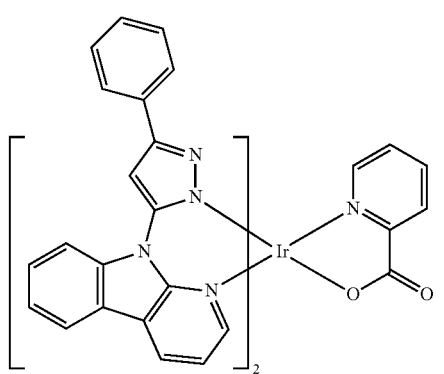

47
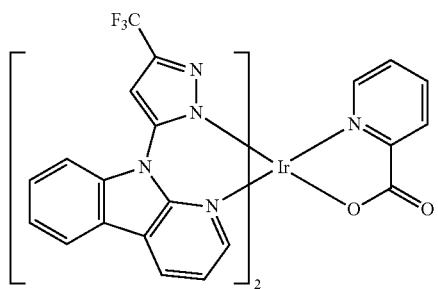
48
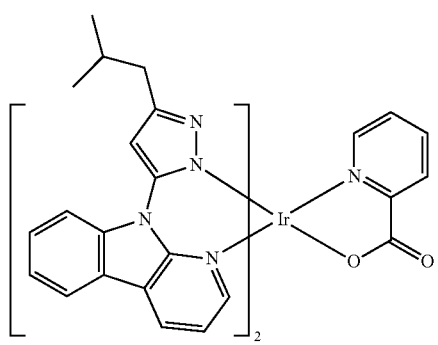
49
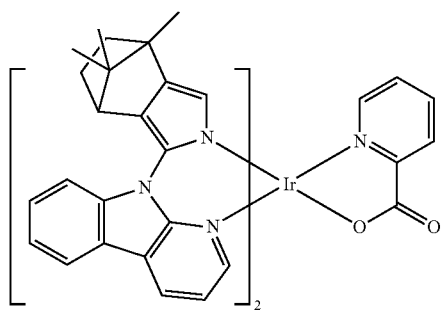
50
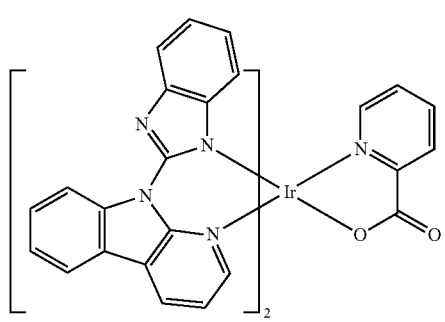
51
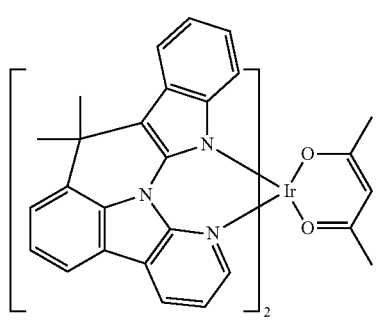
52
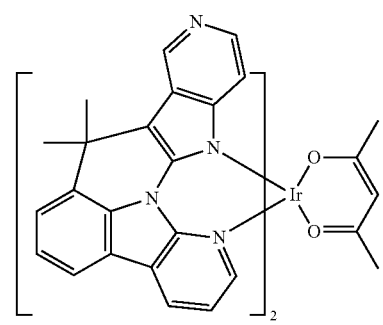
53
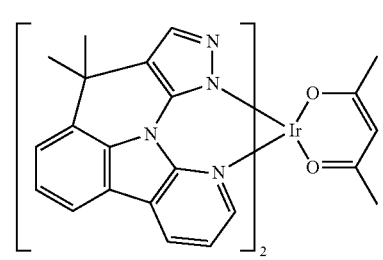
54
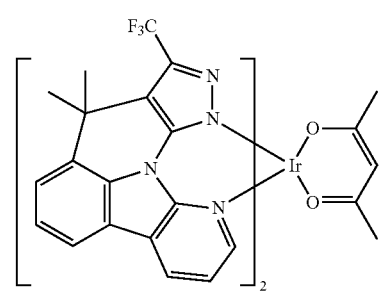
55
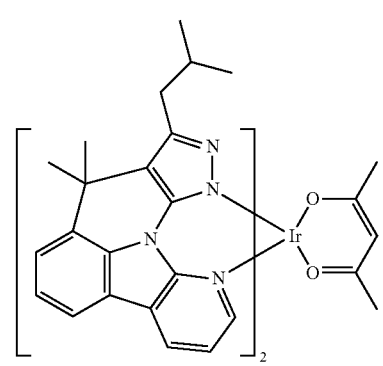
56
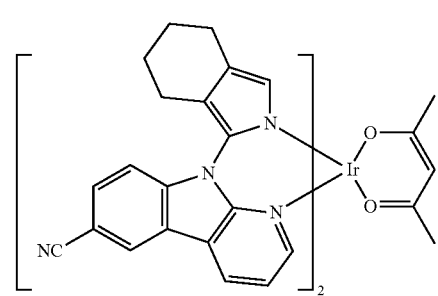

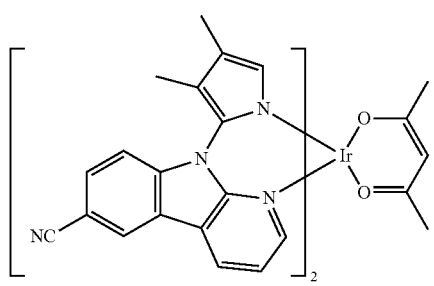
57
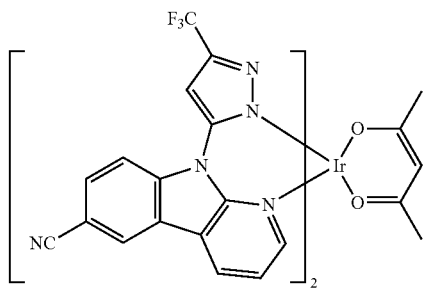
62
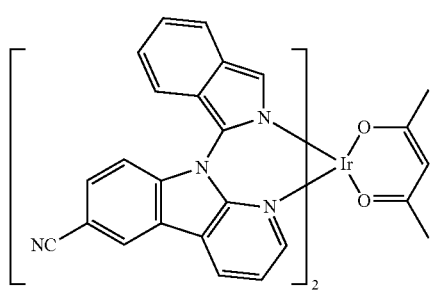
58
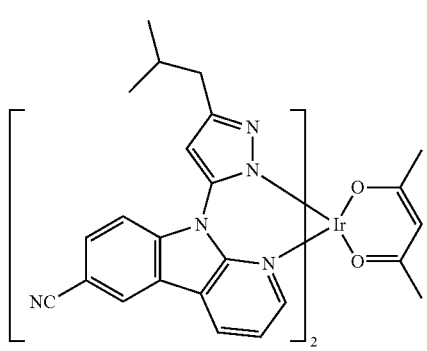
63
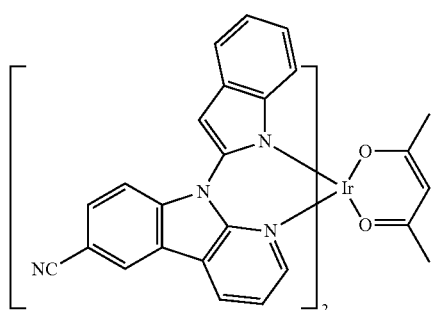
59
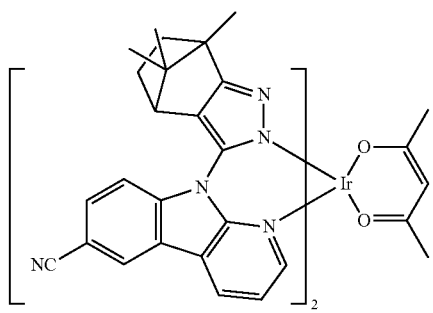
64
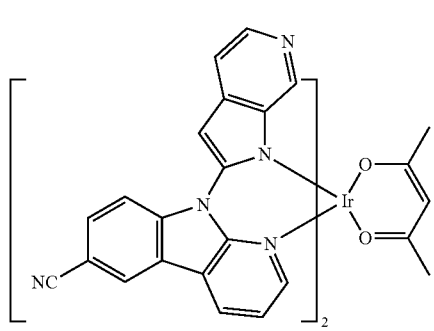
60
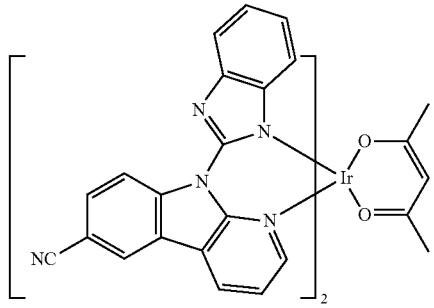
65
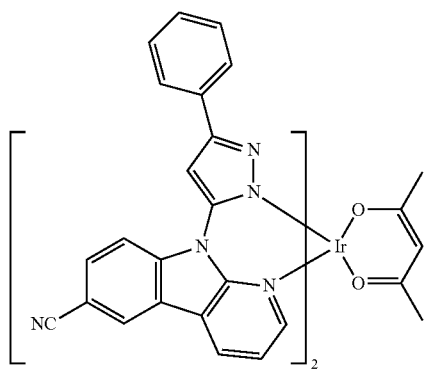
61
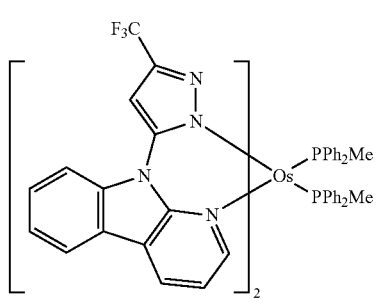
66

-continued

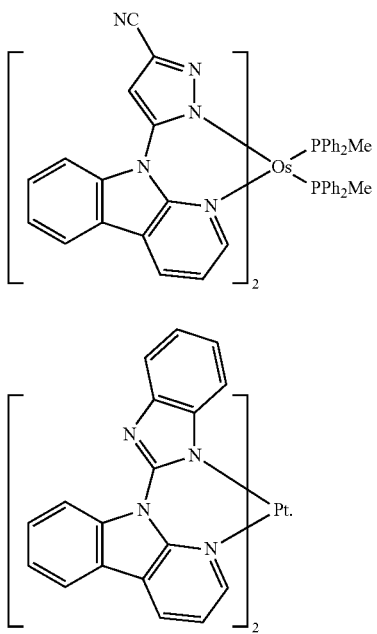

67

68

17. An organic light-emitting device comprising:
a first electrode;
a second electrode; and
an organic layer disposed between the first electrode and the second electrode,
wherein the organic layer comprises an emission layer and at least one organometallic compound of claim 1.

18. The organic light-emitting device of claim 17, wherein the first electrode is an anode,
the second electrode is a cathode,
the organic layer comprises a hole transport region disposed between the first electrode and the emission layer and an electron transport region disposed between the emission layer and the second electrode,
wherein the hole transport region comprises a hole injection layer, a hole transport layer, a buffer layer, an intermediate layer, an electron blocking layer, or any combination thereof and
wherein the electron transport region comprises a hole blocking layer, an electron transport layer, an electron injection layer, or any combination thereof.

19. The organic light-emitting device of claim 17, wherein the emission layer comprises the organometallic compound.

20. The organic light-emitting device of claim 19, wherein the emission layer further comprises a host.

* * * * *